US011541201B2

(12) United States Patent
Crow et al.

(10) Patent No.: US 11,541,201 B2
(45) Date of Patent: Jan. 3, 2023

(54) SLEEP PERFORMANCE SYSTEM AND METHOD OF USE

(71) Applicant: NEUROGENECES, INC., Santa Fe, NM (US)

(72) Inventors: Karen Crow, Santa Fe, NM (US); Matt Sanders, Santa Fe, NM (US)

(73) Assignee: NEUROGENECES, INC., Santa Fe, NM (US)

( * ) Notice: Subject to any disclaimer, the term of this patent is extended or adjusted under 35 U.S.C. 154(b) by 495 days.

(21) Appl. No.: 16/151,715

(22) Filed: Oct. 4, 2018

(65) Prior Publication Data

US 2019/0099582 A1 Apr. 4, 2019

Related U.S. Application Data

(60) Provisional application No. 62/568,249, filed on Oct. 4, 2017, provisional application No. 62/661,932, filed on Apr. 24, 2018.

(51) Int. Cl.
*A61M 21/02* (2006.01)
*A61B 5/00* (2006.01)
(Continued)

(52) U.S. Cl.
CPC .............. *A61M 21/02* (2013.01); *A61B 5/01* (2013.01); *A61B 5/0245* (2013.01);
(Continued)

(58) Field of Classification Search
None
See application file for complete search history.

(56) References Cited

U.S. PATENT DOCUMENTS 5,999,846 A * 12/1999 Pardey ................. A61B 5/4812
600/544
7,460,899 B2 12/2008 Almen
(Continued)

FOREIGN PATENT DOCUMENTS

EP 3415080 12/2018
EP 3415089 12/2018
(Continued)

OTHER PUBLICATIONS

Papalambros et al. Acoustic Enhancement of Sleep Slow Oscillations and Concomitant Memory Improvement in Older Adults, Frontiers in Human Neuroscience, Mar. 8, 2017, vol. 11, Article 109, pp. 1-14.
(Continued)

*Primary Examiner* — Jacqueline Cheng
*Assistant Examiner* — Jairo H Portillo
(74) *Attorney, Agent, or Firm* — Peacock Law P.C.; Janeen Vilven

(57) ABSTRACT

Sleep performance systems and methods of using the same are disclosed. The sleep performance systems can improve the quality of sleep by making one or more recommendations to the subject for increasing a sleep quality score. The sleep performance systems can have one or more electroencephalography (EEG) electrodes configured to measure a subject's brain activity during sleep. The sleep performance systems can have a processor configured to quantify the quality of the subject's slow-wave sleep by determining one or more sleep performance scores associated with the measured brain activity. The sleep performance systems can recommend and/or activate sleep improvement programs based on various threshold scores.

17 Claims, 47 Drawing Sheets

(51) Int. Cl.
*A61B 5/024* (2006.01)
*A61B 5/01* (2006.01)
*A61B 5/0245* (2006.01)
*A61B 5/11* (2006.01)
*A61B 5/375* (2021.01)
*A61B 5/398* (2021.01)
*A61M 21/00* (2006.01)
*A61B 5/113* (2006.01)

(52) U.S. Cl.
CPC ........ *A61B 5/02405* (2013.01); *A61B 5/1116* (2013.01); *A61B 5/375* (2021.01); *A61B 5/398* (2021.01); *A61B 5/4815* (2013.01); *A61B 5/6831* (2013.01); *A61B 5/6885* (2013.01); *A61B 5/7278* (2013.01); *A61B 5/02416* (2013.01); *A61B 5/1135* (2013.01); *A61B 5/4812* (2013.01); *A61M 2021/0022* (2013.01); *A61M 2021/0027* (2013.01); *A61M 2021/0044* (2013.01); *A61M 2021/0066* (2013.01); *A61M 2021/0072* (2013.01); *A61M 2205/02* (2013.01); *A61M 2205/0216* (2013.01); *A61M 2205/13* (2013.01); *A61M 2205/332* (2013.01); *A61M 2205/3331* (2013.01); *A61M 2205/3368* (2013.01); *A61M 2205/3553* (2013.01); *A61M 2205/3569* (2013.01); *A61M 2205/3592* (2013.01); *A61M 2205/505* (2013.01); *A61M 2205/52* (2013.01); *A61M 2205/583* (2013.01); *A61M 2230/04* (2013.01); *A61M 2230/06* (2013.01); *A61M 2230/10* (2013.01); *A61M 2230/14* (2013.01); *A61M 2230/205* (2013.01); *A61M 2230/42* (2013.01); *A61M 2230/50* (2013.01); *A61M 2230/60* (2013.01); *A61M 2230/62* (2013.01); *A61M 2230/63* (2013.01)

(56) References Cited

U.S. PATENT DOCUMENTS

| | | |
|---|---|---|
| 8,029,431 B2 | 10/2011 | Tononi |
| 8,213,670 B2 | 7/2012 | Lai |
| 9,320,885 B2 | 4/2016 | Vasapollo |
| 10,080,860 B2 | 9/2018 | Molina |
| 10,137,276 B2 | 11/2018 | Molina et al. |
| 10,220,183 B2 | 3/2019 | Garcia et al. |
| 10,328,234 B2 | 6/2019 | Molina et al. |
| 10,512,428 B2 | 12/2019 | Laura Lapoint et al. |
| 10,524,682 B2 | 1/2020 | Molina et al. |
| 10,549,067 B2 | 2/2020 | Molina et al. |
| 10,610,660 B2 | 4/2020 | Pfundtner et al. |
| 10,695,528 B2 | 6/2020 | Soulet De Brugiere et al. |
| 10,729,875 B2 | 8/2020 | Geerlings et al. |
| 2005/0215947 A1* | 9/2005 | Heruth .......... A61B 5/4815 604/66 |
| 2007/0123758 A1* | 5/2007 | Miesel .......... A61N 1/36067 607/2 |
| 2008/0081941 A1* | 4/2008 | Tononi .......... A61M 21/02 600/14 |
| 2009/0198145 A1* | 8/2009 | Chow .......... A61K 31/5517 600/595 |
| 2010/0049008 A1 | 2/2010 | Doherty et al. |
| 2010/0087701 A1 | 4/2010 | Berka et al. |
| 2010/0240982 A1* | 9/2010 | Westbrook .......... A61B 5/6814 600/391 |
| 2014/0073486 A1* | 3/2014 | Ahmed .......... G16H 20/40 482/9 |
| 2014/0206722 A1* | 7/2014 | Pellegrini .......... A61P 25/20 514/320 |
| 2015/0092972 A1 | 4/2015 | Lai et al. |
| 2015/0164238 A1* | 6/2015 | Benson .......... A61B 5/4806 340/540 |
| 2016/0220783 A1* | 8/2016 | Garcia Molina .... A61B 5/4836 |
| 2016/0296164 A1 | 10/2016 | Molina |
| 2017/0055899 A1 | 3/2017 | Bandyopadhyay et al. |
| 2017/0164857 A1 | 6/2017 | Soulet De Brugiere et al. |
| 2017/0164903 A1 | 6/2017 | Soulet De Brugiere et al. |
| 2017/0196474 A1 | 7/2017 | Molina et al. |
| 2017/0304587 A1* | 10/2017 | Santostasi .......... A61B 5/7242 |
| 2017/0340855 A1 | 11/2017 | Soulet De Brugiere et al. |
| 2017/0368297 A1* | 12/2017 | Tyler .......... A61M 21/02 |
| 2018/0236232 A1 | 8/2018 | Soulet De Brugiere et al. |
| 2018/0360376 A1 | 12/2018 | Molina |
| 2018/0361110 A1 | 12/2018 | Molina et al. |
| 2019/0083028 A1 | 3/2019 | Molina et al. |
| 2019/0192069 A1 | 6/2019 | Molina et al. |
| 2019/0216353 A1 | 7/2019 | Molina |
| 2019/0254591 A1 | 8/2019 | Molina et al. |
| 2019/0298967 A1 | 10/2019 | Molina et al. |
| 2019/0336723 A1 | 11/2019 | Molina et al. |
| 2019/0343455 A1 | 11/2019 | Molina et al. |
| 2020/0000356 A1 | 1/2020 | Talamini et al. |
| 2020/0077919 A1 | 3/2020 | Molina |
| 2020/0146619 A1 | 5/2020 | Molina et al. |
| 2020/0170568 A1 | 6/2020 | Mercier et al. |

FOREIGN PATENT DOCUMENTS

| | | |
|---|---|---|
| FR | 3059556 | 6/2018 |
| FR | 3074052 | 5/2019 |
| WO | 2012/117343 | 9/2012 |
| WO | 2012/170586 | 12/2012 |
| WO | 2016/097937 | 6/2016 |
| WO | 2017/021662 | 2/2017 |
| WO | 2017/098185 | 6/2017 |
| WO | 2018/122226 | 7/2018 |
| WO | 2018/229006 | 12/2018 |
| WO | 2019/070939 | 4/2019 |

OTHER PUBLICATIONS

Ngo et al. Auditory Closed-Loop Stimulation of the Sleep Slow Oscillation Enhances Memory, Neuron, May 8, 2013, No. 78, pp. 545-553.

Santostasi et al. Phase-locked loop for precisely time acoustic stimulation during sleep, Journal of Neuroscience Methods 259 (2016) 101-114.

Walter Moraes, Ronaldo Piovezan, Dalva Poyares, Lia Rita Bittencourt, Rogerio Santos-Silva, Sergio Tufik "Effects of aging on sleep structure throughout adulthood: a population based study". Sleep Medicine 15 (2014) 401-409.

Ohayon MM, Carskadon MA, Guilleminault C, Vitiello MV. "Meta-analysis of quantitative sleep parameters from childhood to old age in healthy individuals: developing normative sleep values across the human lifespan". Sleep. Nov. 1, 2004.

Nunan D, Sandercock GR, Brodie DA. "A quantitative systematic review of normal values for short-term heart rate variability in healthy adults." Pacing Clin Electrophysiol. Nov. 2010;33(11):1407-17.

Umetani K, Singer DH, McCraty R, Atkinson M. "Twenty-four hour time domain heart rate variability and heart rate: relations to age and gender over nine decades." J Am Coll Cardiol. Mar. 1, 1998;31(3):593-601.

Cox, Roy, et al., "Sound Asleep; Processing and Retention of Slow Oscillation Phase-Targeted Stimuli", PLoS One, vol. 9, No. 7, 2014, e101567 1-12.

Leminen, Muka M., et al., "Enhanced Memory Consolidation Via Automatic Sound Stimulation During Non-REM Sleep", Sleep, vol. 40, No. 3, 2017, 1-10.

Ong, Ju Lynn, et al., "Effects of phase-locked acoustic stimulation during a nap on EEG spectra and declarativee memory consolidation", Sleep Machine, vol. 20, 2015, 88-97.

Tononi, G. et al., et al., "Enhancing sleep slow waves with natural stimuli", Medicamundi, vol. 54, No. 2, 2010, 82-88.

(56) References Cited

OTHER PUBLICATIONS

Weigenand, Arne, et al., "Timing matters: open-loop stimulation does not improve overnight consolidation of words pairs in humans", European Journal of Neuroscience, vol. 44, 2016, 2357-2368.

* cited by examiner

| Ah Ha | Triggered Recommendation | Contributors - Option 1: Performance vs Personal Baseline | Option 2: Performance vs Cohort | Points |
|---|---|---|---|---|
| Insufficient Deep Sleep | Deep Sleep Audio Stimulation | Deep Sleep > 10% below personal baseline | Deep Sleep < 75 points for cohort | 3 |
| | | Deep Sleep > 20% below personal baseline | Deep Sleep < 65 points for cohort | 3 |
| | | Deep Sleep > 30% below personal baseline | Deep Sleep < 55 points for cohort | 3 |
| Weak Deep Sleep | Deep Sleep Audio Stimulation | Amplitude during Deep Sleep is > 20% below baseline | Amplitude during Deep Sleep is 20% < Cohort | 2 |
| | | Amplitude during Deep Sleep is > 40% below baseline | Amplitude during Deep Sleep is 40% < Cohort | 2 |
| | | Amplitude during Deep Sleep is > 60% below baseline | Amplitude during Deep Sleep is 60% < Cohort | 2 |
| Fragmented Deep Sleep | Deep Sleep Audio Stimulation | Longest Duration of DS is 20% > baseline | Longest Duration of Deep Sleep 20% < Cohort | 2 |
| | | Longest Duration of DS is 40% > baseline | Longest Duration of Deep Sleep 40% < Cohort | 2 |
| | | Longest Duration of DS is 60% > baseline | Longest Duration of Deep Sleep 60% < Cohort | 2 |
| Insufficient Total Sleep: total time in bed is insufficient | Tips: Need to allocate more time to sleep; Make sure to optimize DS if getting short sleep | | | 2 |
| | | Total Sleep 20% below personal baseline | Total Sleep <70 points for cohort | 2 |
| | | Total Sleep 40% below personal baseline | Total Sleep <60 points for cohort | 2 |
| | | Total Sleep 60% below personal baseline | Total Sleep <50 points for cohort | 2 |
| Insufficient Total Sleep: poor sleep efficiency | Guided Meditation for sleep relaxation | Sleep Efficiency > 5% below personal baseline | Sleep Efficiency points < 85 points for cohort | 2 |
| | | Sleep Efficiency > 10% below personal baseline | Sleep Efficiency points < 75 points for cohort | 2 |
| | | Sleep Efficiency > 15% below personal baseline | Sleep Efficiency points < 65 points for cohort | 2 |
| Low recovery level | Tips: take it easy, you're not at full strength today | HRV > 20% below personal baseline | HRVpoints < 80 | 4 |
| | | HRV > 30% below personal baseline | HRVpoints < 60 | 4 |
| | | HRV > 40% below personal baseline | HRVpoints < 40 | 4 |
| Terrific Sleep Quality Score | Encouragement: Keep up the great work | Deep Sleep > 10% above personal baseline | Deep Sleep =100 points for cohort | 3 |
| | | Deep Sleep > 20% above personal baseline | | 3 |
| | | Deep Sleep > 30% above personal baseline | | 3 |
| Great Duration of Deep Sleep | Encouragement: Congrats! You're keeping your brain nice and healthy! | Deep Sleep Duration > 20% above personal best | Deep Sleep Duration = 100 points for cohort | 3 |
| | | Deep Sleep Duration > 40% above personal best | | 3 |
| | | Deep Sleep Duration > 60% above personal best | | 3 |

FIG. 5

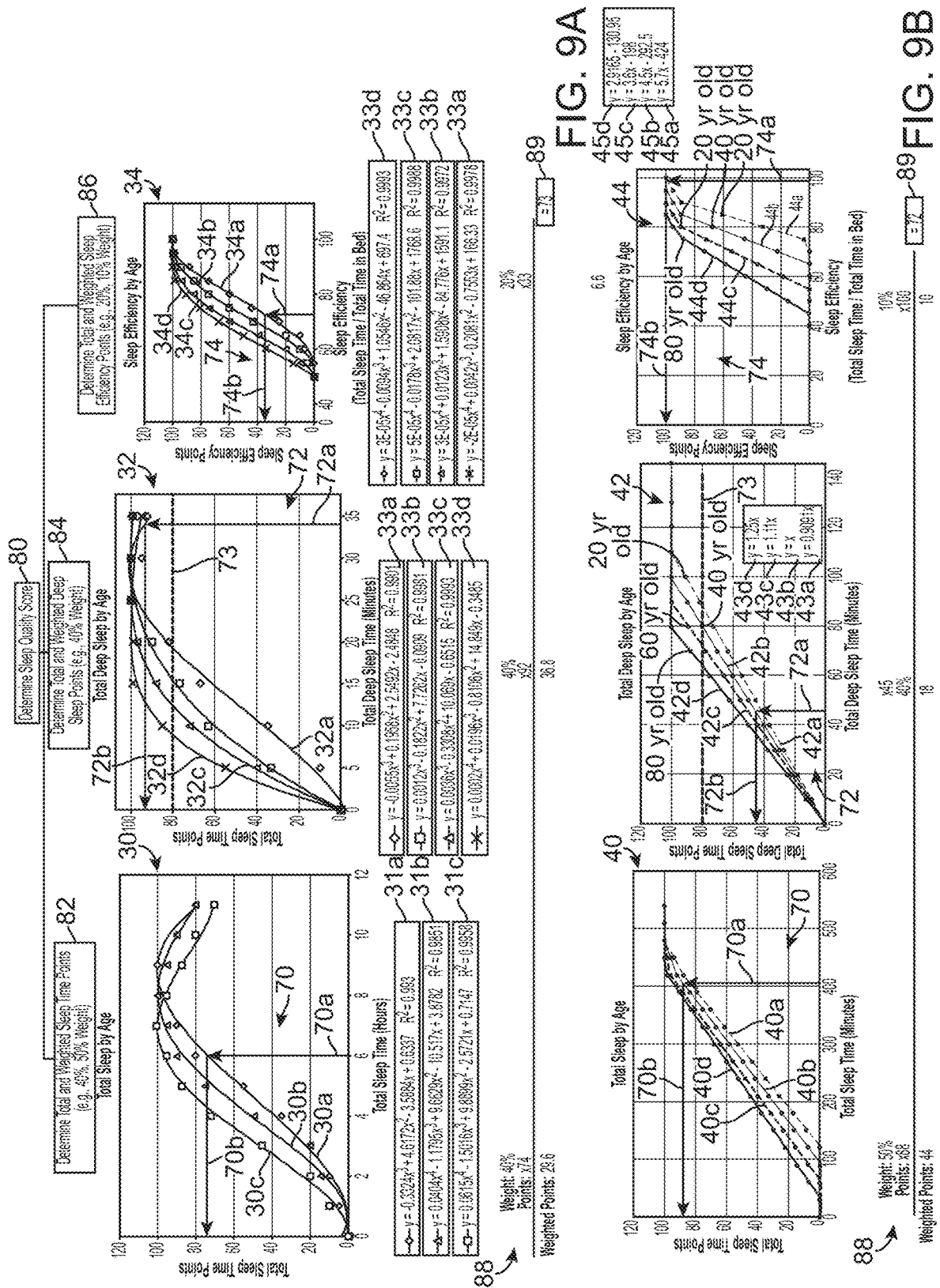

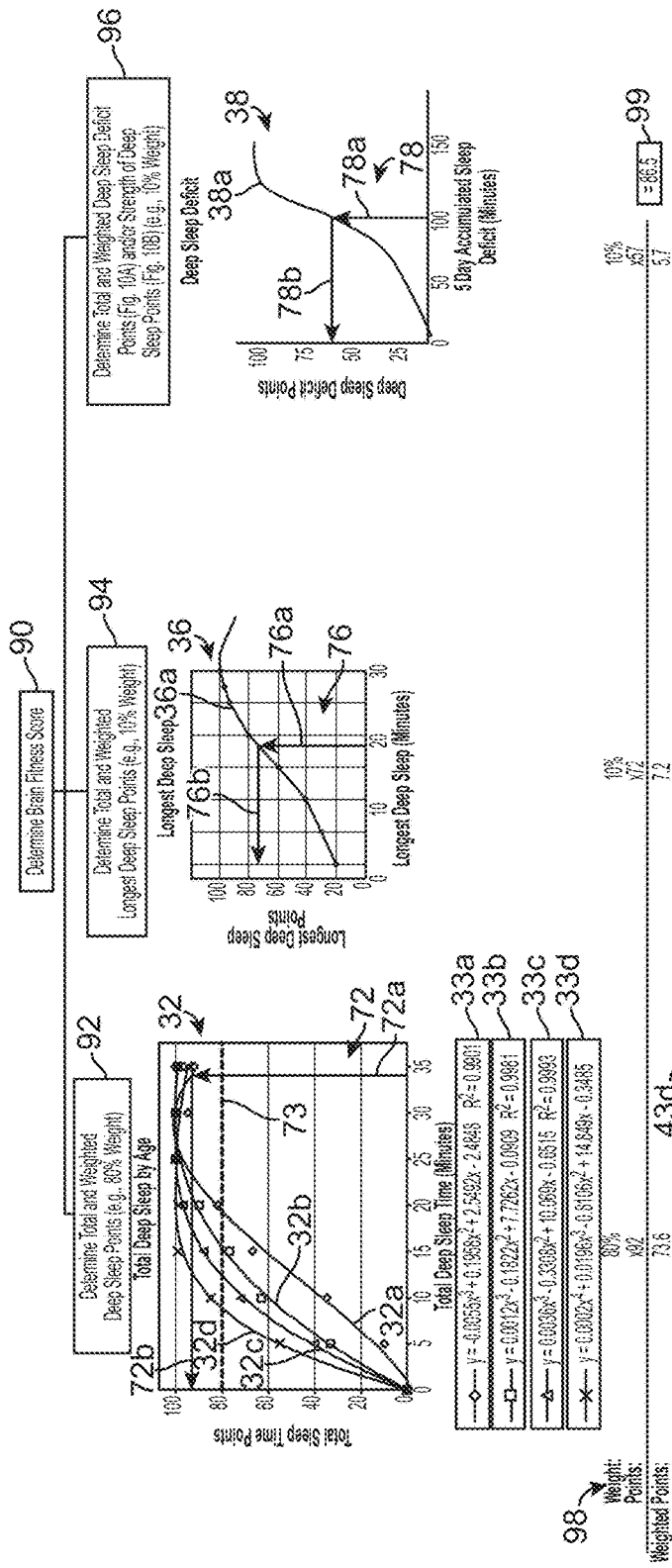
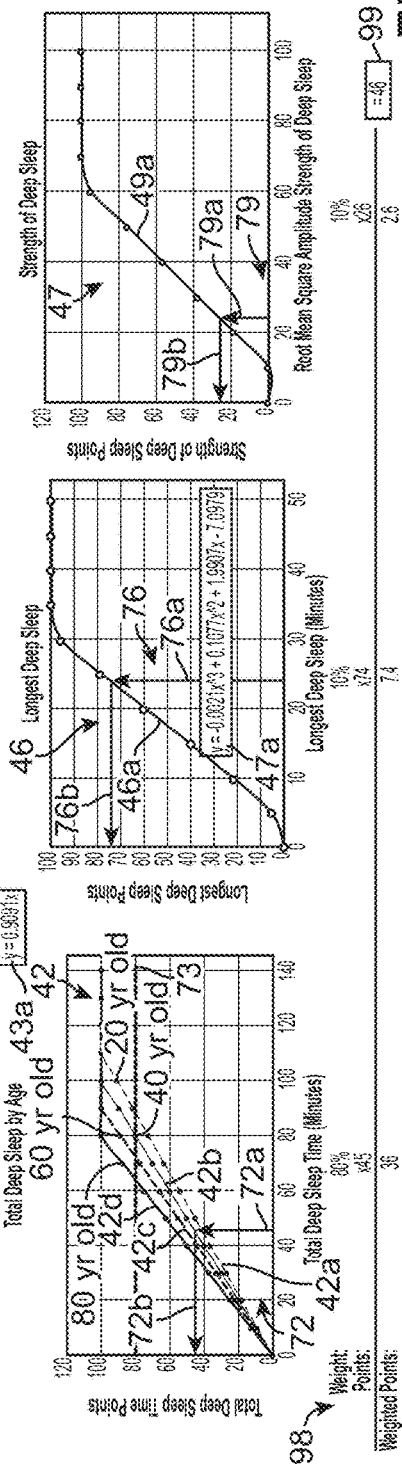
FIG. 10A
FIG. 10B

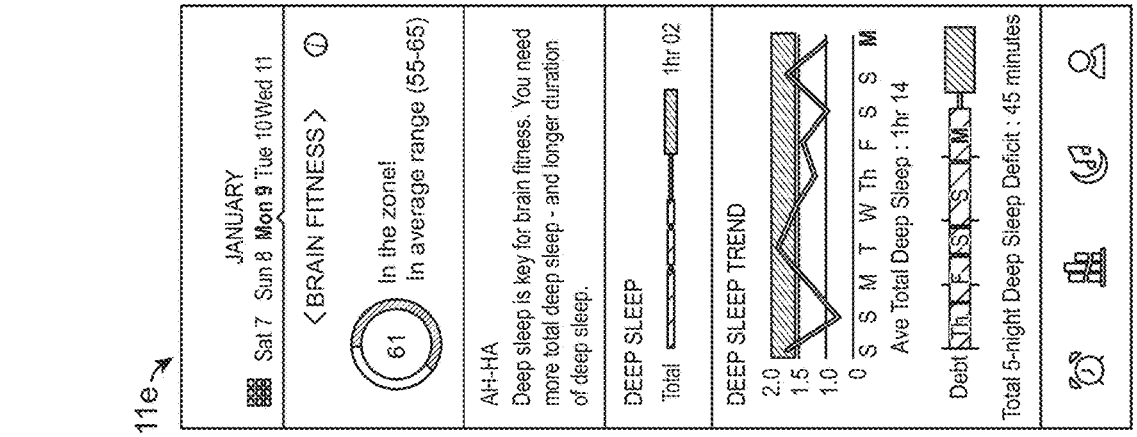
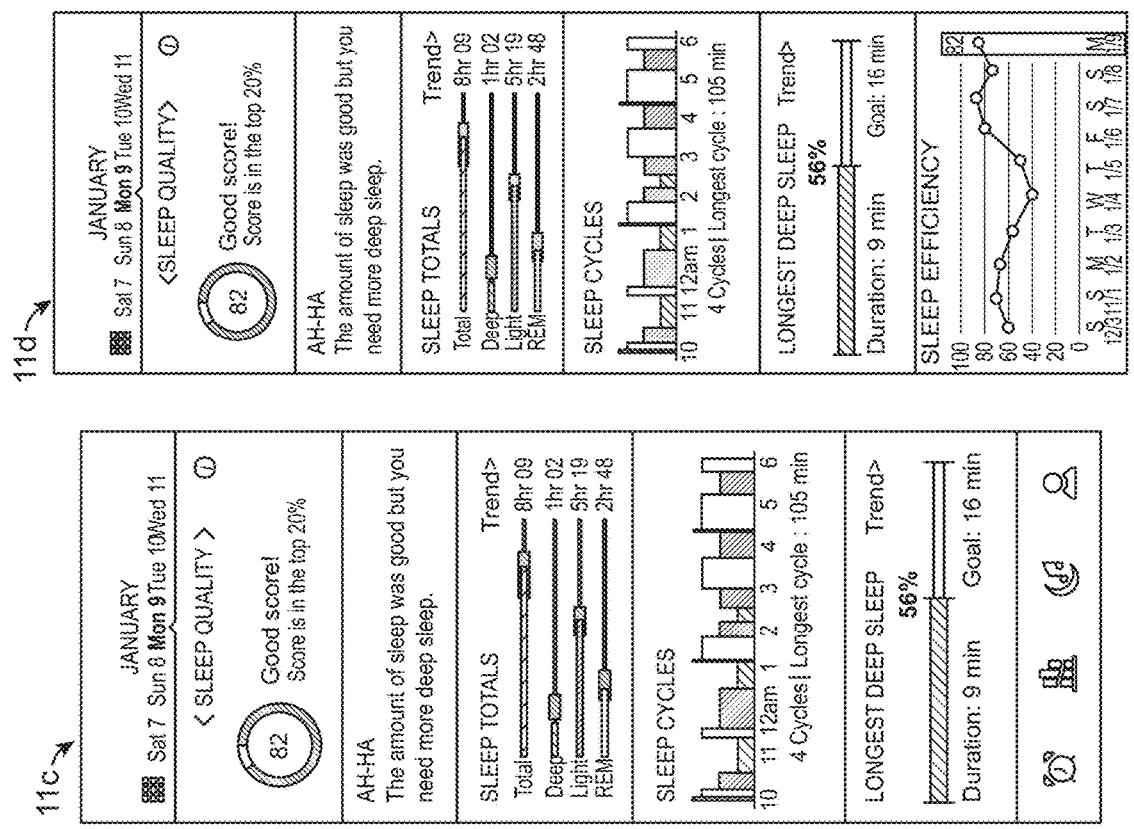
FIG. 11C   FIG. 11D   FIG. 11E

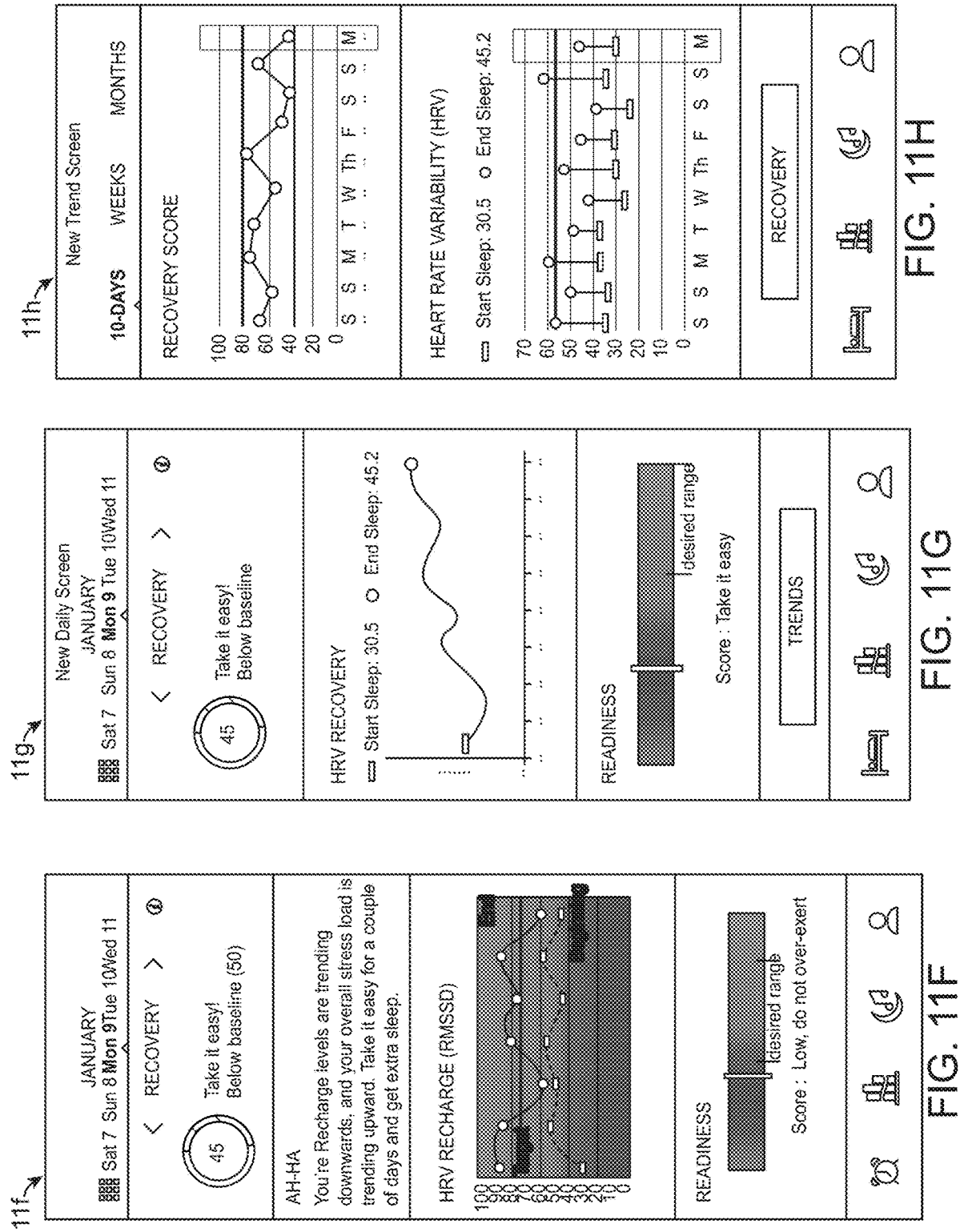

Table 1
Sleep structure and age

| Sleep structure | Age (years) | | | | | | | | | | | | P (one-way ANOVA) | Effect size[a] |
|---|---|---|---|---|---|---|---|---|---|---|---|---|---|---|
| | 20-24 (n=106) | 25-29 (n=130) | 30-34 (n=129) | 35-39 (n=119) | 40-44 (n=128) | 45-49 (n=126) | 50-54 (n=87) | 55-59 (n=79) | 60-64 (n=48) | 65-69 (n=40) | 70-74 (n=26) | 75-80 (n=24) | | |
| TST | 376.3±75.4 | 367.9±78.4 | 364.0±71.0 | 353.4±82.9 | 338.0±78.1 | 338.2±74.9 | 316.9±69.3 | 325.9±70.9 | 329.1±51.2 | 314.5±80.5 | 292.0±78.0 | 291.0±66.0 | <0.01 | 0.08 |
| Eff | 87.9±9.5 | 86.1±11.8 | 86.8±8.6 | 81.6±15.5 | 82.5±12.2 | 81.3±12.5 | 78.1±13.0 | 77.7±11.8 | 79.0±9.6 | 74.9±14.5 | 72.8±17.3 | 65.4±13.0 | <0.01 | 0.13 |
| Lat | 13.8±17.5 | 15.0±20.1 | 14.5±16.8 | 19.6±32.7 | 13.4±13.9 | 17.4±21.0 | 17.8±18.7 | 17.3±18.3 | 17.3±15.0 | 20.5±28.7 | 28.7±41.1 | 34.6±45.9 | 0.01 | 0.03 |
| REMlat | 106.4±50.9 | 97.5±45.5 | 95.6±44.3 | 89.8±37.9 | 97.0±47.5 | 102.5±57.0 | 106.1±58.6 | 109.8±64.2 | 109.8±65.4 | 95.0±52.0 | 129.1±83.1 | 120.9±3.0 | 0.01 | 0.02 |
| WASO | 38.9±35.5 | 44.4±40.5 | 41.0±30.2 | 55.0±47.1 | 58.1±45.8 | 61.0±45.3 | 72.3±47.7 | 78.1±44.9 | 72.1±37.4 | 84.1±40.4 | 81.1±49.2 | 121.6±49.6 | <0.01 | 0.14 |
| AI | 8.8±4.6 | 10.4±5.8 | 11.4±6.7 | 12.5±7.8 | 15.3±10.6 | 16.3±13.3 | 19.6±15.3 | 19.0±11.1 | 22.3±14.6 | 20.9±12.4 | 17.5±8.8 | 21.8±13.7 | <0.01 | 0.14 |
| RAI | 1.9±2.3 | 2.4±3.9 | 3.3±5.1 | 4.1±5.3 | 5.9±10.0 | 7.3±11.3 | 9.0±11.7 | 8.6±9.4 | 13.9±13.6 | 10.3±9.9 | 9.6±8.7 | 13.3±15.2 | <0.01 | 0.13 |
| NRAI | 7.1±3.4 | 7.9±3.8 | 8.2±4.1 | 8.5±5.1 | 9.4±6.4 | 9.1±5.3 | 10.7±7.4 | 10.4±6.3 | 8.9±5.4 | 10.8±8.3 | 8.1±4.7 | 8.5±5.2 | <0.01 | 0.04 |
| S1d | 13.6±9.6 | 14.3±10.0 | 14.5±8.8 | 12.7±8.2 | 14.9±10.7 | 16.0±10.3 | 16.2±13.2 | 17.3±13.2 | 15.9±9.4 | 13.7±5.3 | 13.3±6.6 | 18.2±10.1 | 0.05 | 0.02 |
| S2d | 204.4±52.1 | 197.4±49.1 | 197.0±54.6 | 177.7±53.7 | 184.7±49.7 | 181.9±48.4 | 172.6±47.3 | 185.4±51.2 | 184.0±38.5 | 178.4±56.1 | 165.7±61.0 | 169.9±58.4 | <0.01 | 0.04 |
| SWSd | 87.4±26.5 | 83.7±25.3 | 77.5±25.9 | 75.4±26.3 | 69.9±28.9 | 70.7±30.0 | 70.2±25.2 | 63.4±31.5 | 69.3±26.5 | 67.2±37.3 | 63.3±27.0 | 53.6±33.2 | <0.01 | 0.07 |
| REMd | 70.9±30.5 | 72.6±33.5 | 75.0±27.6 | 67.6±28.6 | 68.5±30.7 | 69.5±32.3 | 57.8±26.2 | 59.9±29.9 | 60.0±22.2 | 55.1±22.9 | 49.6±26.8 | 49.3±20.6 | <0.01 | 0.05 |
| S1% | 3.8±2.9 | 4.3±4.2 | 4.1±2.8 | 4.3±4.1 | 4.5±3.0 | 4.8±3.1 | 5.2±4.0 | 5.4±4.0 | 4.9±2.9 | 4.9±3.3 | 4.8±2.2 | 6.4±3.3 | 0.02 | 0.02 |
| S2% | 54.2±7.7 | 53.6±8.5 | 53.8±8.0 | 53.0±8.2 | 55.0±9.3 | 54.1±9.6 | 54.5±9.3 | 57.4±11.6 | 55.9±8.9 | 56.7±11.2 | 55.4±12.4 | 58.2±13.1 | <0.01 | 0.02 |
| SWS% | 23.6±6.7 | 23.2±6.7 | 21.8±7.6 | 23.2±7.7 | 20.9±7.9 | 21.3±8.7 | 22.5±7.8 | 19.7±9.6 | 21.1±7.4 | 21.3±10.2 | 23.3±11.7 | 18.3±10.4 | <0.01 | 0.03 |
| REM% | 18.4±6.0 | 19.0±6.9 | 20.3±5.5 | 19.5±6.5 | 19.6±6.4 | 19.7±6.8 | 17.8±6.7 | 17.8±7.2 | 18.1±5.7 | 17.0±5.8 | 16.5±7.1 | 17.0±6.3 | <0.01 | 0.03 |

ANOVA, analysis of variance; TST, total sleep time; Eff, sleep efficiency; Lat, sleep latency; REMlat, REM sleep latency (min); WASO, wake after sleep onset; AI, arousal index; RAI, respiratory arousal index; NRAI, non-respiratory arousal index; S1d, stage 1 duration (min); S2d, stage 2 duration (min); SWSd, slow wave sleep duration (min); REMd, REM sleep duration; S1% stage 1 percentage; S2%, stage 2 percentage; SWS%, slow wave sleep percentage; REM%, REM sleep percentage.
Values are mean ± SD.
[a] η²

FIG. 12A

Table 1
Sleep structure and age

| Sleep structure | Age (years) 20-24 (n=106) | 25-29 (n=130) | 30-34 (n=129) | 35-39 (n=119) | 40-44 (n=128) | 45-49 (n=126) | 50-54 (n=87) | 55-59 (n=79) | 60-64 (n=48) | 65-69 (n=40) | 70-74 (n=26) | 75-80 (n=24) | P (one-way ANOVA) | Effect size[a] |
|---|---|---|---|---|---|---|---|---|---|---|---|---|---|---|
| TST | 376.3 ± 75.4 | 367.9 ± 78.4 | 364.0 ± 71.0 | 333.4 ± 82.9 | 338.0 ± 78.1 | 338.2 ± 74.9 | 316.9 ± 74.9 | 325.9 ± 70.9 | 329.1 ± 51.2 | 314.5 ± 80.5 | 292.0 ± 78.0 | 291.0 ± 66.0 | <0.01 | 0.08 |
| Eff | 87.9 ± 9.5 | 86.1 ± 11.8 | 86.8 ± 8.6 | 81.6 ± 15.5 | 82.5 ± 12.2 | 81.3 ± 12.5 | 78.1 ± 13.0 | 77.7 ± 11.8 | 79.0 ± 9.6 | 74.9 ± 14.5 | 72.8 ± 17.3 | 65.4 ± 13.0 | <0.01 | 0.13 |
| Lat | 13.8 ± 17.5 | 15.0 ± 20.1 | 14.5 ± 16.8 | 19.6 ± 32.7 | 13.4 ± 13.9 | 17.4 ± 21.0 | 17.8 ± 18.7 | 17.3 ± 18.3 | 17.3 ± 15.0 | 20.5 ± 28.7 | 28.7 ± 41.1 | 34.6 ± 45.9 | 0.01 | 0.03 |
| REMlat | 106.4 ± 50.9 | 97.5 ± 45.5 | 95.6 ± 44.3 | 89.8 ± 37.9 | 97.0 ± 47.5 | 102.5 ± 57.0 | 106.1 ± 58.6 | 109.8 ± 64.2 | 109.8 ± 65.4 | 95.0 ± 52.0 | 129.1 ± 83.1 | 120.9 ± 3.0 | 0.01 | 0.02 |
| WASO | 38.9 ± 35.5 | 44.4 ± 40.5 | 41.0 ± 30.2 | 55.0 ± 47.1 | 58.1 ± 45.8 | 61.0 ± 45.3 | 72.3 ± 47.7 | 78.1 ± 44.9 | 72.1 ± 37.4 | 84.1 ± 40.4 | 81.1 ± 49.2 | 121.6 ± 49.6 | <0.01 | 0.14 |
| AI | 8.8 ± 4.6 | 10.4 ± 5.8 | 11.4 ± 6.7 | 12.5 ± 7.8 | 15.3 ± 10.6 | 16.3 ± 13.3 | 19.6 ± 15.3 | 19.0 ± 11.1 | 22.3 ± 14.6 | 20.9 ± 12.4 | 17.5 ± 8.8 | 21.8 ± 13.7 | <0.01 | 0.14 |
| RAI | 1.9 ± 2.3 | 2.4 ± 3.9 | 3.3 ± 5.1 | 4.1 ± 5.3 | 5.9 ± 10.0 | 7.3 ± 11.3 | 9.0 ± 11.7 | 8.6 ± 9.4 | 13.9 ± 13.6 | 10.3 ± 9.9 | 9.6 ± 8.7 | 13.3 ± 15.2 | <0.01 | 0.13 |
| NRAI | 7.1 ± 3.4 | 7.9 ± 3.8 | 8.2 ± 4.1 | 8.5 ± 5.1 | 9.4 ± 6.4 | 9.1 ± 5.3 | 10.7 ± 7.4 | 10.4 ± 6.3 | 8.9 ± 5.4 | 10.8 ± 8.3 | 8.1 ± 4.7 | 8.5 ± 5.2 | <0.01 | 0.04 |
| S1d | 13.6 ± 9.6 | 14.3 ± 10.0 | 14.5 ± 8.8 | 12.7 ± 8.2 | 14.9 ± 10.7 | 16.0 ± 10.3 | 16.2 ± 13.0 | 17.3 ± 13.2 | 15.9 ± 9.4 | 13.7 ± 5.3 | 13.3 ± 6.6 | 18.2 ± 10.1 | 0.05 | 0.02 |
| S2d | 204.4 ± 52.1 | 197.4 ± 49.1 | 197.0 ± 54.6 | 177.7 ± 53.7 | 184.7 ± 49.7 | 181.9 ± 48.4 | 172.6 ± 47.3 | 165.4 ± 51.2 | 184.0 ± 38.5 | 178.4 ± 56.1 | 165.7 ± 61.0 | 169.9 ± 58.4 | <0.01 | 0.04 |
| SWSd | 87.4 ± 26.5 | 63.7 ± 25.3 | 77.5 ± 25.9 | 75.4 ± 26.3 | 69.9 ± 28.9 | 70.7 ± 30.0 | 70.2 ± 25.2 | 63.4 ± 31.5 | 69.3 ± 26.5 | 67.2 ± 37.3 | 63.3 ± 27.0 | 53.6 ± 33.2 | <0.01 | 0.07 |
| REMd | 70.9 ± 30.5 | 72.6 ± 33.5 | 75.0 ± 27.6 | 67.6 ± 28.6 | 68.5 ± 30.7 | 69.5 ± 32.3 | 57.8 ± 26.2 | 59.9 ± 29.9 | 60.0 ± 22.2 | 55.1 ± 22.9 | 49.6 ± 26.8 | 49.3 ± 20.6 | <0.01 | 0.05 |
| S1% | 3.8 ± 2.9 | 4.3 ± 4.2 | 4.1 ± 2.8 | 4.3 ± 4.1 | 4.5 ± 3.0 | 4.8 ± 3.1 | 5.2 ± 4.0 | 5.4 ± 4.0 | 4.9 ± 2.9 | 4.9 ± 3.3 | 4.8 ± 2.2 | 6.4 ± 3.3 | <0.01 | 0.02 |
| S2% | 54.2 ± 7.7 | 53.6 ± 8.5 | 53.8 ± 8.0 | 53.0 ± 8.2 | 55.0 ± 9.3 | 54.1 ± 9.6 | 54.5 ± 9.3 | 57.4 ± 11.6 | 55.9 ± 8.9 | 56.7 ± 11.2 | 55.4 ± 12.4 | 58.2 ± 13.1 | <0.01 | 0.02 |
| SWS% | 23.6 ± 6.7 | 23.2 ± 6.7 | 21.8 ± 6.7 | 23.2 ± 7.7 | 20.9 ± 7.9 | 21.3 ± 8.7 | 22.5 ± 7.8 | 19.7 ± 9.6 | 21.1 ± 7.4 | 21.3 ± 10.2 | 23.3 ± 11.7 | 18.3 ± 10.4 | <0.01 | 0.02 |
| REM% | 18.4 ± 6.0 | 19.0 ± 6.9 | 20.3 ± 5.5 | 19.5 ± 6.5 | 19.6 ± 6.4 | 19.7 ± 6.8 | 17.8 ± 6.7 | 17.8 ± 7.2 | 18.1 ± 5.7 | 17.0 ± 5.8 | 16.5 ± 7.1 | 17.0 ± 6.3 | <0.01 | 0.03 |

ANOVA, analysis of variance; TST, total sleep time; Eff, sleep efficiency; Lat, sleep latency; REMlat, REM sleep latency; WASO, wake after sleep onset; AI, arousal index; RA1, respiratory arousal index; NRAI, non-respiratory arousal index; S1d, stage 1 duration (min); S2d, stage 2 duration (min); SWSd, skw wave sleep duration (min); REMd, REM sleep duration (min); S1% stage 1 percentage; S2%, stage 2 percentage; SWS%, skw wave sleep percentage; REM%, REM sleep percentage.
Values are mean ± SD.
[a] η².

FIG. 13A

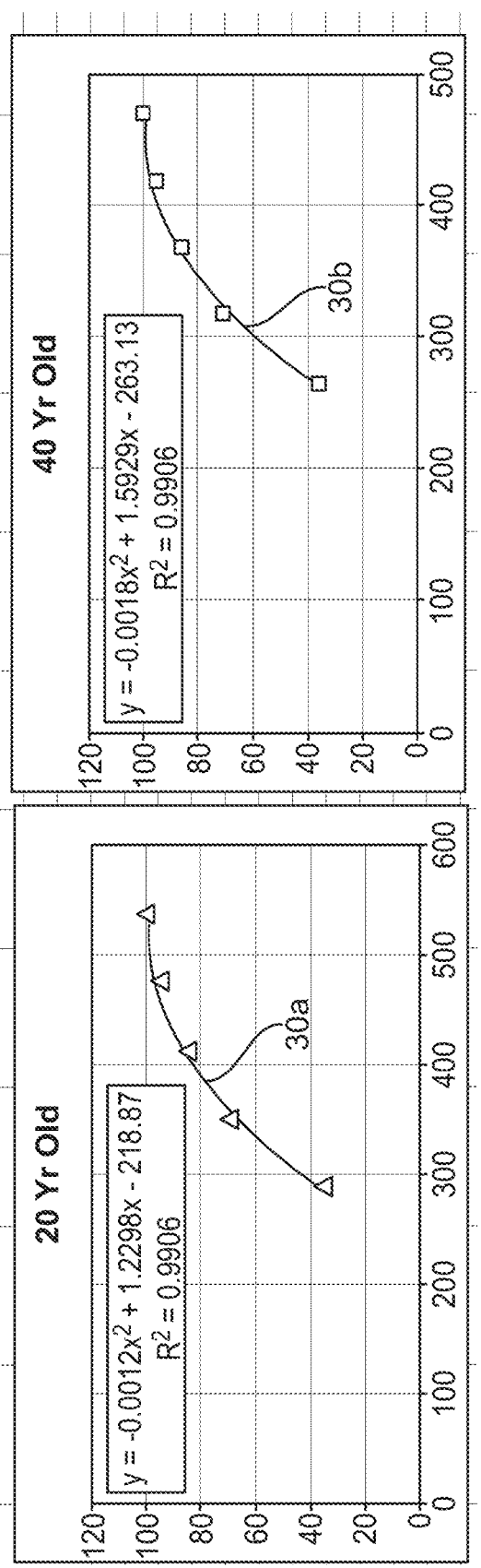

Total Sleep Time Scoring

| Calculated Hrs | x-axis minutes | 20 y/o | 40 y/o | 60 y/o | 80 y/o |
|---|---|---|---|---|---|
| 0 | 0 | 0 | 0 | 0 | 0 |
| 0.8 | 50 | 0 | 0 | 0 | 0 |
| 1.7 | 100 | 0 | 0 | 0 | 0 |
| 2.5 | 150 | 0 | 0 | 0 | 0 |
| 3.3 | 200 | 0 | 0 | 3.48 | 20.63 |
| 4.2 | 250 | 13.58 | 22.595 | 38.95 | 52.81 |
| 5.0 | 300 | 42.07 | 52.74 | 65.92 | 75.49 |
| 5.8 | 350 | 64.56 | 73.885 | 84.39 | 88.67 |
| 6.7 | 400 | 81.05 | 86.03 | 94.36 | 97 |
| 7.5 | 450 | 91.54 | 95 | 98 | 100 |
| 8.3 | 500 | 96.03 | 99 | 100 | 100 |
| 9.2 | 550 | 100 | 100 | 100 | 100 |

Equations 20 yr old  $y = -0.0012x^2 + 1.2298x - 218.87$
40 yr old  $y = -0.0018x^2 + 1.5929x - 263.13$
60 yr old  $y = -0.0017x^2 + 1.4744x - 223.4$
80 yr old  $y = -0.0019x^2 + 1.4986x - 203.09$ Table 1
Sleep structure and age

| Sleep structure | Age (years) 20-24 (n=106) | 25-29 (n=130) | 30-34 (n=129) | 35-39 (n=119) | 40-44 (n=128) | 45-49 (n=126) | 50-54 (n=87) | 55-59 (n=79) | 60-64 (n=48) | 65-69 (n=40) | 70-74 (n=26) | 75-80 (n=24) | P (one-way ANOVA) | Effect size² |
|---|---|---|---|---|---|---|---|---|---|---|---|---|---|---|
| TST | 376.3±75.4 | 367.9±76.4 | 364.0±71.0 | 333.4±82.9 | 338.0±78.1 | 338.2±74.9 | 316.9±74.9 | 325.9±70.9 | 329.1±51.2 | 314.5±80.5 | 292.0±78.0 | 291.0±66.0 | <0.01 | 0.08 |
| Eff | 87.9±9.5 | 86.1±11.8 | 86.8±8.6 | 81.6±15.5 | 82.5±12.2 | 81.3±12.5 | 78.1±13.0 | 77.7±11.8 | 79.0±9.6 | 74.9±14.5 | 72.8±17.3 | 65.4±13.0 | <0.01 | 0.13 |
| Lat | 13.8±17.5 | 15.0±20.1 | 14.5±16.8 | 19.6±32.7 | 13.4±13.9 | 17.4±21.0 | 17.8±18.7 | 17.3±18.3 | 17.3±15.0 | 20.5±28.7 | 28.7±41.1 | 34.6±45.9 | 0.01 | 0.03 |
| REMlat | 106.4±50.9 | 97.5±45.5 | 95.6±44.3 | 89.8±37.9 | 97.0±47.5 | 102.5±57.0 | 106.1±58.6 | 109.8±64.2 | 109.8±65.4 | 95.0±52.0 | 129.1±83.1 | 120.9±3.0 | 0.01 | 0.02 |
| WASO | 38.9±35.5 | 44.4±40.5 | 41.0±30.2 | 55.0±47.1 | 56.1±45.8 | 61.0±45.3 | 72.3±47.7 | 78.1±44.9 | 72.1±37.4 | 84.1±40.4 | 81.1±49.2 | 121.6±49.6 | <0.01 | 0.14 |
| AI | 8.8±4.6 | 10.4±5.8 | 11.4±6.7 | 12.5±7.8 | 15.3±10.6 | 16.3±13.3 | 19.6±15.3 | 19.0±11.1 | 22.3±14.6 | 20.9±12.4 | 17.5±8.8 | 21.8±13.7 | <0.01 | 0.14 |
| RAI | 1.9±2.3 | 2.4±3.9 | 3.3±5.1 | 4.1±5.3 | 5.9±10.0 | 7.3±11.3 | 9.0±11.7 | 8.6±9.4 | 13.9±13.6 | 10.3±9.9 | 9.6±8.7 | 13.3±15.2 | <0.01 | 0.13 |
| NRAI | 7.1±3.4 | 7.9±3.8 | 8.2±4.1 | 8.5±5.1 | 9.4±6.4 | 9.1±5.3 | 10.7±7.4 | 10.4±6.3 | 8.9±5.4 | 10.8±8.3 | 8.1±4.7 | 8.5±5.2 | <0.01 | 0.04 |
| S1d | 13.6±9.6 | 14.3±10.0 | 14.5±8.8 | 12.7±8.2 | 14.9±10.7 | 16.0±10.3 | 16.2±13.0 | 17.3±13.2 | 15.9±9.4 | 13.7±5.3 | 13.3±6.6 | 18.2±10.1 | 0.05 | 0.02 |
| S2d | 204.4±52.1 | 197.4±49.1 | 197.0±54.6 | 177.7±53.7 | 184.7±49.7 | 181.9±48.4 | 172.6±47.3 | 185.4±51.2 | 184.0±38.5 | 178.4±56.1 | 165.7±61.0 | 169.9±58.4 | <0.01 | 0.04 |
| SWSd | 87.4±26.5 | 63.7±25.3 | 77.5±25.9 | 75.4±26.3 | 69.9±28.9 | 70.7±30.0 | 70.2±25.2 | 63.4±31.5 | 69.3±26.5 | 67.2±37.3 | 63.3±27.0 | 53.6±33.2 | <0.01 | 0.07 |
| REMd | 70.9±30.5 | 72.6±33.5 | 75.0±27.6 | 67.6±28.6 | 68.5±30.7 | 69.5±32.3 | 57.8±26.2 | 59.9±29.9 | 60.0±22.2 | 55.1±22.9 | 49.6±26.6 | 49.3±20.6 | <0.01 | 0.05 |
| S1% | 3.8±2.9 | 4.3±4.2 | 4.1±2.8 | 4.3±4.1 | 4.5±3.0 | 4.8±3.1 | 5.2±4.0 | 5.4±4.0 | 4.9±2.9 | 4.9±3.3 | 4.8±2.2 | 6.4±3.3 | <0.01 | 0.02 |
| S2% | 54.2±7.7 | 53.6±8.5 | 53.8±8.0 | 53.0±8.2 | 55.0±9.3 | 54.1±9.6 | 54.5±9.3 | 57.4±11.6 | 55.9±8.9 | 56.7±11.2 | 55.4±12.4 | 58.2±13.1 | <0.01 | 0.02 |
| SWS% | 23.6±6.7 | 23.2±6.7 | 21.8±7.6 | 23.2±7.7 | 20.9±7.9 | 21.3±8.7 | 22.5±7.8 | 19.7±9.6 | 21.1±7.4 | 21.3±10.2 | 23.3±11.7 | 18.3±10.4 | <0.01 | 0.03 |
| REM% | 18.4±6.0 | 19.0±6.9 | 20.3±5.5 | 19.5±6.5 | 19.6±6.4 | 19.7±6.8 | 17.8±6.7 | 17.8±7.2 | 18.1±5.7 | 17.0±5.8 | 16.5±7.1 | 17.0±6.3 | <0.01 | 0.03 |

ANOVA, analysis of variance; TST, total sleep time; Eff, sleep efficiency; Lat, sleep latency; REMlat, REM sleep latency (min); WASO, wake after sleep onset; AI, arousal index; RAI, respiratory arousal index; NRAI, non-respiratory arousal index; S1d, stage 1 duration (min); S2d, stage 2 duration (min); SWSd, skw wave sleep duration (min); REMd, REM sleep duration (min); S1% stage 1 percentage; S2%, stage 2 percentage; SWS%, skw wave sleep percentage; REM%, REM sleep percentage.
Values are mean ± SD.
a η².

FIG. 17A

Total Deep Sleep Scoring
Equations

| Age | Equation |
|---|---|
| 20 yr old | $y = -0.0063x^2 + 1.9255x - 46.537$ |
| 40 yr old | $y = -0.0086x^2 + 1.9353x - 8.121$ |
| 60 yr old | $y = -0.0123x^2 + 2.2326x$ |
| 80 yr old | $y = -0.0144x^2 + 2.425x$ |

| Deep Sleep minute: | 20 y/o | 40 y/o | 60 y/o | 80 y/o |
|---|---|---|---|---|
| 0 | 0 | 0 | 0 | 0 |
| 10 | 0 | 10 | 21 | 23 |
| 20 | 0 | 27 | 40 | 43 |
| 30 | 6 | 42 | 56 | 60 |
| 40 | 20 | 56 | 70 | 74 |
| 50 | 34 | 67 | 81 | 85 |
| 60 | 46 | 77 | 90 | 94 |
| 70 | 57 | 85 | 96 | 99 |
| 80 | 67 | 92 | 100 | 100 |
| 90 | 76 | 96 | 100 | 100 |
| 100 | 83 | 99 | 100 | 100 |
| 110 | 89 | 100 | 100 | 100 |
| 120 | 94 | 100 | 100 | 100 |
| 130 | 97 | 100 | 100 | 100 |
| 140 | 100 | 100 | 100 | 100 |

Table 1
Sleep structure and age

| Sleep structure | Age (years) | | | | | | | | | | | P (one-way ANOVA) | Effect size[a] |
|---|---|---|---|---|---|---|---|---|---|---|---|---|---|
| | 20-24 (n=106) | 25-29 (n=130) | 30-34 (n=129) | 35-39 (n=119) | 40-44 (n=128) | 45-49 (n=126) | 50-54 (n=87) | 55-59 (n=79) | 60-64 (n=48) | 65-69 (n=40) | 70-74 (n=26) | 75-80 (n=24) | | |
| TST | 376.3±75.4 | 367.9±76.4 | 364.0±71.0 | 333.4±82.9 | 338.0±78.1 | 338.2±74.9 | 316.9±69.3 | 325.9±70.9 | 329.1±51.2 | 314.5±80.5 | 292.0±78.0 | 291.0±66.0 | <0.01 | 0.08 |
| Eff | 87.9±9.5 | 86.1±11.8 | 86.8±8.6 | 81.6±15.5 | 82.5±12.2 | 81.3±12.5 | 78.1±12.7 | 77.7±11.8 | 79.0±9.6 | 74.9±14.5 | 72.8±17.3 | 65.4±13.0 | <0.01 | 0.13 |
| Lat | 13.8±17.5 | 15.0±20.1 | 14.5±16.8 | 19.6±32.7 | 13.4±13.9 | 17.4±21.0 | 17.8±18.7 | 17.3±18.3 | 17.3±15.0 | 20.5±28.7 | 28.7±41.1 | 34.6±45.9 | 0.01 | 0.03 |
| REMlat | 106.4±50.9 | 97.5±45.5 | 95.6±44.3 | 89.8±37.9 | 97.0±47.5 | 102.5±57.0 | 106.1±45.3 | 109.8±64.2 | 109.8±65.4 | 95.0±52.0 | 129.1±83.1 | 120.9±3.0 | 0.01 | 0.02 |
| WASO | 38.9±35.5 | 44.4±40.5 | 41.0±30.2 | 55.0±47.1 | 58.1±45.8 | 61.0±45.3 | 72.3±47.7 | 78.1±44.9 | 72.1±37.4 | 84.1±40.4 | 81.1±49.2 | 121.6±49.6 | <0.01 | 0.14 |
| AI | 8.8±4.6 | 10.4±5.8 | 11.4±6.7 | 12.5±7.8 | 15.3±10.6 | 16.3±13.3 | 19.6±15.3 | 19.0±11.1 | 22.3±14.6 | 20.9±12.4 | 17.5±8.8 | 21.8±13.7 | <0.01 | 0.14 |
| RAI | 1.9±2.3 | 2.4±3.9 | 3.3±5.1 | 4.1±5.3 | 5.9±10.0 | 7.3±11.3 | 9.0±11.7 | 8.6±9.4 | 13.9±13.6 | 10.3±9.9 | 9.6±8.7 | 13.3±15.2 | <0.01 | 0.13 |
| NRAI | 7.1±3.4 | 7.9±3.8 | 8.2±4.1 | 8.5±5.1 | 9.4±6.4 | 9.1±5.3 | 10.7±7.4 | 10.4±6.3 | 8.9±5.4 | 10.8±8.3 | 8.1±4.7 | 8.5±5.2 | <0.01 | 0.04 |
| S1d | 13.6±9.6 | 14.3±10.0 | 14.5±8.8 | 12.7±8.2 | 14.9±10.7 | 16.0±10.3 | 16.2±13.0 | 17.3±13.2 | 15.9±9.4 | 13.7±5.3 | 13.3±6.6 | 18.2±10.1 | 0.05 | 0.02 |
| S2d | 204.4±52.1 | 197.4±49.1 | 197.0±54.6 | 177.7±53.7 | 184.7±49.7 | 181.9±48.4 | 172.6±47.3 | 185.4±51.2 | 184.0±38.5 | 178.4±56.1 | 165.7±61.0 | 169.9±58.4 | <0.01 | 0.04 |
| SWSd | 87.4±26.5 | 63.7±25.3 | 77.5±25.9 | 75.4±26.3 | 69.9±28.9 | 70.7±30.0 | 70.2±25.2 | 63.4±31.5 | 69.3±28.5 | 67.2±37.3 | 63.3±27.0 | 53.6±33.2 | <0.01 | 0.07 |
| REMd | 70.9±30.5 | 72.6±33.5 | 75.0±27.6 | 67.6±28.6 | 68.5±30.7 | 69.5±32.3 | 57.8±26.2 | 59.9±29.9 | 60.0±22.2 | 55.1±22.9 | 49.6±26.8 | 49.3±20.6 | <0.01 | 0.05 |
| S1% | 3.8±2.9 | 4.3±4.2 | 4.1±2.8 | 4.3±4.1 | 4.5±3.0 | 4.8±3.1 | 5.2±4.0 | 5.4±4.0 | 4.9±2.9 | 4.9±3.3 | 4.8±2.2 | 6.4±3.3 | <0.01 | 0.02 |
| S2% | 54.2±7.7 | 53.6±8.5 | 53.8±8.0 | 53.0±8.2 | 55.0±9.3 | 54.1±9.6 | 54.5±9.3 | 57.4±11.6 | 55.9±8.9 | 56.7±11.2 | 55.4±12.4 | 58.2±13.1 | <0.01 | 0.02 |
| SWS% | 23.6±6.7 | 23.2±6.7 | 21.8±7.6 | 23.2±7.7 | 20.9±7.9 | 21.3±8.7 | 22.5±7.8 | 19.7±9.5 | 21.1±7.4 | 21.3±10.2 | 23.3±11.7 | 18.3±10.4 | <0.01 | 0.03 |
| REM% | 18.4±6.0 | 19.0±6.9 | 20.3±5.5 | 19.5±6.5 | 19.6±6.4 | 19.7±6.6 | 17.8±6.7 | 17.8±7.2 | 18.1±5.7 | 17.0±5.8 | 16.5±7.1 | 17.0±6.3 | <0.01 | 0.03 |

ANOVA, analysis of variance; TST, total sleep time; Eff, sleep efficiency; Lat, sleep latency; REMlat, REM sleep latency (min); WASO, wake after sleep onset; AI, arousal index; RAI, respiratory arousal index; NRAI, non-respiratory arousal index; S1d, stage 1 duration (min); S2d, stage 2 duration (min); SWSd, skw wave sleep duration (min); REMd, REM sleep duration (min); S1% stage 1 percentage; S2%, stage 2 percentage; SWS%, skw wave sleep percentage; REM%, REM sleep percentage.
Values are mean ± SD.
[a] η².

FIG. 21

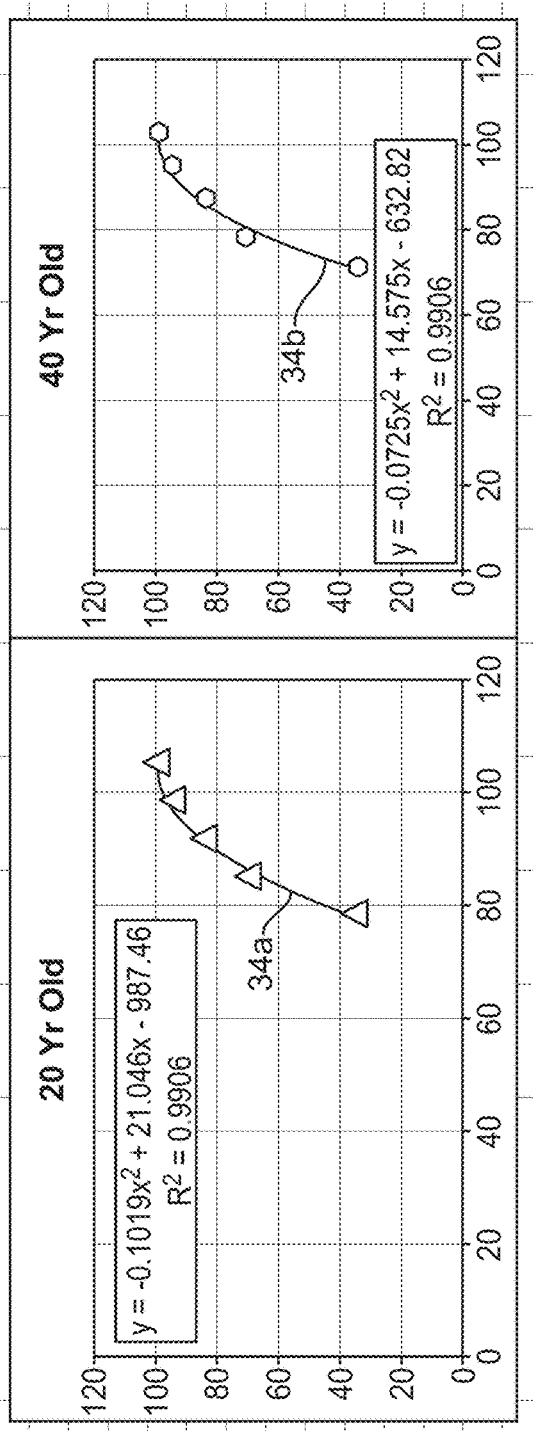

|  | 60 y/o | | | 80 y/o | | |
|---|---|---|---|---|---|---|
|  | Moraes | Ohayon | NG SCORES | Moraes | Ohayon | NG SCORES |
| Average Sleep Effience | 76 | 85.5 | 80.75 | 65 | 77 | 71 |
| Stnd Dev | 12 | 5 | 8.5 | 13 | 6 | 9.5 |
| Stnd Dev % | 16% | 6% | 11% | 20% | 8% | 13% |
| Avg |  |  | 80.75 |  |  | 71 |
| Avg + 1 SD |  |  | 89.25 |  |  | 80.5 |
| Avg + 2 SD |  |  | 97.75 |  |  | 90 |
| Avg - 1 SD |  |  | 72.25 |  |  | 61.5 |
| Avg - 2 SD |  |  | 63.75 |  |  | 52 |
| | | | 85 | | | 85 |
| | | | 95 | | | 95 |
| | | | 100 | | | 100 |
| | | | 70 | | | 70 |
| | | | 35 | | | 35 |

Sleep Efficiency Scoring Equations 20 yr old   $y = -0.1019x^2 + 21.046x - 987.46$
40 yr old   $y = -0.0725x^2 + 14.575x - 632.82$
60 yr old   $y = -0.0643x^2 + 12.202x - 479.98$
80 yr old   $y = -0.0514x^2 + 8.9367x - 288.89$

| Deep Sleep r | 20 y/o | 40 y/o | 60 y/o | 80 y/o |
|---|---|---|---|---|
| 0 | 0 | 0 | 0 | 0 |
| 10 | 0 | 0 | 0 | 0 |
| 20 | 0 | 0 | 0 | 0 |
| 30 | 0 | 0 | 0 | 0 |
| 40 | 0 | 0 | 0 | 0 |
| 50 | 0 | 0 | 0 | 29 |
| 60 | 0 | 0 | 21 | 62 |
| 70 | 0 | 32 | 59 | 85 |
| 80 | 44 | 69 | 85 | 97 |
| 90 | 81 | 92 | 97 | 99 |
| 100 | 98 | 100 | 100 | 100 |
| 110 | 100 | 100 | 100 | 100 |
| 120 | 100 | 100 | 100 | 100 |
| 130 | 100 | 100 | 100 | 100 |
| 140 | 100 | 100 | 100 | 100 |

Averages and Standard Deviations for Longest Deep Sleep
|  | NG | SCORES |
|---|---|---|
| Average Duration Deep Sleep | 40 | 85 |
| Stnd Dev | 32 |  |
| Stnd Dev % | 80% |  |
|  |  |  |
| Avg | 40 | 85 |
| Avg + 1 SD | 72 | 95 |
| Avg + 2 SD | 104 | 100 |
| Avg - 1 SD | 24 | 50 |
| Avg - 2 SD | 10 | 15 |
FIG. 24A
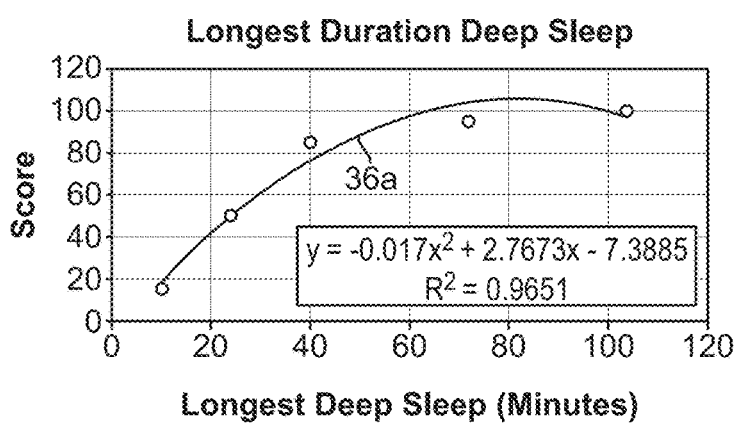
FIG. 24B
Longest Deep Sleep Scoring
$y = -0.017x^2 + 2.7673x - 7.3885$
| | |
|---|---|
| 0 | 0 |
| 10 | 19 |
| 20 | 41 |
| 30 | 60 |
| 40 | 76 |
| 50 | 88 |
| 60 | 97 |
| 70 | 100 |
| 80 | 100 |
| 90 | 100 |
| 100 | 100 |
FIG. 24C
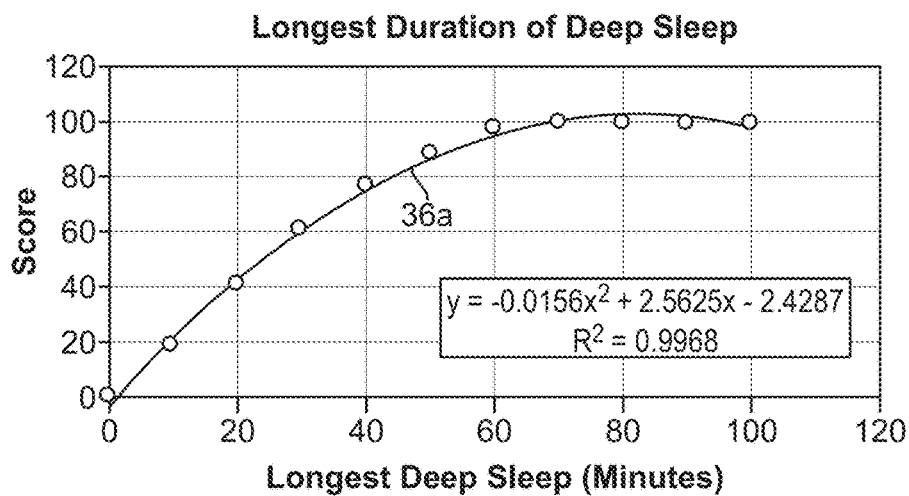
FIG. 24D Averages and Standard Deviations for Deep Sleep Strength
|  | NG | SCORES |
|---|---|---|
| Average Strength Deep Sleep | 1.23 | 85 |
| Stnd Dev | 0.32 | |
| Stnd Dev % | 26% | |
| Avg power spectral density | 1.23 | 85 |
| Avg + 1 SD | 1.55 | 95 |
| Avg + 2 SD | 1.87 | 100 |
| Avg - 1 SD | 1.07 | 70 |
| Avg - 2 SD | 0.91 | 35 |
FIG. 25A
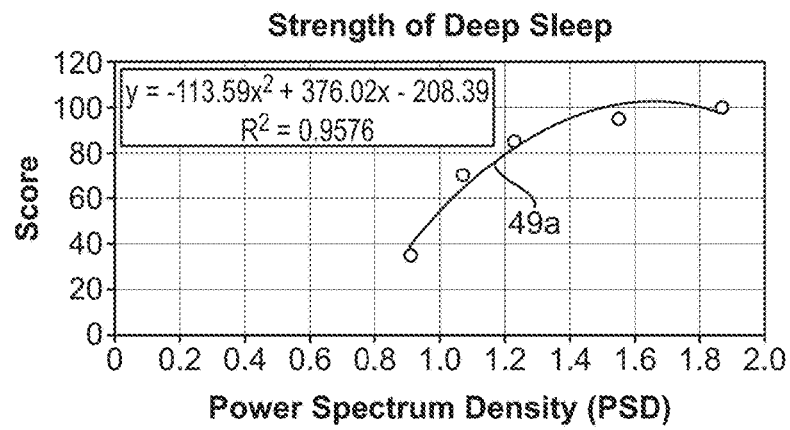
FIG. 25B
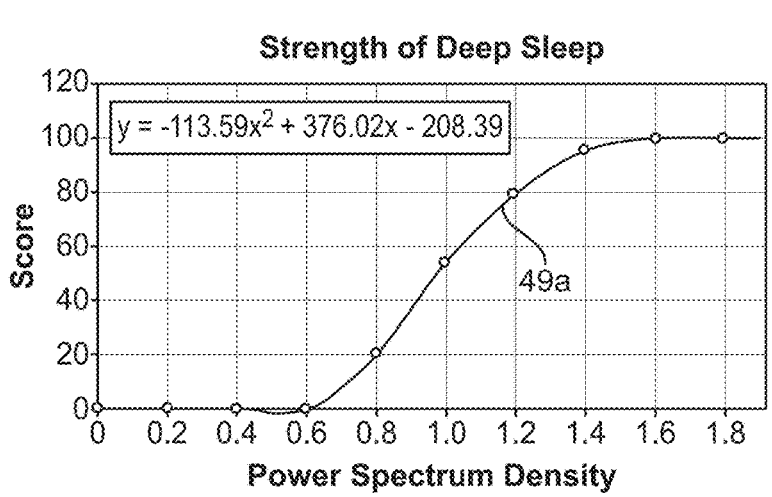
FIG. 25C
Deep Sleep Strength Scoring
| PSD | Score |
|---|---|
| 0 | 0 |
| 0.2 | 0 |
| 0.4 | 0 |
| 0.6 | 0 |
| 0.8 | 20 |
| 1 | 54 |
| 1.2 | 79 |
| 1.4 | 95 |
| 1.6 | 100 |
| 1.8 | 100 |
| 2 | 100 |
$y = -113.59x^2 + 376.02x - 208.39$
FIG. 25D Table 4. Gender Effects on 24-h Heart Rate Variability and Heart Rate for Four Age Groups

| Age (yr) and Gender | SDNN (ms) | SDANN (ms) | SDNN Index (ms) | rMSSD (ms) | pNN50 (%) | HR (beats/min) |
|---|---|---|---|---|---|---|
| 10-29 | | | | | | |
| M | *[182 ± 35 | *[162 ± 33 | *[88 ± 20 | *[53 ± 18 | *[26 ± 13 | *[76 ± 10 |
| F | [147 ± 43 | [133 ± 42 | [66 ± 18 | [43 ± 18 | [17 ± 12 | [83 ± 8 |
| 30-49 | | | | | | |
| M | *[146 ± 30† | *[131 ± 31† | *[65 ± 14† | 34 ± 13† | 13 ± 10† | *[76 ± 7 |
| F | [129 ± 30 | [114 ± 31 | [58 ± 13 | 31 ± 10† | 10 ± 7† | [79 ± 7 |
| 50-69 | | | | | | |
| M | 117 ± 30†‡ | 104 ± 28†‡ | 46 ± 18†‡ | 22 ± 8†‡ | 4 ± 5†‡ | 78 ± 11 |
| F | 125 ± 29 | 114 ± 29 | 49 ± 11† | 25 ± 7† | 5 ± 4† | 74 ± 10† |
| 70-99 | | | | | | |
| M | 123 ± 24† | 109 ± 28† | 43 ± 12†‡ | 22 ± 5†‡ | 3 ± 2†‡ | 72 ± 11 |
| F | 114 ± 23† | 102 ± 22† | 38 ± 10†‡ | 22 ± 8†‡ | 4 ± 4†‡ | 73 ± 8†‡ |

*$p < 0.05$, male (M) versus female (F) in same age range. †$p < 0.05$, other groups versus age range 10 to 29 years for same gender. ‡$p < 0.05$, other groups versus age range 30 to 49 years for same gender. Data presented are mean value ± SD. Other abbreviations as in Table 2.

FIG. 26A

| Age Range | Gender | rMSSD |
|---|---|---|
| 18-25 | Male | 86.5 |
| | Female | 68.7 |
| 25-35 | Male | 66.0 |
| | Female | 55.7 |
| 35-45 | Male | 50.4 |
| | Female | 45.6 |
| 45-55 | Male | 39.6 |
| | Female | 41.7 |
| 55-65 | Male | 32.1 |
| | Female | 32.5 |
| 65-75 | Male | 30.6 |
| | Female | 24.8 |
| 75+ | Male | 33.1 |
| | Female | 25.5 |

FIG. 26B

Average rSMMD by age/gender/athletic

| | | Athlete | | Non Athlete | |
|---|---|---|---|---|---|
| | Age | M -A | F -A | M -NA | F -NA |
| 18-25 | 20 | 86.5 | 68.7 | 53 | 43 |
| 25-35 | 30 | 66 | 55.7 | 41 | 37 |
| 35-45 | 40 | 50.4 | 45.6 | 35 | 32 |
| 45-55 | 50 | 39.6 | 41.7 | 30 | 28 |
| 55-65 | 60 | 32 | 32.5 | 24 | 26 |
| 65-75 | 70 | 30.6 | 24.8 | 23 | 24 |
| 75-85 | 80 | 33.1 | 25.5 | 21 | 22 |
| | | from elite | | from umetani | |

FIG. 26C

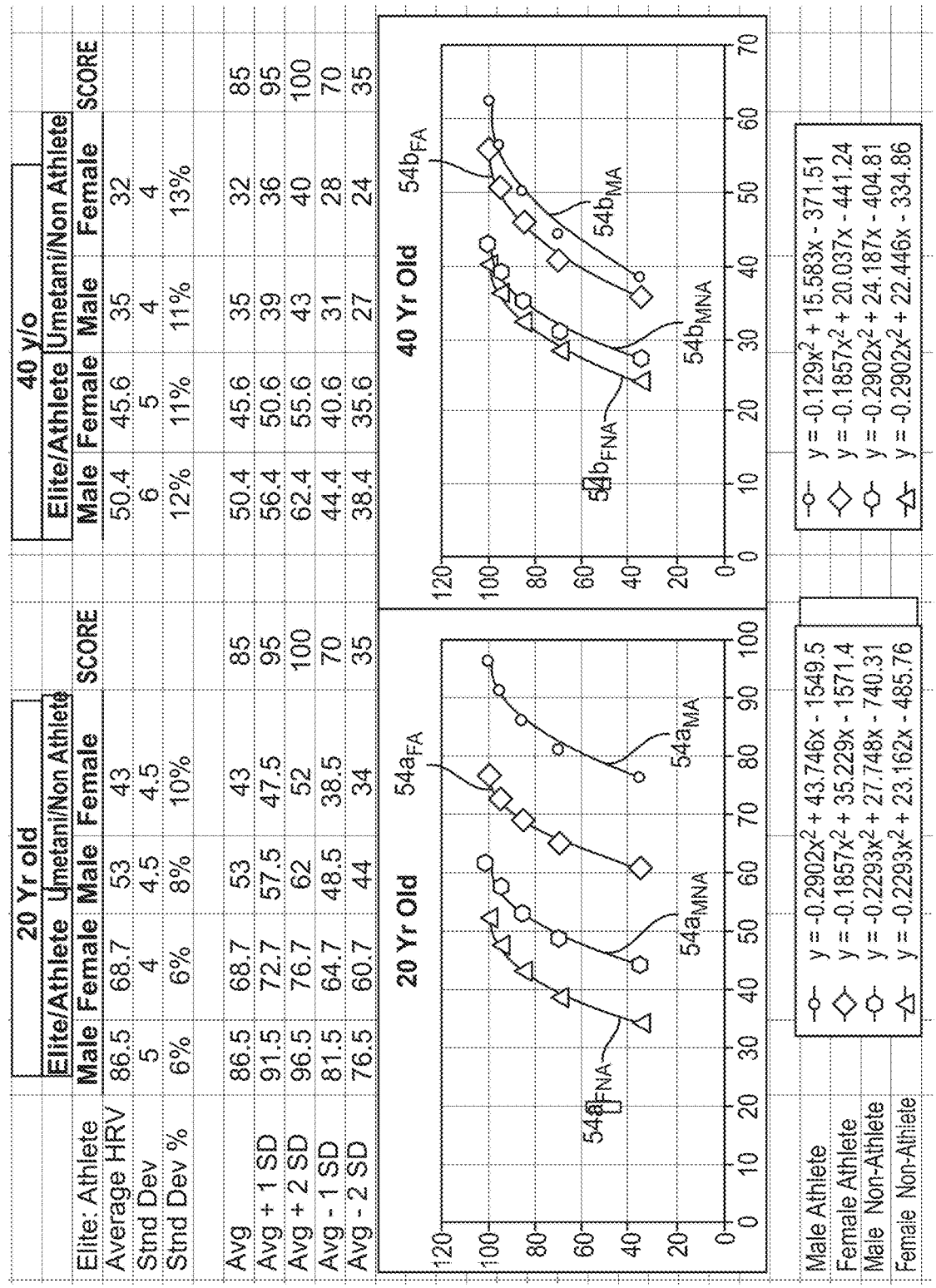

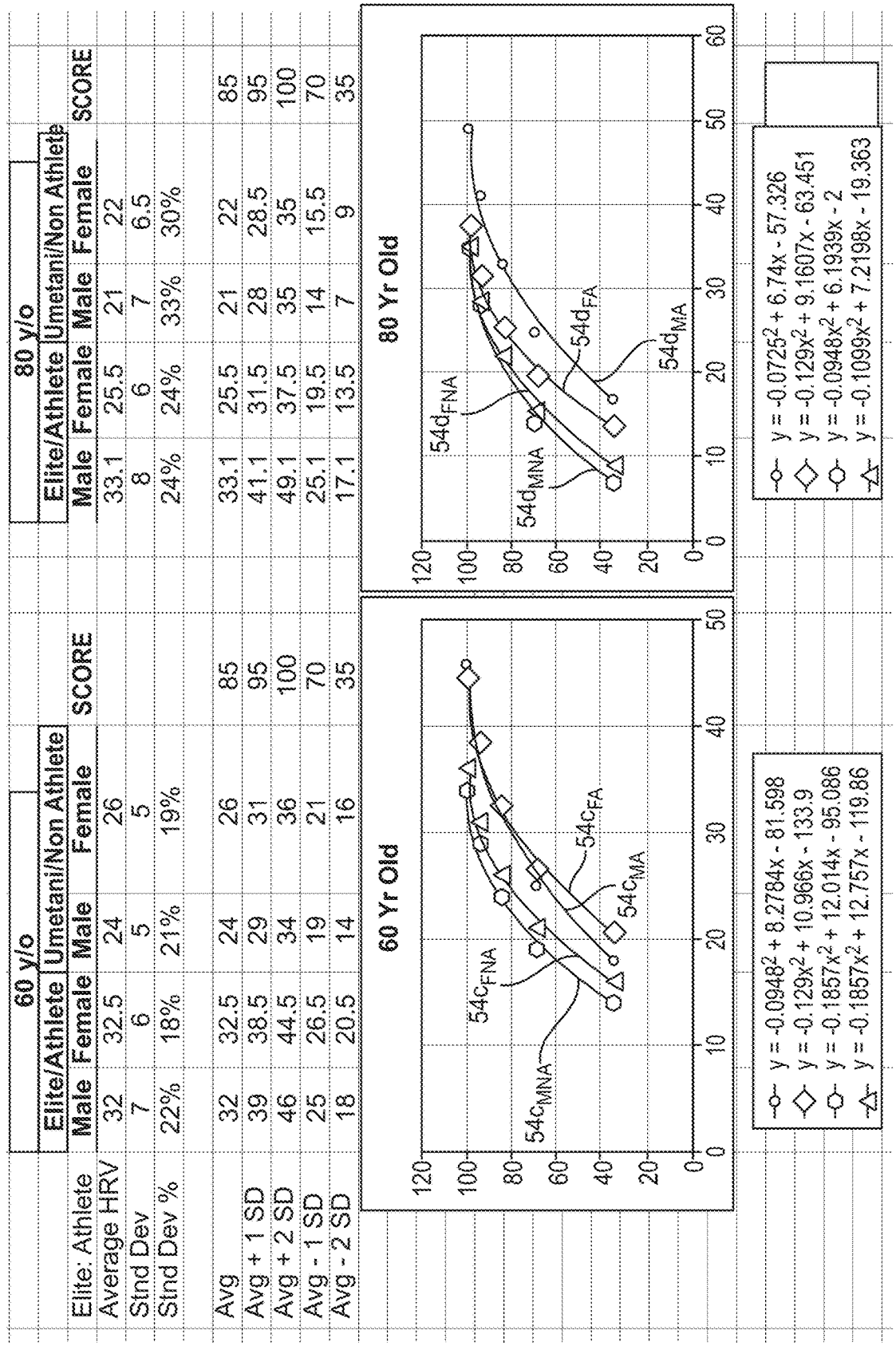

FIG. 30A
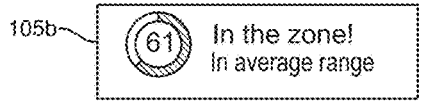
FIG. 30B
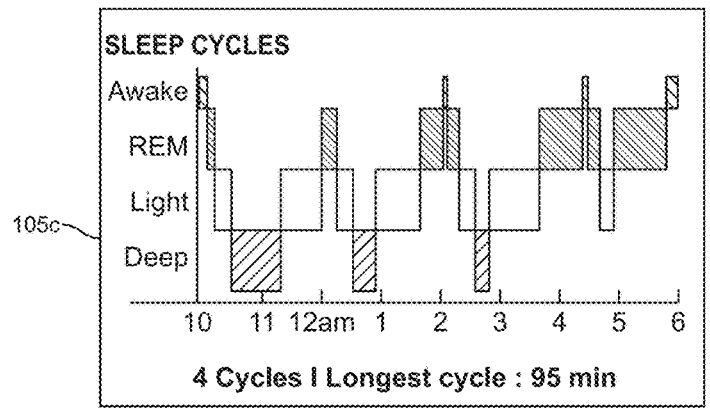
FIG. 30C
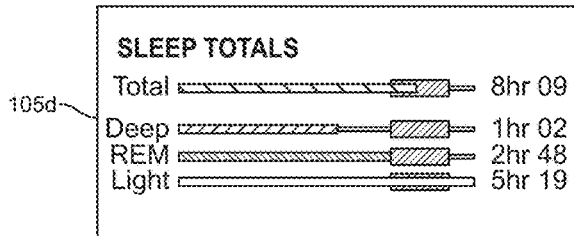
FIG. 30D
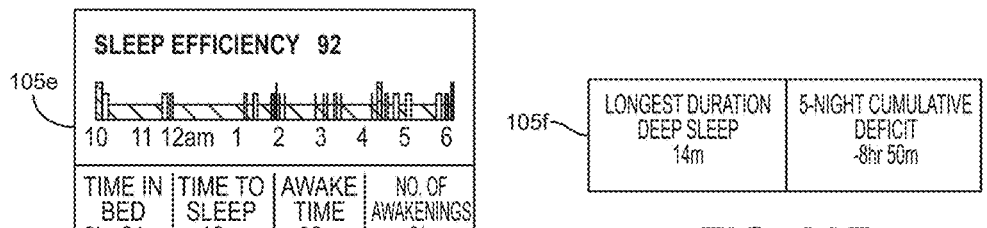
FIG. 30E
FIG. 30F

SLEEP PERFORMANCE SYSTEM AND METHOD OF USE

CROSS-REFERENCE TO RELATED APPLICATIONS

This application claims priority to U.S. Provisional Patent Application No. 62/568,249, filed on Oct. 4, 2017 and U.S. Provisional Patent Application No. 62/661,932, filed on Apr. 24, 2018, the contents of which are incorporated herein by reference in their entireties.

BACKGROUND

1. Technical Field

This disclosure relates generally to the field of sleep performance and more specifically to systems and methods that can improve the quality of sleep.

2. Background of the Art

Inadequate sleep is a public health problem. An estimated 70 million Americans suffer from chronic sleep disorders.

Insufficient sleep can impact every aspect of a person's health. For example, insufficient sleep can lead to serious health issues, including Alzheimer's, heart disease, and cancer. Insufficient sleep can also reduce cognitive and physical performance and contribute to stress.

Previous efforts to improve sleep have focused on increasing sleep quantity, but not on sleep quality. However, sleep quality—which is associated with deep sleep—is just as important as quantity, as deep sleep is critical for brain and body repair and recovery. Further, current sleep aids that focus on sleep quantity often have counterproductive side effects that actually impair sleep quality. Current sleep aids not only do not provide an objective measure of sleep improvement other than overall quantity, they also fail to positively influence deep sleep.

A need therefore exists to address this deficiency by developing a solution that can accurately monitor sleep and provide objective and trackable measures of sleep performance such as sleep quality, and more specifically, of deep sleep quality. Current sleep aids also further demonstrate that a need exists for a solution that can specifically target deep sleep quality and improve it.

BRIEF SUMMARY

This disclosure relates generally to sleep performance systems and methods of use that can improve sleep quality.

More specifically, systems and methods for increasing the quality and quantity of slow-wave sleep are disclosed.

The systems disclosed can include sleep monitoring systems. For example, systems are disclosed that can include one or more electroencephalography (EEG) electrodes configured to measure a user's brain activity during sleep. The systems can include a processor configured to quantify the quality of the user's slow-wave sleep by determining one or more sleep performance scores associated with the measured brain activity.

The methods disclosed can include methods for quantifying the quality of a user's sleep. For example, methods are disclosed that can include measuring, via one or more electroencephalography (EEG) biosensors, a user's brain activity during sleep. The methods can include quantifying, via a computer system, a quality of the user's slow-wave sleep by determining one or more sleep performance scores associated with the measured brain activity.

The methods disclosed can include methods for quantifying the quality of a user's sleep. For example, methods are disclosed that can include measuring, via one or more electroencephalography (EEG) sensors, a user's brain activity during sleep. The methods can include determining, via a computer system, one or more parameters associated with the measured brain activity. The methods can include calculating, via the computer system, one or more sleep performance scores associated with one or more of the determined parameters, wherein at least one sleep performance score is an objective measure of sleep quality.

The methods disclosed can include methods for quantifying a sleep quality score of a subject. For example, methods are disclosed that can include measuring one or more parameters relating to a brain activity of the subject. The methods can include determining a total sleep time parameter based upon a function of a total amount of sleep time measured from the subject. The methods can include determining a deep sleep parameter based upon a function of a total amount of deep sleep time measured from the subject. The methods can include determining a sleep efficiency parameter based upon a function of sleep efficiency measured from the subject. The methods can include calculating the sleep quality score based upon a weighting of the total sleep time parameter, deep sleep parameter, and sleep efficiency parameter.

The methods disclosed can include methods for quantifying a brain fitness score of a subject. For example, methods are disclosed that can include measuring one or more parameters relating to a brain activity of the subject. The methods can include determining a total deep sleep time parameter based upon a function of a total amount of deep sleep time measured from the subject. The methods can include determining a longest deep sleep parameter based upon a function of a total amount of longest deep sleep time measured from the subject. The methods can include determining a deep sleep strength parameter based upon a function of deep sleep strength measured from the subject. The methods can include calculating the brain fitness score based upon a weighting of the total deep sleep time parameter, longest deep sleep parameter, and deep sleep strength parameter.

BRIEF DESCRIPTION OF THE DRAWINGS

The drawings shown and described are exemplary embodiments and non-limiting. Like reference numerals indicate identical or functionally equivalent features throughout.

FIG. 5 illustrates a variation of a lookup table.

FIG. 9A illustrates a variation of a method for determining a variation of a sleep quality score.

FIG. 9B illustrates a variation of a method for determining a variation of a sleep quality score.

FIG. 10A illustrates a variation of a method for determining a variation of a brain fitness score.

FIG. 10B illustrates a variation of a method for determining a variation of a brain fitness score.

FIG. 11C illustrates a variation of a graphical user interface.

FIG. 11D illustrates a variation of a graphical user interface.

FIG. 11E illustrates a variation of a graphical user interface.

FIG. 11F illustrates a variation of a graphical user interface.

FIG. 11G illustrates a variation of a graphical user interface.

FIG. 11H illustrates a variation of a graphical user interface.

FIGS. 12A and 12B illustrate a variation of exemplary research data.

FIGS. 13A and 13B illustrate a variation of exemplary cohort categories selected from the research data of FIGS. 12A and 12B.

FIGS. 14A-14D illustrate a variation of a method for deriving total sleep time cohort curves.

FIGS. 17A and 17B illustrate a variation of exemplary cohorts selected from the research data of FIGS. 12A and 16.

FIG. 21 illustrates a variation of exemplary cohorts selected from the research data of FIG. 12A.

FIGS. 22A-22D illustrate a variation of a method for deriving sleep efficiency cohort curves.

FIG. 24A illustrates a variation of a table of exemplary longest deep sleep statistics.

FIG. 25B illustrates a variation of a longest deep sleep reference curve derived from the statistics illustrated in FIG. 24A.

FIG. 24C illustrates a variation of a table of exemplary longest deep sleep scores using the reference curve of FIG. 24B.

FIG. 24D illustrates another variation of a longest deep sleep reference curve.

FIG. 25A illustrates a variation of a table of exemplary deep sleep strength statistics.

FIG. 25B illustrates a variation of a deep sleep strength reference curve derived from the statistics illustrated in FIG. 25A.

FIG. 25C illustrates a variation of a deep sleep strength reference curve derived from the reference curve illustrated in FIG. 25B.

FIG. 25D illustrates a variation of a table of exemplary deep sleep strength scores using the reference curve of FIG. 25C.

FIG. 26A illustrates a variation of exemplary heart rate variability (HRV) data.

FIG. 26B illustrates a variation of exemplary HRV data.

FIG. 26C illustrates a variation of exemplary HRV data.

FIGS. 27A-27D illustrate a variation of a method for deriving HRV cohort curves.

FIGS. 29A and 29B illustrate a variation of sleep data acquired on five different nights and a variation of various analyses performed on the data.

FIG. 30A illustrates a variation of a graphical display.

FIG. 30B illustrates a variation of a graphical display.

FIG. 30C illustrates a variation of a graphical display.

FIG. 30D illustrates a variation of a graphical display.

FIG. 30E illustrates a variation of a graphical display.
FIG. 30F illustrates a variation of a graphical display.

DETAILED DESCRIPTION

Systems and methods are disclosed that can collect sleep data, analyze sleep data, determine one or more sleep performance metrics, make recommendations to improve the quality and/or quantity of a user's sleep, or any combination thereof. The systems and methods disclosed can electronically analyze sleep data and determine sleep performance metrics, for example, by executing computer algorithms. The systems and methods disclosed can recommend ways to improve sleep performance based on a value and/or property of one or more of the determined metrics. The systems and methods disclosed can determine objective and trackable measures of sleep (e.g., metrics associated with sleep quality and/or sleep quantity) that can be used as decision thresholds when making sleep improvement recommendations. The recommendations can be designed to improve sleep quality and/or sleep quantity. The recommendations can include advice, encouragement, constructive criticism, audio stimulation, visual stimulation, cranial electrical stimulation, or any combination thereof. The systems and methods disclosed can provide audio stimulation, visual stimulation, cranial electrical stimulation, or any combination thereof, for example, in response to the system recommending such stimulation and/or as a result of user input instructing the system to provide such stimulation (e.g., with or without a recommendation from the system).

System and Apparatus

Figure 1A:
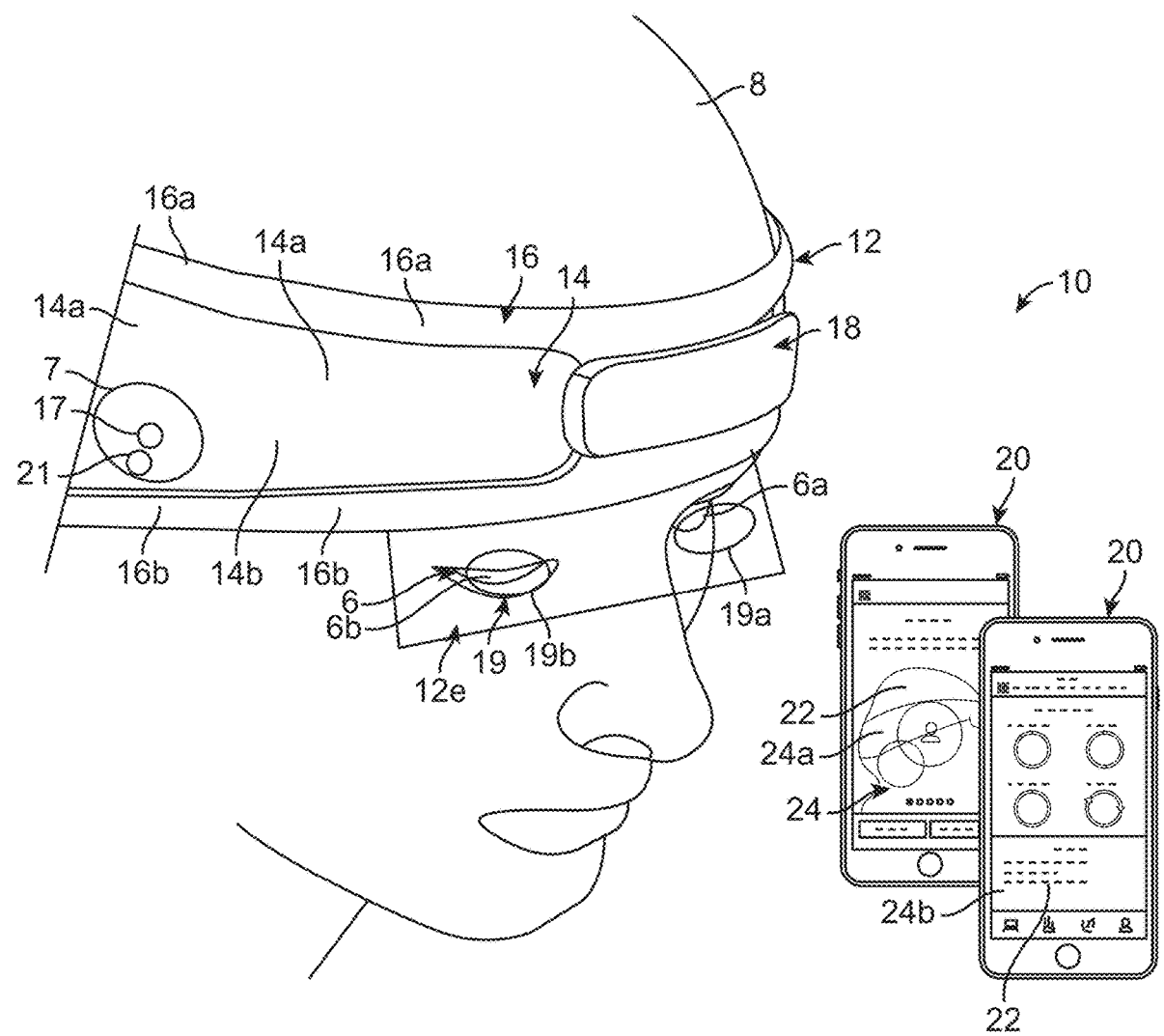
FIG. 1A illustrates a variation of a sleep performance system and a method of use.

FIG. 1A illustrates a variation of a sleep performance system 10. The system 10 can have a data acquisition device 12 and a data display device 20. The data acquisition device 12 can acquire or otherwise collect sleep data, for example, when a user (e.g., a person) is sleeping. The data acquisition device 12 and/or the data display device 20 can analyze the collected sleep data to determine one or more sleep parameters, derive one or more sleep metrics, calculate one or more sleep performance scores, make sleep related observations, make sleep related recommendations, or any combination thereof. The data acquisition device 12 and/or the data display device 20 can electronically display one or more results from the data analysis to inform the user of one or more aspects of their sleep performance. The data acquisition and display devices 12, 20 can be in wired or wireless communication with one another. The data acquisition and display devices 12, 20 can be in wired or wireless communication with a remote server.

FIG. 1A illustrates that the data acquisition device 12 can have a body 14 and one or more edges 16. The body 14 can be a breathable material, for example a mesh material. The breathable material can be configured to allow air to flow across the body 14. The breathable material can advantageously make the data acquisition device 12 more comfortable by allowing the skin beneath the body 14 to breath. The breathable material can be elastic and/or inelastic. The body 14 can have one or more body first regions 14a and/or one or more body second regions 14b. The body first regions 14a can be more elastic (e.g., can stretch more) than the body second regions 14b. For example, the body first regions 14a can be made of an elastic mesh and the body second regions 14b can be made of a less elastic mesh and/or of an inelastic mesh. The body second regions 14b can form ridges configured to lessen the downward force that the body first regions 14a can exert against the head 8. This can increase the comfort of the data acquisition device 12 during use by making it feel less tight when attached to a user's head (e.g., head 8). For example, the body second regions 14b can be configured to raise the body first regions 14a off underlying tissue or hair. The elastic properties of the body 14 can be configured to inhibit or prevent the data acquisition device 12 from slipping during use, such as when the user moves during sleep (e.g., when the user shifts position or when one of their limbs or another person contacts the device 12). The body can extend partially or completely around a perimeter of the head 8.

The edges 16 can be a slip resistance material, for example silicone. The edges 16 can be configured to inhibit or prevent the data acquisition device 12 from slipping during use, such as when the user moves during sleep (e.g., when the user shifts position or when one of their limbs or another person contacts the device 12). The edges 16 can extend partially or completely around a perimeter of the head 8. The edges 16 can form a length and/or a perimeter of the data acquisition device 12. The device 12 can have a first edge 16a (e.g., an upper edge) and/or a second edge 16b (e.g., a lower edge). The first edge 16a can form a first length of the device 12 and the second edge 16b can form a second length of the device 12. For example, the first edge 16a can form a first perimeter of the device 12 and the second edge 16b can form a second perimeter of the device 12. The first and second lengths and/or perimeters can have the same or a different size. The elastic body 14 and the slip resistant edges 16 (e.g., first and second edges 16a, 16b) can be configured to keep the data acquisition in position during use or otherwise inhibit or prevent the data acquisition device from falling off during use.

The elastic body and slip resistant edges 14, 16 can be configured to keep sensors of the data acquisition device 12 in position during use such that there is strong contact and less resistance to movement at the point where the sensors come into contact with the skin. This can advantageously ensure that the device sensors can have reliable contact with the skin. Alternatively or additionally, the data acquisition device 12 can have one or multiple expandable mechanisms configured to keep the sensors of the data acquisition device 12 in position during use such that there is strong contact and less resistance to movement at the point where the sensors come into contact with the skin. The expandable mechanism can allow the sensors to contact the skin with precise pointed pressure (e.g., from pressure provided by the expandable mechanism). The expandable mechanism can be behind one or more sensors of the data acquisition device 12, for example, behind all of the sensors of the data acquisition device, or behind any lesser number of sensors of the device 12. The expandable mechanism can be an inflatable bladder. The expandable mechanism (e.g., the inflatable bladder) can be configured to expand to press one or more sensors into the skin. The expandable mechanism can remain expanded during use. The expandable mechanism can be expanded from an unexpanded configuration to an expanded configuration. The unexpanded configuration can have a first volume and the expanded configuration can have a second volume larger than the first volume. The first volume can be zero or greater than zero. The second volume can be, for example, about 1 mL to about 50 mL, including every 1 mL increment within this range. The expandable mechanism can be expanded until a predetermined pressure threshold is detected between the skin and one or more of the device sensors, for example, by one or more pressure sensors associated with the expandable mechanism. The expandable mechanism (e.g., inflatable bladder) can advantageously enable the device 12 to create skin-sensor contacts that have known and reproducible skin-sensor contact pressures or other measureable quantity that can characterize the contact between the sensors and the skin, or that otherwise fall within an acceptable tolerance such that the device can accurately and precisely record various physiological activity of the subject (e.g., brain activity).

The data acquisition device 12 can be a removably attachable headband, cap, hat, strip (e.g., adhesive strip), biased band, or any combination thereof. The data acquisition device 12 can have the shape of a closed or open loop (e.g., annular or semi-annular shape). The data acquisition device 12 can extend partially or completely around a perimeter of the head 8. For example, FIG. 1A illustrates that the device 12 can be a headband. FIG. 1A further illustrates that the device 12 can extend completely around the head 8, with FIG. 1A being a partial perspective view. FIG. 1A further illustrates that the device 12 can extend partially around the head 8, with FIG. 1A being a partial perspective view. The device 12 can cover one or both ears (e.g., ears 7) in either or both of the "partially around" and "completely around" configurations. Additionally or alternatively, the device 12 can be configured to not cover one or both ears or otherwise not cover a portion thereof.

The data acquisition device 12 can be positionable on a person's head 8 (e.g., during sleep and/or during naps). For example, FIG. 1A illustrates that the data acquisition device 12 can be removably positioned on the head 8. The data acquisition device 12 can be positioned on the head 8 with an elastic fit or an interference fit, and/or one or more portions of the data acquisition device can be removably adhered to the head (e.g., to skin, to the forehead), for example, with an adhesive. The data acquisition device 12 can be configured for temporary securement to the head 8. The data acquisition device 12 can resist dislodgment from a secured position (e.g., attached position), for example, via the elasticity of the body 14 and/or the slip resistance of the edges 16.

The data acquisition device 12 can have an adjustable size to accommodate different head sizes. For example, the data acquisition device 12 can have an adjustable strap. The data acquisition device 12 can have a nonadjustable size. The system 10 can have multiple data acquisition devices 12 (e.g., 2 to 5 data acquisition devices), each having a different adjustable or nonadjustable size. For example, the system 10 can have three data acquisition devices 12, for example, first, second, and third data acquisition devices 12, each having a progressively larger size. For example, the first, second and third data acquisition devices 12 can correspond to small, medium and large sizes, respectively. As another example, the system 10 can have one or more child-sized data acquisition devices (e.g., devices 12) and one or more adult-sized data acquisition devices (e.g., devices 12).

FIG. 1A illustrates that the data display device 20 can have a display 22 (e.g., a graphics display such as a graphics user interface (GUI)). The display 22 can be a touchscreen. The display 22 can display, for example, a user interface 24. The user interface 24 can be generated via a computer algorithm, for example via software downloaded to or callable from a portable electronic device (e.g., a smartphone).

The user interface 24 can have one or multiple interactive screens. For example, FIG. 1A illustrates that the user interface 24 can have a first screen 24a and a second screen 24b. The first screen 24a can, for example, correspond to a startup screen having a "sign in" selection and a "get started" selection. The second screen 24b can, for example, correspond to a data results screen (e.g., a sleep summary screen).

The user interface 24 can display raw data, analyzed data, observations, recommendations, or any combination thereof. For example, FIG. 1A illustrates that the second screen 24b can list various observations titled "AH-HA'S" (also referred to as performance insights, things worth noting, things worth mentioning). The observations can be tied to one or more determined parameters and/or to one or more sleep performance metrics (e.g., derivations involving one or more determined parameters). The observations can provide text summaries of a user's sleep performance (e.g., "insufficient total deep sleep"), as well as insights related to the user's sleep performance (e.g., "high stress levels," "high stress levels detected"). The recommendations can include goal suggestions related to one or more influencers of the user's sleep performance. The influencers can be variables and/or behaviors that can, may, and/or do affect sleep generally and/or the user's sleep specifically. For example, the system 10 can provide recommendations such as "smoke one less cigarette today," "go for a 10-20 minute walk at 7 pm," "have your Wednesday glass of wine 30 minutes earlier today," "plan something fun for this weekend."

Figure 1B:
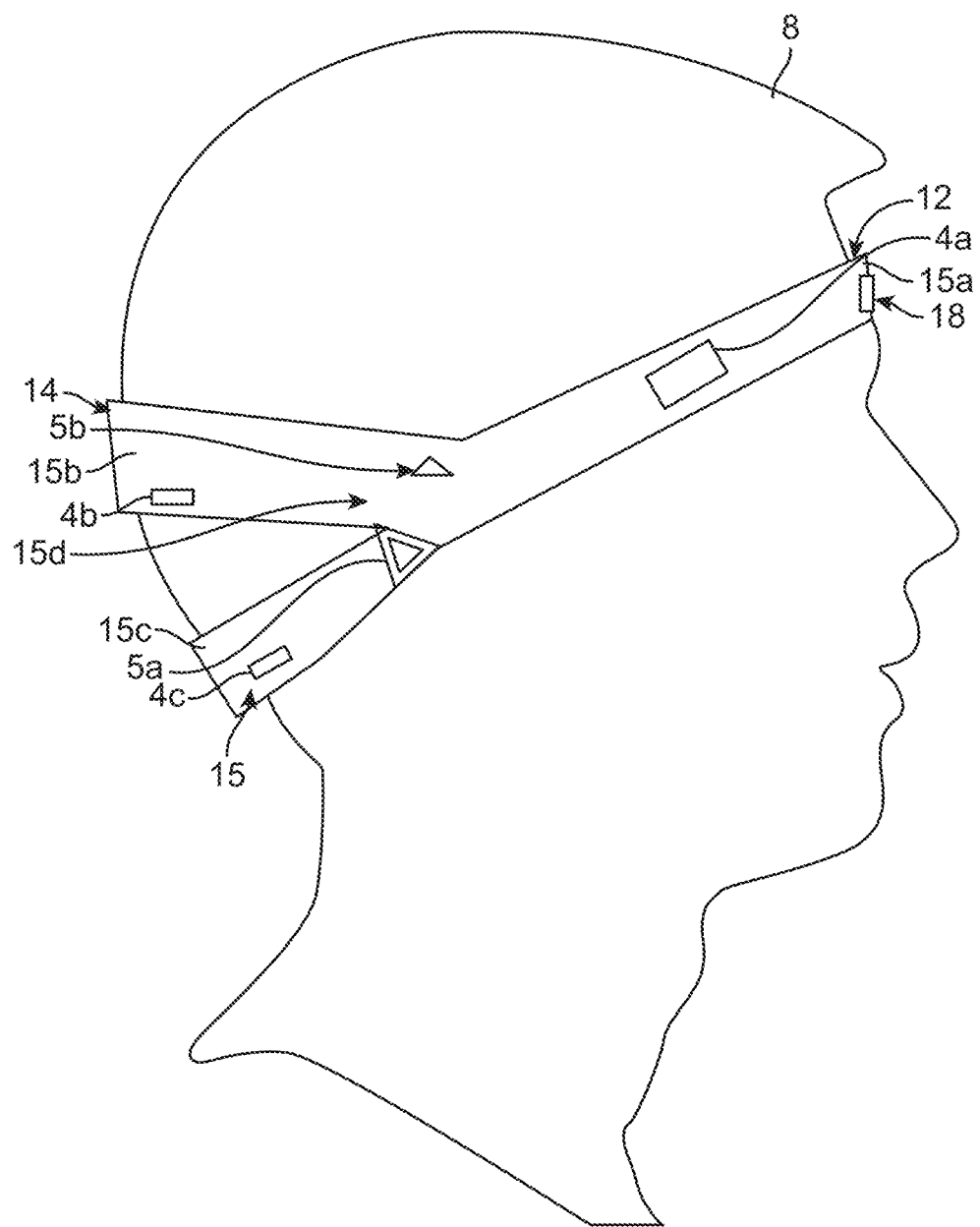
FIG. 1B illustrates a variation of a data acquisition device.

FIG. 1B illustrates that the data acquisition device 12 can have a body 14 comprising multiple bands 15, for example, a first band 15a, a second band 15b, and a third band 15c. The first, second, and third bands 15a, 15b, 15c can be separate bands and/or can be different band portions of a single unitary band. For example, the first, second, and/or third bands 15a, 15b, 15c can be attached to or integrated with one another at attachment region 15d. The data acquisition device 12 can form a headband. The first band/band portion 15a can form a front band/strap. The second and third bands/band portions 15b, 15c can form back bands/straps. The device 12 can have a 'split band' in the back of the head 8 formed by the second and third straps 15b, 15c, where the bottom band (e.g., the third band 15c) can be configured to cup under the curve of the back of the head to reduce any potential slippage/movement of the headband. The angle of the bands can be fixed or moveable. For example, the fixed or moveable (e.g., adjustable) angle can be from about 10 degrees to about 120 degrees, including every 1 degree increment within this range (e.g., 30 degrees, 45 degrees). A band adjuster 5a (e.g., the 'teva-like triangle' 5a) can enable back straps (e.g., bands 15b and 15c) to adjust to contour to person's head. The band adjuster 5a can allow the second band 15b to be adjusted independently from the third band 15c. The band adjuster 5a can allow the third band 15c to be adjusted independently from the second band 15b. The band adjuster 5a can allow the angle between the second and third bands 15b, 15c to be adjusted. Alternatively or additionally, the device 12 can have another band adjuster 5b that can have the same functionality as the band adjuster 5a. The device 12 can have one or more length adjustment mechanisms configured to allow the length of the one or more bands to be increased, decreased, and/or locked into position. For example, FIG. 1B illustrates that the device 12 can have a first length adjustment mechanism 4a for the first band/band portion 15a, a second length adjustment mechanism 4b for the second band/band portion 15b, a third length adjustment mechanism 4c for the third band/band portion 15c, or any combination thereof.

Stimulation

FIG. 1A illustrates that the system 10 can provide audio stimulation (also referred to as audio entrainment) using, for example, one or more sound wave generators 17 (e.g., 1 to 4 sound wave generators). The sound wave generators can be, for example, speakers. A portion of the data acquisition device 12 can be positionable over and/or engageable with a left and/or right ear 7 of a user such that the speakers 17 can emit sound into a user's ears 7. The data acquisition device 12 can be configured to partially or completely cover one or both ears 7. For example, FIG. 1A illustrates that a body first region 14a can completely cover the right ear 7. A portion of the data acquisition device 12 can be configured for temporary securement on and/or to a user's ears. A portion of the data acquisition device 12 can be configured to fit in or extend into an ear canal. The speakers 17 can be attached to, embedded in, or integrated with the device body and/or device edges 14, 16. The speakers 17 can be in wired or wireless communication with the data acquisition device 12, the data display device 20, a remote server, or any combination thereof. The speakers 17 can be micro speakers. Alternatively or additionally, the system 10 can have one or more plastic tubes (e.g., small plastic tubes) configured to direct sound to the ears 7. The sound wave generator/speaker 17 can be connected to the small plastic tubes. The plastic tubes can more precisely direct sound to the ears 7 and can be more comfortable over the ear. One or more of the speakers 17 can be noise canceling speakers (e.g., to cancel environmental noise).

Additionally or alternatively, the system 10 can provide audio stimulation via bone conduction by transmitting sound signals through bone to a user's inner ear. The system 10 can have one or more actuator assemblies 13 to provide bone conduction sound transmission. The actuator assemblies 13 can have an actuator. The actuator can be vibratable (e.g., the actuator can be configured to vibrate). The actuator assemblies 13 can have a transceiver coupled to the actuator. The transceiver can cause the actuator to vibrate to generate sound, for example, when the transceiver is electronically driven with sound signals (e.g., from a driver and/or a controller, for example, from the device 12 and/or the device 20). The actuator can be a piezoelectric actuator. The piezoelectric actuator can be configured to move a mass to provide sound through bone. The actuator assemblies 13 (e.g., the actuator) can be positioned near the ear and/or on the cheek. For example, the actuator assemblies 13 can be positioned on a user's skin proximate the zygomatic bone, the zygomatic arch, the mastoid process, or any combination thereof. The system 10 can have 1 to 6 actuator assemblies, or 1 to 6 actuators, including every 1 actuator assembly/actuator increment within these ranges. For example, FIG. 1A illustrates that the data acquisition device 12 can have one actuator assembly near the right ear 7. As another example, FIG. 1A illustrates that the data acquisition device 12 can have two actuator assemblies 13, one near the right ear 7 and another near the left ear (not shown).

Examples of audio stimulation that the system 10 can provide are provided in Papalambros et al. Acoustic Enhancement of Sleep Slow Oscillations and Concomitant Memory Improvement in Older Adults, *Frontiers in Human Neuroscience*, Mar. 8, 2017, Volume 11, Article 109, Pages 1-14; Ngo et al. Auditory Closed-Loop Stimulation of the Sleep Slow Oscillation Enhances Memory, *Neuron*, May 8, 2013, No. 78, Pages 545-553; and Santostasi et al. Phase-locked loop for precisely time acoustic stimulation during sleep, *Journal of Neuroscience Methods* 259 (2016) 101-114, which are each herein incorporated by reference in their entireties for all purposes.

FIG. 1A further illustrates that the system 10 can provide visual/optical stimulation (also referred to as light entrainment) using, for example, one or more light emitting sources 19 (e.g., 1 to 20 light emitting sources). A portion of the data acquisition device 12 can be positionable over and/or engageable with a left and/or right eye 6 of a user such that the light sources 19 can emit light into a user's eyes 6 (e.g., through the user's closed eyelids). The data acquisition device 12 can be configured to partially or completely cover one or both eyes 6. The data acquisition device 12 can be configured for temporary securement above or proximate to a user's eyes/eyelids. For example, a portion of the data acquisition device 12 can be configured to rest against and/or adhere to an eyebrow, the area proximate an eyebrow, the glabella, the nose (e.g., dorsal bridge, dorsal base, tip), cheek, or any combination thereof. For example, FIG. 1A illustrates that the device 12 can have an eye cover 12e configured to cover (e.g., partially or completely) the left and right eyes 6a, 6b. The eye cover 12e can be permanently or removably attached to or integrated with the device 12 (e.g., to or with the body and/or edges 14, 16). The light sources 19 can be attached to, embedded in, or integrated with the device 12 (e.g., the device eye cover 12e). The eye cover 12e can have one or multiple light sources 19. For example, the eye cover 12e can have a first light source 19a configured to emit light into the left eye 6a and a second light source 19b configured to emit light into the right eye 6b.

FIG. 1A further illustrates that the system 10 can provide cranial electrical stimulation (CES) using, for example, one or more electrodes 21 placed on an ear (e.g., earlobe), maxilla-occipital junction, mastoid process, temple, or any combination thereof.

The system 10 can provide audio entrainment, optical entrainment, CES, or any combination thereof, in addition to or in lieu of the data collection and associated analyses described below.

Data Collection & Analysis

The data acquisition device 12 can be configured to measure and collect one or more physiological parameters during sleep. For example, the data acquisition device 12 can be configured to detect, measure, monitor, and record brain activity, eye activity, muscle activity (e.g., body posture, limb movements), cardiac activity (e.g., heart rate variability (HRV)), respiration activity (e.g., respiration rate), blood oxygen saturation, or any combination thereof. For example, the data acquisition device 12 can be configured to detect, measure, monitor, and record brain activity using electroencephalography (EEG), eye activity using electrooculography (EOG), muscle activity using electromyography (EMG), cardiac activity using electrocardiography (ECG), respiration rate (e.g., using respiratory inductance plethysmography (RIP), pressure sensor, and/or a temperature sensor), oxygen saturation (e.g., using pulse oximetry), or any combination thereof. The data acquisition device 12 can be configured to detect, measure, monitor, and record pressure and temperature, for example, using one or more pressure sensors and/or one or more temperature sensors. The data acquisition device 12 can perform polysomnography (PSG) tests and can collect polysomnographic data. The data that is collected is referred to throughout as acquired data, raw data, and/or sleep data.

The data acquisition device 12 can have one or more data acquisition modules 18 (also referred to as electronics modules 18), for example, 1 to 5 electronics modules 18, including every 1 module increment within this range (e.g., 2 electronics modules). For example, FIG. 1A illustrates that the data acquisition device 12 can have one electronics module 18.

The one or more electronics modules 18 can be configured to monitor and record one or more physiological activities during sleep. For example, the electronics modules 18 can be configured to detect, measure, monitor, and record brain activity, eye activity, muscle activity, cardiac activity, respiration activity, blood oxygen saturation, or any combination thereof (e.g., using EEG, EOG, EMG, ECG, RIP, pulse oximetry, or any combination thereof, respectively). The one or more electronics modules 18 can be computer interfaces, for example, brain computer interfaces (BCIs).

The data acquisition device 12 (e.g., the electronics modules 18) can have one or more electrodes, sensors (e.g., biosensors), accelerometers, or any combination thereof. For example, the data acquisition device 12 (e.g., the electronics modules 18) can have one or more EEG biosensors, EOG biosensors, EMG biosensors, ECG biosensors, respiration rate biosensors, pulse oximetry biosensors, HR biosensors, temperature sensors, pressure sensors, or any combination thereof, including one or more reference sensors and/or one or more ground electrodes.

The data acquisition device 12 (e.g., the electronics modules 18) can have a single-channel and/or a multi-channel EEG system. The multi-channel EEG system can be operated as a single channel EEG system. The EEG system (single or multi-channel) can include one or more EEG sensors. The data acquisition device 12 (e.g., the electronics modules 18) can have 1 to 10 EEG sensors, including every 1 EEG sensor within this range (e.g., 4 EEG electrodes). The data acquisition device 12 (e.g., the electronics modules 18) can have more than 10 sensors (e.g., 1 to 100 EEG sensors). The electronics modules 18 can have an EEG sensor array or an EEG sensor network (e.g., of 2 to 10 or more sensors). One of the EEG sensors can be a ground electrode. The EEG system can have one or multiple reference electrodes (e.g., one or two reference electrodes). The electronics module 18 can have, for example, three channels of frontal EEG and one EEG reference sensor. The EEG electrodes can be positioned on the forehead as illustrated in FIG. 1A. The EEG electrodes can be placed according to the international 10-20 system.

The data acquisition device 12 (e.g., the electronics modules 18) can have 2, 3, or 4 EOG sensors. Two EOG sensors can detect/measure movement of one or both eyes. For example, two EOG sensors can be positioned to detect/measure eye movement of the left and right eyes (e.g., a first EOG sensor can be positioned on the right outer edge of the right eye and a second EOG sensor can be positioned on the left outer edge of the left eye), two EOG sensors can be positioned to detect/measure eye movement of only the left eye (e.g., a first EOG sensor can be positioned on the right outer edge and a second EOG sensor can be positioned on the left outer edge of the left eye), or two EOG sensors can be positioned to detect/measure eye movement of only the right eye (e.g., a first EOG sensor can be positioned on the right outer edge and a second EOG sensor can be positioned on the left outer edge of the right eye). Three EOG sensors can be positioned to detect/measure eye movement of the left and right eyes (e.g., a first EOG sensor can be positioned on the right outer edge of the right eye, a second EOG sensor can be positioned on the left outer edge of the left eye, and a third EOG sensor can be positioned between the left and right eyes). The three EOG sensors can selectively detect/measure eye movement of the left and/or right eyes, with the first and third EOG sensors configured to detect/measure movement of the right eye, with the second and third EOG sensors configured to detect/measure movement of the left eye, and with the first and second EOG sensors configured to detect/measure movement of the left and right eyes together. Four EOG sensors can be positioned to detect/measure eye movement of the left and right eyes (e.g., first and second EOG sensors can be positioned on first and second sides of the left eye and third and fourth EOG sensors can be positioned on first and second sides of the right eye). The "outer edges" of the eyes can be in line with the eyes, above the eyes and/or below the eyes.

The system 10 can have 1 to 6 EMG sensors, including every 1 EMG electrode increment within this range (e.g., 2 EMG electrodes).

The system 10 (e.g., the data acquisition device 12 and/or the electronics modules 18) can have 1 to 10 ECG sensors, including every 1 ECG electrode increment within this range (e.g., 1, 2, or 3 ECG electrodes). The ECG sensors can be used to measure HRV. The ECG sensors can be used to determine HRV.

The system 10 (e.g., the data acquisition device 12 and/or the electronics modules 18) can have 1 to 10 heart rate sensors, including every 1 heart rate sensor increment within this range (e.g., 1, 2, or 3 heart rate sensors). The heart rate sensors can be used to measure HRV. The heart rate sensors can be used to determine HRV.

The system 10 can have an RIP system. The RIP system can be in electrical communication with the data acquisition device 12. The RIP system can measure movement of the chest and abdominal wall, for example, using one or more belts. Additionally or alternatively, the system 10 (e.g., the data acquisition device 12 and/or the electronics modules 18) can have one or multiple pressure sensors (e.g., pressure transducers) and/or temperature sensors (e.g., thermocouples) configured to monitor respiration. For example, the data acquisition device 12 can have 1 to 4 pressure sensors, including every 1 pressure sensor increment within this range (e.g., 1 or 2 pressure sensors). The data acquisition device 12 can have 1 to 4 temperature sensors, including every 1 temperature sensor increment within this range (e.g., 1 or 2 temperature sensors). The pressure and/or temperature sensors can be positionable near the nostrils and can be configured to detect the pressure/temperature changes that occur when a user inhales and exhales. The pressure and/or temperature sensors can be attached to or integrated with the data acquisition device 12 such that when the device 12 is removably secured to a head, the pressure and/or temperature sensors are positioned in a breathing flow path (e.g., near the nostrils and/or mouth, for example, for mouth breathers).

The data acquisition device 12 can have a pulse oximetry sensor that can be removably attachable to an ear (e.g., ear 7), for example, to an ear lobe. The system 10 can have a pulse oximetry sensor that can be removably attachable to a finger. The finger pulse oximetry sensor can be in wired or wireless communication with the data acquisition device 12 (e.g., to the electronics module 18) and/or to the data display device 20. The ear pulse oximetry sensor can be attached to or integrated with the device 12. The pulse oximetry sensor (ear and finger sensor) can be a component of a clip. The clip can attach to (e.g., clip to) an ear lobe or a finger. The clip can be attached to or integrated with the device 12, for example, to the body 14 and/or edges 16.

The data acquisition device 12 can have one or more pressure sensors (e.g., 1, 2, 3, 4, 5, 6 or more) configured to detect when the device 12 is attached to a head, for example, by measuring the amount of force exerted against each of the pressure sensors. The system 10 (e.g., the devices 12 and/or 20) can be configured to detect whether the device 12 is properly positioned on the head, for example, by detecting and/or comparing the different pressures measured by the one or more pressure sensors (e.g., by calculating one or more pressure differentials). The pressure sensors can also be used to determine whether the position can be improved or further optimized, for example, for more accurate and/or reliable data collection. The device 12 can be activated (e.g., automatically or manually) when positioned on the head 8 as a result of one or more pressure sensors exceeding a pressure threshold. The device 12 can be activated (e.g., automatically or manually) when positioned on the head 8 as a result of one or more differential pressure differentials (e.g., between two sensors) falling below a differential pressure threshold.

For example, a first pressure sensor can be on a first side of the device 12 and a second pressure sensor can be on a second side of the device 12. The pressure sensors can be separated by about 1 degree to about 180 degrees as measured from a center of the device 12 (e.g., along a longitudinal and/or transverse axis), including every 1 degree increment within this range. The center of the device 12 can fall between two inner sides of the device such that the device center is not on the body and/or edges 14, 16 of the device 12. A 180 degree separation can correspond to a configuration in which the first and second pressure sensors are diametrically opposed from one another. Angles less than 180 degrees can correspond to configurations in which the first and second pressure sensors are on opposite sides of the device, determined for example relative to a reference axis. Angles less than 180 degrees can correspond to configurations in which the first and second pressure sensors are on the same side of the device, determined for example relative to a reference axis. The first and second pressure sensors can be used to determine a side-to-side or a front-to-back pressure differential of the device 12 (i.e., the pressure levels on the left side, right side, front side, and/or back side of the device 12). Four pressure sensors can be used to determine side-to-side and/or front-to-back pressure differentials of the device when removably attached to a head. The angles between sensors can be from about 1 degree to about 180 degrees, including every 1 degree increment within this range.

The system 10 (e.g., the device 12, the device 20, and/or a remote server) can determine whether the device 12 is properly or improperly positioned by analyzing the pressure readings of the one or more pressure sensors. If properly positioned, the device 12 can automatically begin collecting data (e.g., immediately or after one or more additional conditions are satisfied). If properly positioned, the data display device 20 can prompt the user with a selectable command (e.g., via a graphic on a touch screen) to begin data collection (e.g., "start recording," "good night," "good night, have a good rest," "begin data collection," "sleep well, let's begin data collection"). The prompt can be customizable. If improperly positioned, the data display device 20 can provide the user with suggested instructions to correct the improper placement (e.g., "please rotate the headband to the right/left," "please pull the head band lower or higher onto your forehead," "please adjust the headband so that the sensors are on your forehead," "please loosen the headband," "please tighten the headband"). The system 10 can also be configured to provide recommendations to make a proper position more comfortable. For example, the data display device 20 can be configured to display messages such as "the device is positioned properly, but it might be a little tight. Feel free to loosen it a bit! We don't want you to wake up with a headache ☺"). The device 12 can be activated (automatically or manually) to collect data even when not in a proper position. The device 12 can collect data when not positioned properly, however, some of the data may have accuracy, precision and/or reliability issues, or some of the data may be missing altogether (e.g., pulse oximetry data). Additionally or alternatively, the devices 12 and/or 20 can be configured to determine whether the device 12 is properly positioned by measuring the voltage drop across one of more sensors of the electronics modules 18).

The data acquisition device 12 can begin collecting data when one or more conditions are satisfied (e.g., 1 to 5 or more conditions). The data acquisition device 12 can begin collecting data when a proper position is detected. The data acquisition device 12 can begin collecting data when the system 10 detects that the user is in a sleeping position and/or when the user is in a sleeping location, for example, for a predetermined amount of time (e.g., immediately (no time), or after 1 min to 5 min or more have elapsed). The sleeping location can be established or otherwise settable by the user. For example, the data acquisition device 12 can begin collecting data after first, second, third, and/or fourth conditions are satisfied. The device 12 can begin collecting data immediately after any one condition or combination of conditions is satisfied. The first condition can correspond to correct device placement (e.g., of the device 12). The second condition can correspond to user input (e.g., selection of a command prompt). The third condition can correspond to a position of the device relative to the environment, for example, whether the orientation of the device 12 is in a position indicative of a sleeping position of the user (e.g., lying down, either prone, supine, or on side). The fourth condition can correspond to a location of the user (e.g., on a bed). Sleep data collection can begin when the pressure sensors detect that the device 12 is attached to a head. Sleep data collection can begin when the pressure sensors detect that the device 12 is properly attached to a head.

The data acquisition device 12 can have one or more temperature sensors (e.g., 1, 2, 3, 4 or more temperature sensors) configured to monitor a user's body temperature. The temperature sensors can be temperature transducers (e.g., thermocouples). The temperature sensor can be attached to or integrated with the device 12. The temperature sensors can be configured to detect when the device 12 is attached to a head, for example, by detecting a body temperature. An environment temperature sensor can be configured to measure environmental temperature. The environment temperature sensor can be one of the temperature sensors of the device 12. The environment temperature sensor can be a temperature sensor of a sleeping location (e.g., house or apartment). The system 10 can determine a user's optimum sleeping temperature and suggest a sleeping temperature for the user, for example, from about 60 degrees Fahrenheit to about 85 degrees Fahrenheit, including every 1 degree increment within this range. For example, the system 10 (e.g., the data display device 10) can make suggestions such as "we suggest a sleeping temperature of 71 degrees Fahrenheit" or "we suggest a sleeping temperature of 78 degrees Fahrenheit." The user can adjust the temperature of their sleeping location (e.g., house, apartment) or the system 10 can be in wired or wireless communication with a heating and/or air conditioning system of the sleeping location and control the environmental temperature automatically.

The system 10 (e.g., the data acquisition device 12 and/or the electronics modules 18) can have one or more accelerometers (e.g., one accelerometer). The accelerometer can detect a user's positional state, for example, a user's movement. The accelerometer can be a two-axis accelerometer. The accelerometer can be a three-axis accelerometer. The accelerometer can be configured to detect head, body, and/or limb movements, or any combination thereof. The accelerometer can be used to detect lack of movement as well, for example, the length of time in a single position without movement or with movement within a specified tolerance (e.g., voltage level or movement amount, for example, 5 cm or less).

The electronics modules (e.g., electronics modules 18) can include, for example, three channels of frontal EEG and one EEG reference sensor to detect brain wave activity, a heart rate sensor to monitor cardiac activity (e.g., RR variability), an accelerometer (e.g., two or three axis accelerometer) to detect head, body, and/or limb movements, or any combination thereof.

FIG. 1A illustrates that the module 18 can be configured to contact a user's skin (e.g., a user's forehead) during use. The device 12 can press the EEG sensors and/or ECG sensor(s) against the user's skin (e.g., forehead) when secured to the head 8, for example, with an elastic fit or with an interference fit. Alternatively or additionally, the sensors can be adhered to the user's skin (e.g., forehead) using an adhesive with or without the device 12.

The electronics module 18 can be configured to measure brain activity, for example, during light sleep, during rapid eye movement (REM) sleep, during slow-wave sleep (SWS) (also referred to as deep sleep), or any combination thereof. The electronics module 18 can be configured to measure cardiac activity, for example, HRV such as RR intervals. The electronics module 18 can be configured to detect a user's motion and/or a user's lack of motion.

The electronics module components (e.g., channels, sensors, accelerometers) can be attached to or integrated with the data acquisition module 18. The data acquisition module 18 can be permanently attached to, removably attached to, or integrated with the device 12 (e.g., to and/or with the body 14 and/or edges 16). Additionally or alternatively, the various activity-measuring components (e.g., channels, sensors, accelerometers) can be attached to or integrated with an attachment portion of the data acquisition device 12, for example the body 14 and/or the edges 16 separate and apart from the module 18. The module 18 can be interchangeable with one or more other modules (not shown) having a different number of sensors, one or more different types of sensors, or otherwise having at least one different parameter-measuring capability relative to the electronics module 18. The module 18 can be interchangeable with another module having the same exact module or otherwise with another module having the same exact parameter-measuring capabilities. Different modules 18 can have different sizes relative to one another. Different modules 18 can have different shapes relative to one another.

The data acquisition device 12 can be reusable or disposable. The electronics modules 18 can be reusable or disposable.

The data acquisition device 12, the data display device 20, and/or a remote server can analyze the sleep data collected. The data acquisition device 12, the data display device 20, and/or a remote server can determine one or more parameters from the data collected, for example, using one or more programmable processors. The parameters can include total light sleep, total SWS (also referred to as total deep sleep), total REM sleep, total non-REM sleep (total light sleep and total SWS added together), total sleep (total REM and non-REM sleep added together), longest deep sleep duration, deep sleep amplitude, heart rate, heart rate variability, total time in bed, time to fall asleep, time awake between falling asleep and waking up, or any combination thereof. The time-based parameters (e.g., the "total," "duration," and "time" parameters) can be measured in the time domain, for example, using seconds, minutes, hours. Days, weeks and years can be used for accumulated and/or running totals.

The total time in bed parameter can be measured from a start point to an end point. The start point can correspond to when the user manually activates the data acquisition device 12, for example, by selecting a start instruction (e.g., "ready to sleep") on the display 22. The start point can correspond to when the device 12 is activated (e.g., automatically or manually). The device 12 can be automatically activated, for example, when a voltage is detected across two or more sensors of the module 18 (e.g., across two or more of the EEG electrodes). The voltage can indicate contact with skin and cause the device 12 to begin measuring the total time in bed. The device 12 can have a timer. The device 12 can be automatically activated when positioned on the head 8 as a result of one or more pressure sensors exceeding a pressure threshold. The end point can correspond to when the user manually deactivates the data acquisition device 12, for example, by selecting an end instruction (e.g., "turn off alarm" or "get sleep report") on the display 22. The end point can correspond to when the device is automatically deactivated. The device 12 can be automatically deactivated, for example, when the accelerometer indicates the user is walking around or has taken the device 12 off their head.

The data acquisition device 12, the data display device 20, and/or a remote server can calculate or otherwise derive one or more sleep performance metrics from one or more of the measured parameters, for example, using one or more programmable processors. The calculated metrics can be parameter totals (e.g., total sleep, total SWS, total REM sleep, total light sleep, total non-REM sleep). The calculated parameters can include sleep efficiency, deep sleep deficit (also referred to as deep sleep debt or accumulated deep sleep deficit), and strength of deep sleep, or any combination thereof. The sleep efficiency metric can be the ratio of the total sleep time divided by the total time in bed $$\left(\text{i.e., } \frac{\text{total sleep time}}{\text{total time in bed}}\right).$$

The strength of deep sleep metric can be the deep sleep deficit accumulated over multiple nights, for example, 2 to 14 nights, including every 1 night increment within this range (e.g., 5 nights). The strength of deep sleep metric can be measured in microvolts (µV) or power spectral density, and can reflect the amplitude/power of the brainwaves in deep sleep, which can be determined by how much of the brain is in deep sleep, i.e., the more of the brain that is in slow-wave sleep, the higher the amplitude, and the stronger the deep sleep. If the user does not wear the device 12 for two or more consecutive nights (e.g., 5 consecutive nights), then the strength of deep sleep metric can be excluded from the sleep performance score calculations.

The data acquisition device 12, the data display device 20, and/or a remote server can identify and record a user's sleep cycles, for example, using one or more programmable processors, and can determine the length of time spent in each sleep cycle. A complete sleep cycle can include non-REM sleep and REM sleep. Non-REM sleep can include light sleep and deep sleep. The system 10 can identify and record light sleep, deep sleep and REM sleep, and can determine the total time spent in each, and in any combination (e.g., total light and deep sleep, total light and REM sleep, total deep and REM sleep). A complete sleep cycle can have 4 stages. Light sleep can correspond to sleep stages 1 and 2. Deep sleep can correspond to sleep stage 3. REM sleep can correspond to sleep stage 4. Sleepers complete a sleep cycle by passing through stages 1, 2, 3, and 4 in sequential order. Stages 1-4 can progress cyclically from stage 1 to stage 4 and then repeat, beginning again at stage 1. The system 10 can identify and record the total time spent in each stage, and in any combination (any combination of stages 1, 2, 3, and 4).

SWS periods in early sleep cycles can be longer relative to later sleep cycles, and REM sleep periods in early sleep cycles can be shorter relative to later sleep cycles (i.e., as a user progressively moves from one sleep cycle to the next, time spent in REM sleep can increase and time spent in SWS can sleep decrease). The system 10 (e.g., data acquisition device 12, the data display device 20, and/or a remote server) can identify the differences in time spent in each of the corresponding stages across multiple sleep cycles, including the relative increases in REM sleep and the relative decreases in SWS across sleep cycles. The system 10 can identify and record the total time spent in each sleep cycle. The system 10 can detect when a sleep cycle has been interrupted. The system 10 can detect the stage in which a sleep cycle has been interrupted. The system 10 can detect the length of the interruption and the user's ability to recover, also referred to as a user's recovery efficiency. The recovery efficiency can include a comparison of the sleep stage before the interruption and the sleep stage entered after the interruption, where a 100% recovery efficiency can correspond to when the pre-interruption and post-interruption sleep stages are identical to one another. A lesser percentage (e.g., 50%) can correspond to where the pre-interruption stage does not match the post-interruption stage. The recovery efficiency can include a measure of post-interruption sleep stage progression, where an accelerated progression through the sleep stages to again be at the stage at which the interruption occurred can correspond to a high efficiency.

The data acquisition device 12, the data display device 20, and/or a remote server can calculate or otherwise derive one or more sleep performance scores from one or more of the determined parameters and/or calculated parameters, for example, using one or more programmable processors. The sleep performance scores can include a sleep quality score, a brain fitness score, a recharge score (also referred to as recovery score or readiness score), an influencers score, or any combination thereof.

The system 10 can have a database of data sets. The system 10 can determine one or more sleep performance scores by referencing one or more of the data sets. For example, the system 10 can determine the sleep quality, brain fitness and recharge scores by referencing one or more stored data sets. The data sets can correspond to one or more measured parameters and/or derived sleep metrics. The data sets can correspond to calculated distributions of one or more parameters and/or derived sleep metrics. The data sets can be represented numerically and/or visually (e.g., via tables and/or graphs). The data sets can be lookup tables. The data sets can be lookup graphs having reference curves.

The data sets can associate the measured and/or calculated parameters and/or metrics with a total number of points for any given value of the parameter and/or metric. The total points associated with a parameter/metric can correspond to a sleep performance score, and/or the total points from multiple parameters/metrics (e.g., 2 to 5 or more parameters/metrics) can be combined to determine a sleep performance score. The total points from two or more parameters/metrics can be combined via one or more mathematical operations such as addition, weighted (e.g., percentage-based) addition, subtraction, weighted (e.g., percentage-based) subtraction, multiplication, weighted (e.g., percentage-based) multiplication, division, weighted (e.g., percentage-based) division, or any combination thereof.

The data sets can be separated into cohorts, for example, based on age, gender, ethnicity, health, fitness level, or any combination thereof, and/or can be represented without breaking up the data into cohorts. For example, the data sets (e.g., cohort curves) can be gender neutral and/or gender-specific (e.g., male and/or female), such as gender neutral age cohort curves. Additionally or alternatively, a user's personal history and/or baselines (e.g., baseline scores, baseline goals) can be used in the scoring methodology when determining one or more of the sleep performance scores. The system 10 can progressively transition from the use of one or more stored data sets to the use of a user's personal history and/or baselines as acquired by the system 10 and/or set by the user. For example, the system 10 can progressively decrease the use of stored data sets from 100% to 0% by a 10% to 25% increment per time period (e.g., 1 day to 30 days, including every 1 day increment within this range) and/or per number of uses of the system 10 (e.g., 1 use to 30 uses, including every 1 use increment within this range). The percentages can correspond to weights when determining the total points for one or more of the parameters/metrics, and/or to weights when determining one or more of the sleep performance scores (e.g., sleep quality score, brain fitness score, recharge score, influencers score). The system 10 can progressively increase the use of the user's personal history and/or baselines by an equal percentage that the stored data set percentage use is decreased, for example, from 0% to 100% by a 10% to 25% increment. Alternatively or additionally, the system 10 can progressively decrease the use of stored data sets to from 1% to 80% from a 100% starting point and vice versa for the personal history and baseline database, for example, to from 1% to 80% from a 0% starting point.

The system 10 can aggregate and anonymize all the user data in the cloud, analyze the data to identify patterns in terms of what audio stimulation worked for which cohorts of people (e.g., gender, age, ethnic, fitness, health) under what situations (e.g., exercised that day, coming off of a poor/good Sleep Quality night) and then within a closed loop, update the algorithms accordingly so that the learnings are applied to the broader population.

Figure 2A:
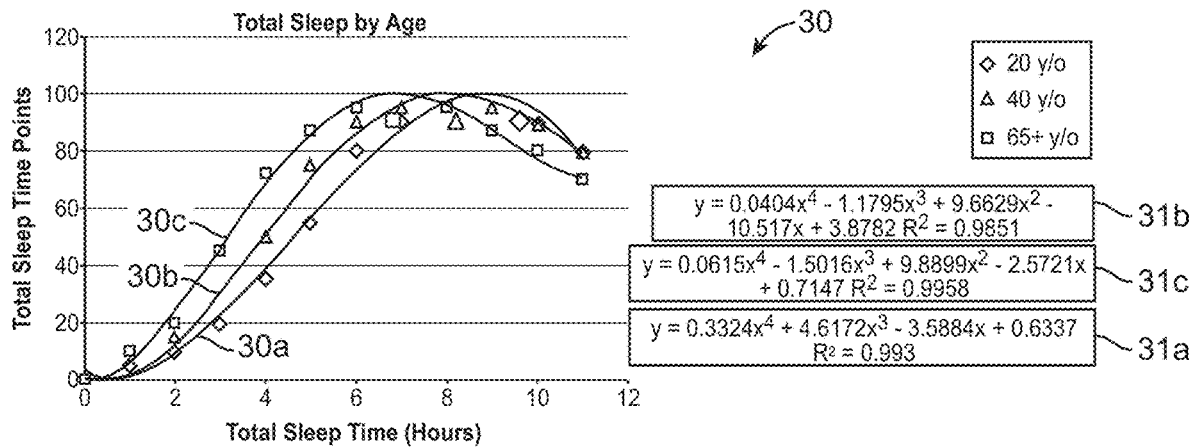
FIG. 2A illustrates a variation of total sleep reference data.
Figure 2B:
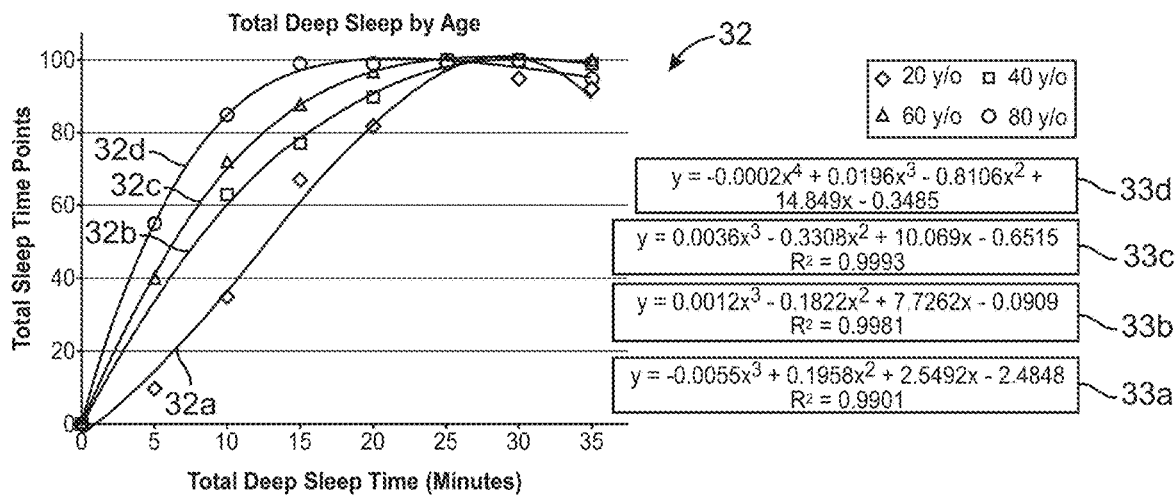
FIG. 2B illustrates a variation of total deep sleep reference data.
Figure 2C:
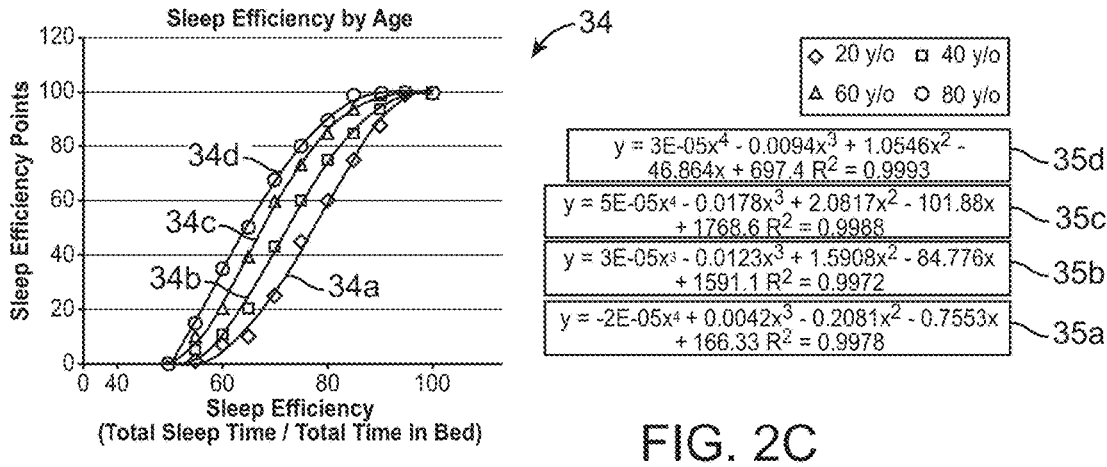
FIG. 2C illustrates a variation of sleep efficiency reference data.
Figure 2D:
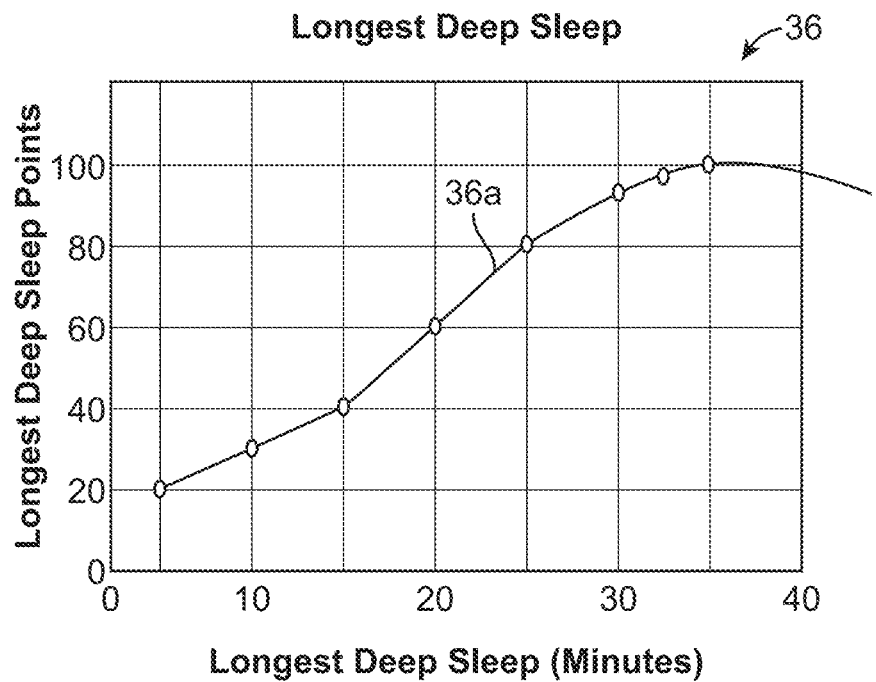
FIG. 2D illustrates a variation of longest deep sleep reference data.
Figure 2E:
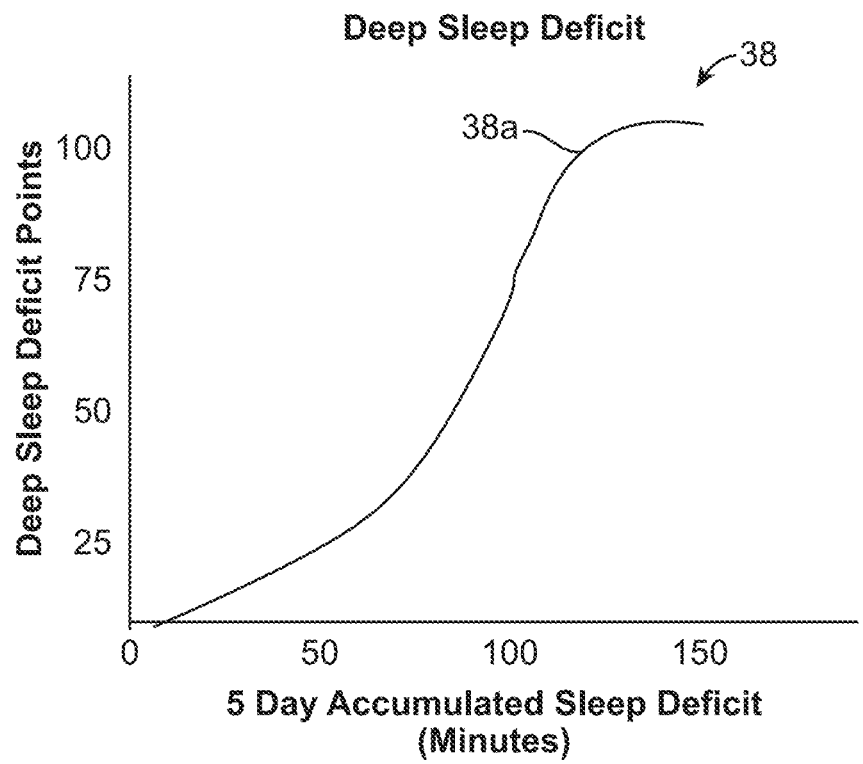
FIG. 2E illustrates a variation of deep sleep deficit reference data.

FIGS. 2A-2E illustrate variations of reference data sets that the system 10 can have stored in memory (e.g., a database). Specifically, FIGS. 2A-2E illustrate graphs of total sleep, total deep sleep, sleep efficiency, longest deep sleep, and deep sleep deficit data, respectively. FIGS. 2A-2C further illustrate that the total sleep, total deep sleep, and sleep efficiency data can each have multiple age cohort curves (also referred to as reference curves). For example, FIG. 2A illustrates a variation of a total sleep graph 30 having age-cohort curves 30a, 30b, 30c for ages 20 years old, 40 years old, and 65+ years old (i.e., 65 years old and greater), respectively. The total sleep curves 30a, 30b, 30c can have polynomial equations, for example polynomial equations 31a, 31b, 31c, respectively. FIG. 2B illustrates a variation of a total deep sleep graph 32 having age-cohort curves 32a, 32b, 32c, 32d for ages 20 years old, 40 years old, and 60 years old, and 80 years old, respectively. The total deep sleep curves 32a, 32b, 32c, 32d can have polynomial equations, for example polynomial equations 33a, 33b, 33c, 33d, respectively. FIG. 2C illustrates a variation of a sleep efficiency graph 34 having age-cohort curves 34a, 34b, 34c, 34d for ages 20 years old, 40 years old, and 60 years old, and 80 years old, respectively. The sleep efficiency curves 34a, 34b, 34c, 34d can have polynomial equations, for example polynomial equations 35a, 35b, 35c, 35d, respectively. FIGS. 2D and 2E further illustrate that the longest deep sleep and deep sleep deficit data can be represented without cohort separation. For example, FIG. 2D illustrates a variation of a longest deep sleep graph 36 having a single longest deep sleep reference curve 36a. FIG. 2E illustrates a variation of a deep sleep deficit graph 38 having a single deep sleep deficit reference curve 38a. The longest deep sleep and deep sleep deficit curves can be polynomial curves as well. FIGS. 2A-2E each illustrate that the parameters/metrics can be indexed to a 0-100 point scale.

Figure 3A:
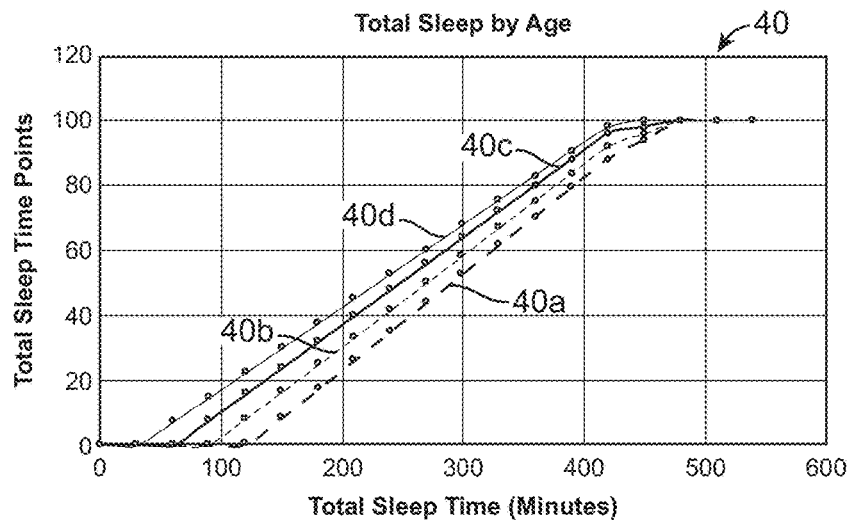
FIG. 3A illustrates a variation of total sleep reference data.
Figure 3B:
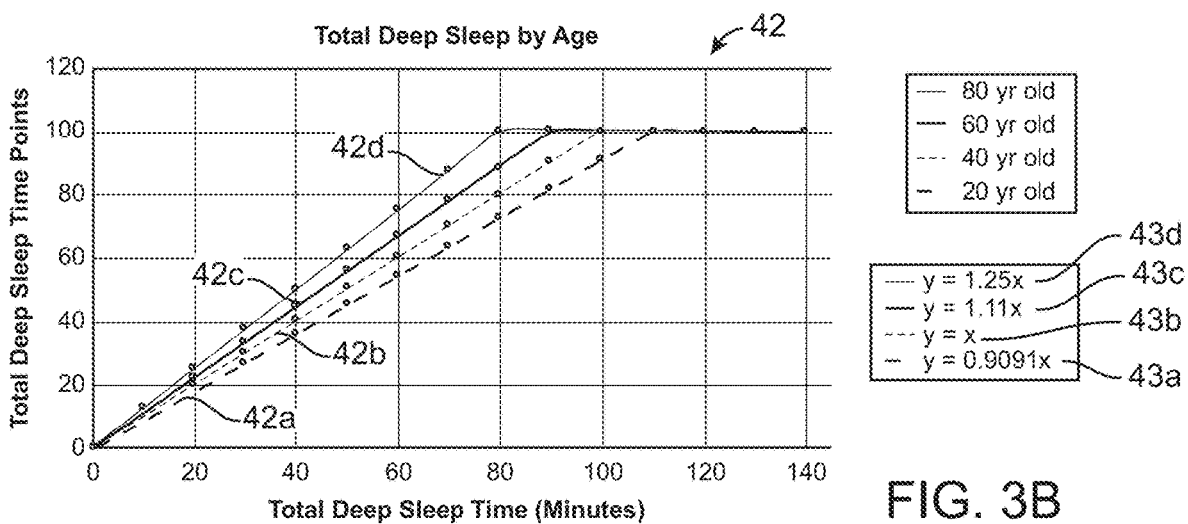
FIG. 3B illustrates a variation of total deep sleep reference data.
Figure 3C:
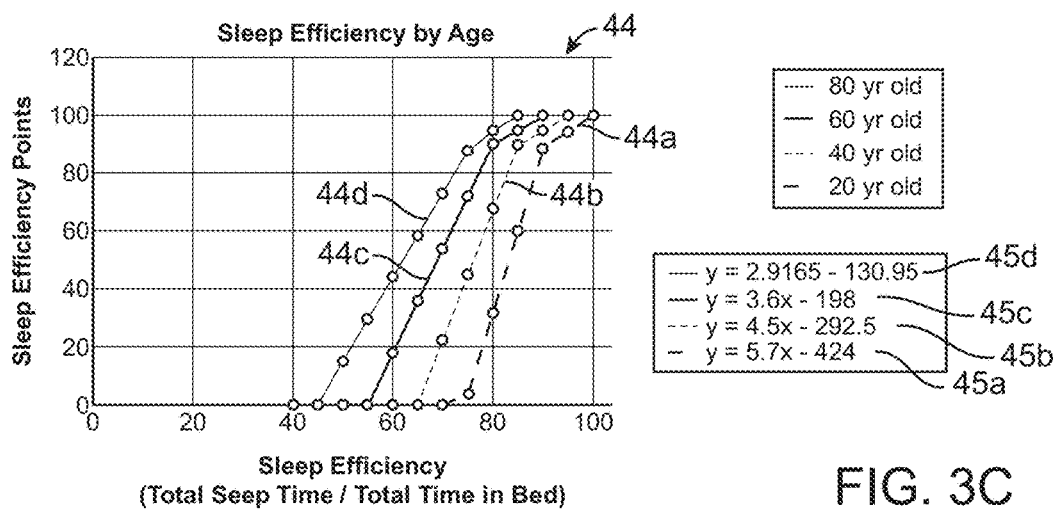
FIG. 3C illustrates a variation of sleep efficiency reference data.
Figure 3D:
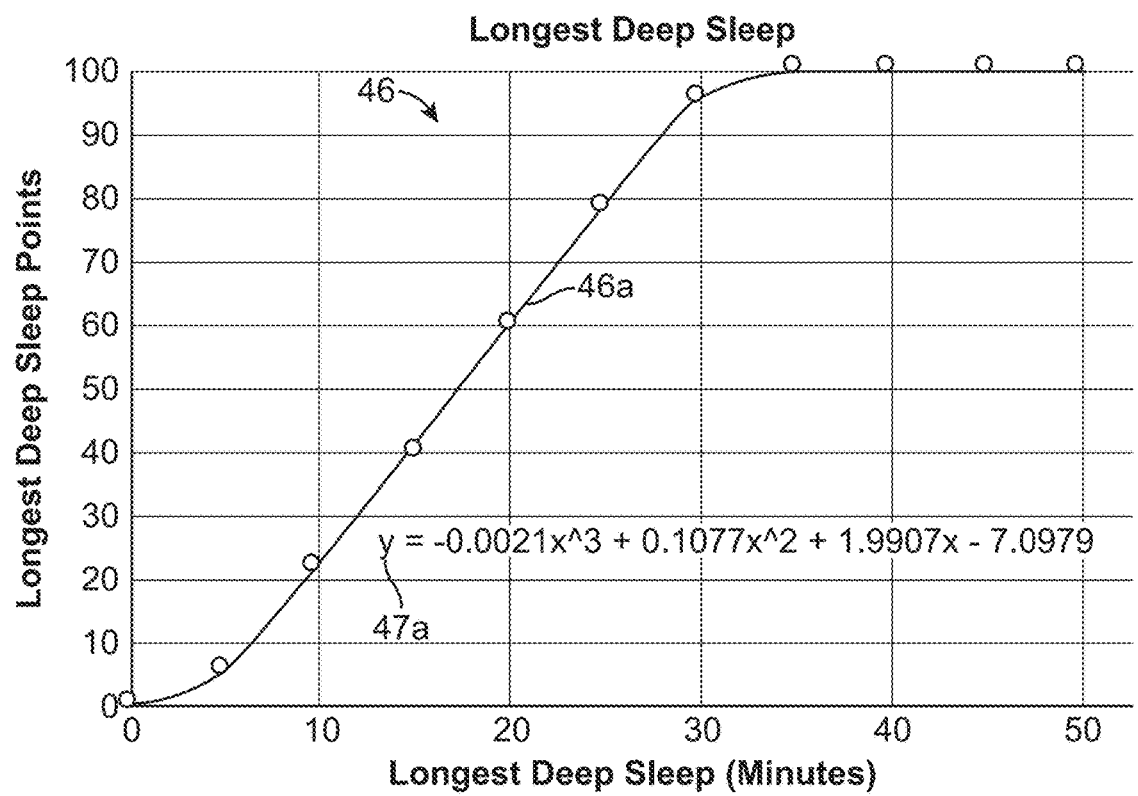
FIG. 3D illustrates a variation of longest deep sleep reference data.
Figure 3E:
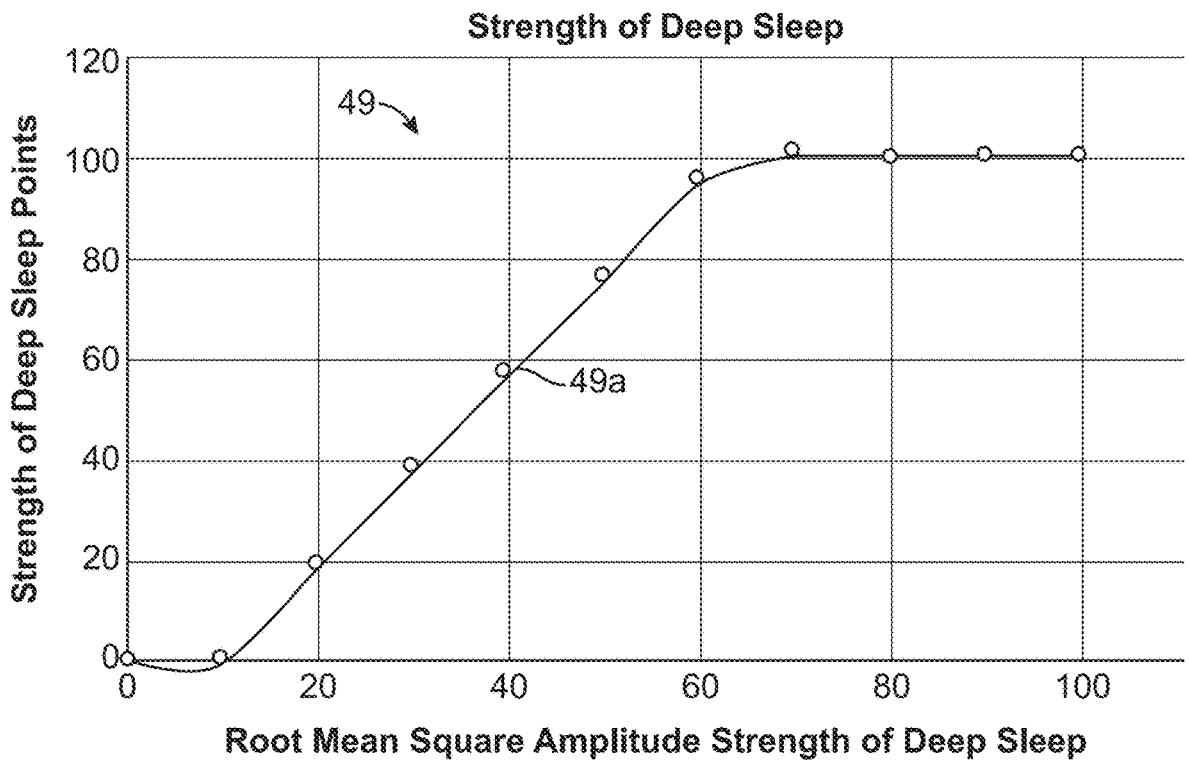
FIG. 3E illustrates a variation of strength of deep sleep reference data.

FIGS. 3A-3D illustrate variations of total sleep, total deep sleep, sleep efficiency, and longest deep sleep having non-polynomial equations. For example, FIGS. 3A-3D illustrate variations of linear approximations of the polynomial curves illustrated in FIGS. 2A-2D. For example, FIGS. 3A-3D illustrate variations of a series of connected line segments that approximate the polynomial curves illustrated in FIGS. 2A-2D. FIG. 3A further illustrates that the 65+ total sleep curve 30c has been replaced with 60 years old and 80 years old cohort curves. FIG. 3A illustrates a variation of a total sleep graph 40 having age-cohort curves 40a, 40b, 40c, 40d for ages 20 years old, 40 years old, and 60 years old, and 80 years old, respectively. The total sleep curves 40a and 40b can be linear approximations of polynomial total sleep curves 30a and 30b, respectively. FIG. 3B illustrates a variation of a total deep sleep graph 42 having age-cohort curves 42a, 42b, 42c, 42d for ages 20 years old, 40 years old, and 60 years old, and 80 years old, respectively. The total deep sleep curves 42a, 42b, 42c, 42d can have linear equations, for example linear equations 43a, 43b, 43c, 43d, respectively. The total deep sleep curves 42a, 42b, 42c, 42d can be linear approximations of polynomial total deep sleep curves 32a, 32b, 32c, 32d, respectively. FIG. 3C illustrates a variation of a sleep efficiency graph 44 having age-cohort curves 44a, 44b, 44c, 44d for ages 20 years old, 40 years old, and 60 years old, and 80 years old, respectively. The sleep efficiency curves 44a, 44b, 44c, 44d can have linear equations, for example linear equations 45a, 45b, 45c, 45d, respectively. The sleep efficiency curves 44a, 44b, 44c, 44d can be linear approximations of polynomial total deep sleep curves 34a, 34b, 34c, 324, respectively. FIG. 3D illustrates a variation of a longest deep sleep graph 46 having a single longest deep sleep reference curve 46a. FIG. 3E illustrates a variation of a reference data set that the system 10 can have stored in memory (e.g., a database). Specifically, FIG. 3E illustrates a graph of strength of deep sleep data. For example, FIG. 3E illustrates a variation of a strength of deep sleep graph 49 having a single strength of deep sleep reference curve 49a. FIG. 3E illustrates that the strength of deep sleep can be a function of the root mean square (RMS) of the amplitude of SWS. The RMS of the amplitude can be a measure of the strength/deepness of deep sleep. FIGS. 3D and 3E further illustrate that the longest deep sleep and strength of deep sleep data can be represented without cohort separation. The longest deep sleep and strength of deep sleep curves can be polynomial and/or linear curves. For example, the longest deep sleep curve 46a can be a linear approximation of the polynomial longest deep sleep curve 36a. Additionally or alternatively, FIG. 3D illustrates that the longest deep sleep curve 46a can have a polynomial equation 47a. FIGS. 3A-3E each illustrate that the parameters/metrics can be indexed to a 0-100 point scale.

Extrapolation techniques such as weighted averages can be used to determine the points (i.e., the value on the y-axis) in FIGS. 2A-3E where there is one or more cohort curves (e.g., in FIGS. 2A-2C and FIGS. 3A-3C).

The system 10 can generate and/or have reference heart rate variability (HRV) data. For example, the system 10 can measure the R-R intervals of a user's heart beats. The R-R intervals can correspond to the times between heartbeats. The system 10 can calculate the root mean square of the successive differences (RMSSD) of the R-R intervals. The system 10 can measure the R-R intervals of a user's heart beats in one or more time periods. For example, the system 10 can measure RMSSD in a first RMSSD calculation period and in a second RMSSD calculation period. The first RMSSD calculation period can correspond to the RMSSD during the first 1 to 10 minutes of light sleep (e.g., the first 5 minutes of light sleep). The second RMSSD calculation period can correspond to the RMSSD during the last 1 to 15 minutes of light sleep before waking up (e.g., the last 5 minutes of light sleep before waking up). The RMSSD of the R-R can provide a beat-to-beat variability of the user's heart.

Figure 4A:
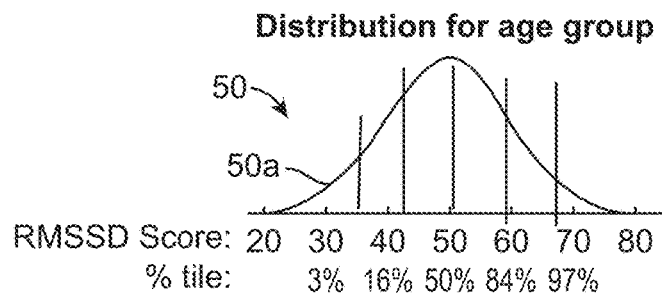
FIG. 4A illustrates a variation of a data set generatable/generated by the system of FIG. 1A.
Figure 4B:
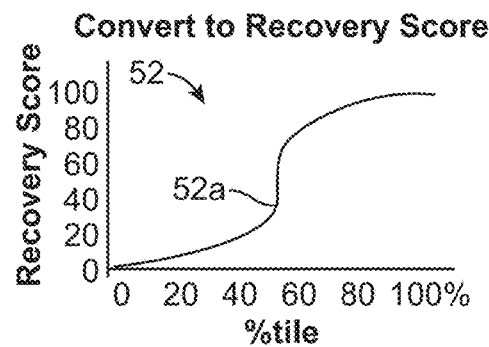
FIG. 4B illustrates a variation of RMSSD reference data.
Figure 4C:
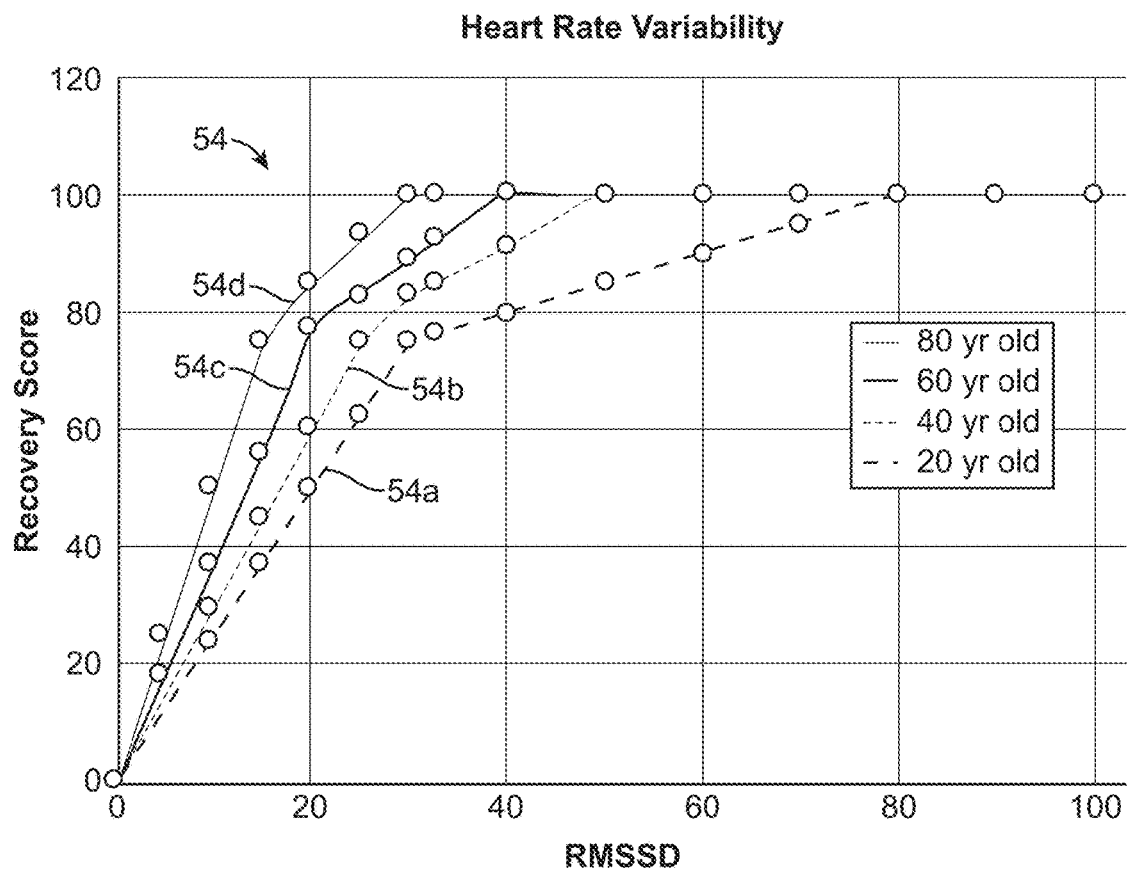
FIG. 4C illustrates a variation of RMSSD reference data.

FIGS. 4A-4C illustrate variations of heart rate variability (HRV) data that the system 10 can generate and/or have stored in memory. FIG. 4A illustrates a variation of a reference data set that the system 10 can generate when determining a sleep performance score (e.g., the recharge score), and/or have stored in memory. Specifically, FIG. 4A illustrates a variation of a standard deviation graph 50 having a distribution curve 50a. As shown in FIG. 4A, the RMSSD score and percentile can be on the x-axis. The standard deviation curve 50a can be a user's historical ending RMSSD of the R-R intervals of the user's heart. The standard deviation curve 50a can be a cohort curve (e.g., an age, gender, ethnicity, health, and/or fitness level cohort curve). FIG. 4A illustrates that the distribution curve 50a can be an age cohort curve. The distribution curve 50a can be, for example, a curve corresponding to an age of 20 years old, 40 years old, 60 years old, 80 years old, and/or 65+ years old.

FIGS. 4B and 4C illustrate variations of reference data sets that the system 10 can have stored in memory. Specifically, FIG. 4B illustrates a variation of a percentile graph 52 having a curve 52a that can be used to determine the total recovery points. The percentile (e.g., 0%, 20%, 40%, 60%, 80%, 100%) can correspond to the one or more of the percentage-tiles associated with the HRV distribution curve of FIG. 4A. FIG. 4B further illustrates that the RMSSD of a user (e.g., during their last 5 minutes of light sleep before waking up) can be indexed to a 0-100 point scale. FIG. 4C illustrates a variation of an RMSSD distribution graph 54 having age-cohort curves 54a, 54b, 54c, 54d for ages 20 years old, 40 years old, 60 years old, and 80 years old, respectively. The RMSSD curves 54a, 54b, 54c, 54d can be used to determine the total recovery points. FIG. 4C further illustrates that the RMSSD data can have multiple age cohort curves. FIG. 4C further illustrates that the RMSSD of a user (e.g., during their last 5 minutes of light sleep before waking up) can be indexed to a 0-100 point scale. The system 10 can reference the non-cohort data of FIG. 4B and/or the cohort data of FIG. 4C when determining the total recovery points. The system 10 can reference the data of FIG. 4B when there a sufficient number of data points to generate the plot of FIG. 4A, for example, when there are more than 3 to 5 nights of data. The system 10 can reference the data of FIG. 4C when there is an insufficient number of data points to generate the plot of FIG. 4A, for example, when there are less than 3 to 5 nights of data.

Extrapolation techniques such as weighted averages can be used to determine the points (i.e., the value on the y-axis) in FIGS. 2A-4C where there is one or more cohort curves (e.g., in FIGS. 2A-2C, FIGS. 3A-3C, and FIG. 4C).

Sleep Quality Score

The sleep quality score can be a function of one or multiple variables, for example, 1 to 5 or more variables, including every 1 variable increment within this range (e.g., 3 variables). For example, the sleep quality score can be a function of total sleep parameter, total deep sleep parameter, and sleep efficiency parameter, or any combination thereof. The total sleep parameter, total deep sleep parameter, and sleep efficiency parameter can be used to determine total sleep points, total deep sleep points, and sleep efficiency points, respectively. The system 10 can determine these points by referencing cohort and/or non-cohort data. Such data can be represented as a graph and can be stored in a memory (e.g., the data sets illustrated in FIGS. 2A-2C and/or FIGS. 3A-3C). The sleep quality score variables and/or the total points associated with each variable can be weighted. For example, the total sleep points can have a weight of about 25% to about 75%, including every 1% increment within this range (e.g., 40%, 50%). The total deep sleep points can have a weight of about 25% to about 75%, including every 1% increment within this range (e.g., 40%, 50%). The sleep efficiency points can have a weight of about 1% to about 51%, including every 1% increment within this range (e.g., 10%, 20%) For example, the sleep quality score can have a total sleep points weight—total deep sleep variable weight—sleep efficiency variable weight of about 40%-40%-20%, about 50%-40%-10%, about 50%-35%-15%. The sleep quality variables can have the same or different weights than the total sleep quality point weights.

The sleep quality score can be calculated by adding the total sleep time parameter, deep sleep parameter, and sleep efficiency parameter. The sleep quality score can be calculated by weighing the total sleep time parameter by 40%, deep sleep parameter by 40%, and sleep efficiency parameter by 20%. For example, the sleep quality score can be calculated with the following equation: Sleep Quality Score=50% (Total Sleep Time Parameter)+40% (Longest Deep Sleep Parameter)+10% (Sleep Efficiency Parameter).

Additionally or alternatively, the sleep quality score can be a function of sleep stage balance, number of sleep disruptions, and magnitude of sleep disruptions. The system 10 can calculate one or more sleep quality scores (e.g., 1 to 5 or more sleep quality scores). For example, the system 10 can calculate a first sleep quality score and a second sleep quality score. The first sleep quality score can be a function of total sleep time parameter, total deep sleep parameter, and sleep efficiency parameter. The second sleep quality score can be a function of sleep stage balance, number of sleep disruptions, and magnitude of sleep disruptions.

The sleep quality score can be an objective and trackable measure of sleep performance. For example, the sleep quality score can be an objective and trackable measure of deep sleep quality. The system 10 can improve deep sleep quality, for example, by specifically targeting deep sleep by making one or more observations and/or recommendations to a user based on the sleep quality score and/or on one or more values of SWS-related parameters. For example, the system 10 can improve deep sleep by providing a user with one or more ways to improve their sleep quality score or one or more parameters related to SWS (e.g., audio stimulation, visual stimulation, cranial electrical stimulation, behavioral modification suggestions (e.g., "drink less coffee 4 hours before bed"), user awareness observations (e.g., "your stress level appears high"), guided relaxation/meditation). The sleep performance systems 10 can recommend and/or activate sleep improvement programs based on various threshold scores related to the sleep quality score, or based entirely on the sleep quality score.

Brain Fitness Score

The brain fitness score can be a function of one or multiple variables, for example, 1 to 5 or more variables, including every 1 variable increment within this range (e.g., 3 variables). For example, the brain fitness score can be a function of total deep sleep parameter, longest deep sleep parameter, and deep sleep strength parameter, or any combination thereof. The total deep sleep, longest deep sleep duration, and deep sleep strength can each be used to determine total deep sleep points, longest deep sleep duration points, and deep sleep strength points, respectively. The system 10 can determine these points by referencing cohort and/or non-cohort data. Such data can be represented as a graph and can be stored in a memory (e.g., the data sets illustrated in FIGS. 2B, 2D and 2E and/or FIGS. 3B, 3D and 3E). The brain fitness score variables and/or the total points associated with each variable can be weighted. For example, the total deep sleep points can have a weight of about 50% to about 100%, including every 1% increment within this range (e.g., 80%). The longest deep sleep points can have a weight of about 1% to about 51%, including every 1% increment within this range (e.g., 10%). The deep sleep strength points can have a weight of about 1% to about 51%, including every 1% increment within this range (e.g., 10%). For example, the brain fitness score can have a total deep sleep points weight—longest deep sleep points weight—deep sleep strength points weight of about 80%-10%-10%, about 75%-15%-10%, about 70%-15%-15%, about 40%-40%-20%. The brain fitness score can also be a function of deep sleep amplitude. The system 10 can convert the deep sleep amplitude variable into an indexed point value between 0 and 100. The deep sleep amplitude points can have a weight of about 1% to about 51%, including every 1% increment within this range (e.g., 5%, 10%, 15%, 20%). For example, the brain fitness score can be a function of total deep sleep parameter, longest deep sleep parameter, deep sleep strength parameter, and deep sleep amplitude parameter, or any combination thereof.

The brain fitness score can be calculated by adding the total deep sleep time parameter, longest deep sleep parameter, and deep sleep deficit parameter. The brain fitness score can be calculated by weighting the total deep sleep time parameter by 80%, longest deep sleep parameter by 10%, and deep sleep deficit parameter by 10%. For example, the brain fitness score can be calculated with the following equation: Brain Fitness Score=80% (Total Deep Sleep Time Parameter)+10% (Longest Deep Sleep Parameter)+10% (Deep Sleep Deficit Parameter).

The brain fitness score can be calculated by adding the total deep sleep time parameter, longest deep sleep parameter, and deep sleep strength parameter. The brain fitness score can be calculated by weighting the total deep sleep time parameter by 80%, longest deep sleep parameter by 10%, and deep sleep strength parameter by 10%. For example, the brain fitness score can be calculated with the following equation: Brain Fitness Score=80% (Total Deep Sleep Time Parameter)+10% (Longest Deep Sleep Parameter)+10% (Deep Sleep Strength Parameter).

The brain fitness score can be an objective and trackable measure of sleep performance. For example, the brain fitness score can be an objective and trackable measure of deep sleep quality. The system 10 can improve deep sleep quality, for example, by specifically targeting deep sleep by making one or more observations and/or recommendations to a user based on the brain fitness score and/or on one or more values of SWS-related parameters. For example, the system 10 can improve deep sleep by providing a user with one or more ways to improve their brain fitness score or one or more parameters related to SWS (e.g., audio stimulation, visual stimulation, cranial electrical stimulation, behavioral modification suggestions (e.g., "drink less coffee 4 hours before bed"), user awareness observations (e.g., "your stress level appears high"), guided relaxation/meditation). The sleep performance system 10 can recommend and/or activate sleep improvement programs based on various threshold scores related to the brain fitness score, or based entirely on the brain fitness score.

Recharge Score

The recharge score (also referred to as the recovery score) can be a function of one or multiple variables, for example, 1 to 5 or more variables, including every 1 variable increment within this range (e.g., 1 variable). The recharge score can be a function of a user's HRV. For example, the recharge score can measure how much the HRV increases during sleep. The recharge score can be a function of a user's RMSSD of their R-R intervals. The calculated RMSSD can be used to determine the number of recovery points associated with any given RMSSD value (e.g., the RMSSD values can correspond to a percentile of the standard deviation distribution 50a of FIG. 4A). For example, the recharge score can be the previous night RMSSD score as a percentile of a user's personal RMSSD distribution (e.g., the graph 50 of FIG. 4A). The system 10 can determine these points by referencing cohort and/or non-cohort data. Such data can be represented as a graph and can be generated and/or can be stored in a memory (e.g., the data sets illustrated in FIGS. 4A, 4B and/or 4C). The recovery points determined from the reference data in FIGS. 4B and 4C can be the recharge score. The RMSSD can be the only input into the recovery score, for example, by being translated into a 0-100 point scale. Alternatively or additionally, the recharge points can be weighted with one or more other variables, for example, total sleep parameter, total deep sleep parameter, longest deep sleep parameter, deep sleep amplitude parameter, or any combination thereof. Each of these variables, including the RMSSD variable, can have a weight of about 1% to about 95%, including every 1% increment within this range (e.g., 20% each). For example, the RMSSD variable can have a weight of about 50% to about 95%, including every 1% increment within this range (e.g., 80%), with one or more other variables having a 5% to 50% weight (depending on the number of additional variables).

Influencers Score

The system 10 can monitor and keep track of factors that affect a user's sleep. For example, the system 10 can keep track of a user's behaviors and monitor the various effects that these behaviors have on the user's sleep. The behaviors can include good and/or bad activities (also referred to individually and collectively as influencers/sleep factors). Positive (or good) influencers can positively affect a user's sleep. Positive influencers can manifest in one or more of a user's sleep performance scores, for example, by increasing the score, by increasing the score more quickly than without the positive behavior, by not decreasing the score, or by decreasing the score more slowly than without the positive behavior. Negative (or bad) influencers can negatively affect a user's sleep. Negative influencers can manifest in one or more of a user's sleep performance scores, for example, by decreasing the score, by decreasing the score more quickly than without the negative behavior, by not increasing the score, or by increasing the score more slowly than without the negative behavior.

The influencers can include factors such as audio stimulation, visual stimulation, cranial electrical stimulation, exercise, caffeine, alcohol, stress, quiet time, marijuana, coffee, tea, breathing exercises, meditation, listening to music, naps (e.g., time and duration of naps), diet, time of dinner (e.g., late dinner), nicotine, TV in bed, sugar, heavy/spicy foods, consistent bed time, bedtime tea, water, ear plugs/white noise, bath/shower, sleep medications, room temperature, flu/sick, jet lag, drank alcohol, complex carbohydrates before bed, melatonin, glass of water before bed, light meal, shower/bath before bed, TV before bed, computer/phone before bed, weather, or any combination thereof. A user can add their own factors/behaviors/influencers such that the influencer list can be partly or completely determined by user input. The system 10 can monitor from 0 to 100 or more positive influencers (e.g., 55 positive influencers). The system 10 can monitor from 0 to 100 or more negative influencers (e.g., 23 negative influencers).

The system 10 (e.g., the device 12, the device 20, and/or a remote server) can perform multivariate regression of the various behaviors/influencers (e.g., audio stimulation, exercise, caffeine, alcohol, stress, quiet time) on one or more of the sleep performance scores too determine the relative impact of each influencer on that performance score. An influencer can impact different sleep performance scores the same or differently (e.g., by increasing or decreasing it). For example, the system 10 can perform multivariate regression on the various behaviors/influencers (e.g., audio stimulation, exercise, caffeine, alcohol, stress, quiet time) on the sleep quality score to determine the relative impact of each on the sleep quality score. The influencers score can be a coefficient of variables to the sleep performance scores (e.g., the sleep quality score).

Observations and Recommendations—Ah Ha's

The system 10 can make sleep related observations and recommendations based on an analysis of one or more factors (e.g., influencers). The observations can also be referred to as performance insights, things worth noting, things worth mentioning, or "AH-HA's."

The observations can be tied to one or more determined parameters and/or to one or more sleep performance metrics (e.g., derivations involving one or more determined parameters). As described above, the observations can provide text summaries of a user's sleep performance (e.g., "insufficient total deep sleep"), as well as insights related to the user's sleep performance (e.g., "high stress levels," "high stress levels detected"). The recommendations can include goal suggestions related to one or more influencers of the user's sleep performance. The influencers can be variables and/or behaviors that can, may, and/or do affect sleep generally and/or the user's sleep specifically. For example, the system 10 can provide recommendations such as "smoke one less cigarette today," "go for a 10-20 minute walk at 7 pm," "have your Wednesday glass of wine 30 minutes earlier today," "plan something fun for this weekend".

Table 1 below (next page) illustrates various factors (e.g., sleep quality factors) having various exemplary thresholds/events that trigger the listed exemplary observations and recommended programs. Table 1 further illustrates that not every observation needs to have a corresponding recommended action. Although Table 1 lists only 1 Ah-Ha with each factor, the system 10 can have 2 to 8 observations associated with each factor (e.g., 4 observations). The system 10 can then rotate the observations displayed to the user (e.g., using the device 20) on different days so that if the user has the same high-scoring or low-scoring factor repeatedly, the user will see different "ah-ha's" for the same factor to inhibit or help prevent the user from becoming bored of the device 12 and/or to encourage the user to keep using the device 12. Although Table 1 lists only 1 recommended action associated with each factor, the system 10 can have 2 to 8 recommended actions associated with each factor (e.g., 4 recommended actions). The system 10 can then rotate the recommendations displayed to the user (e.g., using the device 20) on different days so that if the user has the same high-scoring or low-scoring factor repeatedly, the user will see different recommendations for the same factor to inhibit or help prevent the user from becoming bored of the device 12 and/or to encourage the user to keep using the device 12.

TABLE 1

Sleep Quality Ah-Ha's and Recommendations

| Factor/Indicator | Observation (Ah-Ha) | Recommended Action |
|---|---|---|
| Total Sleep Points <80 points | Insufficient Total Sleep | None |
| Total Deep Sleep Points <80 points | Total Deep Sleep Insufficient | Audio Entrainment to Increase Sleep Quality by Increasing Deep Sleep |
| Sleep Efficiency <75% | Poor Sleep Efficiency | Guided Relaxation/Meditation |
| Time to Fall Asleep >20 min | Time to Fall Asleep Too Long | Guided Relaxation/Meditation |
| Time Awake During Night >40 min | Time Awake During Night Too Long | Guided Relaxation/Meditation |
| Sleep Cycle Interrupted at Stage 1, 2, 3, 4, or 5 | Possible Sleep Interruption Observed | None |

As Table 1 illustrates, the system 10 can determine the observations and recommendations via a lookup table. The lookup table can be stored in a memory (e.g., of the device 12, the device 20, of a remote server). One or more of the factors in the lookup table can be based on points associated with sleep parameters/metrics and/or sleep performance scores. The factors column lists the threshold values or events (e.g., sleep stage interruption) necessary to trigger the associated observation(s) and recommended action(s). The system 10 can recommend and/or activate a program based on the various threshold values and/or events in Table 1.

The system 10 can generate a lookup table over time, for example, using machine learning and artificial intelligence, with comparisons of personal results versus various cohorts, personal baselines, sleep performance scores, environmental factors, genetic factors, influencers, or any combination thereof.

FIG. 5 illustrates a variation of a lookup table 59. FIG. 5 illustrates that the "Ah Ha" points can be based on a user's performance against their goal. The user can specify the goal to be either a personal benchmark or a specified cohort. The rightmost "points" column indicates the points that the system 10 can tally whenever a contributor (e.g., factor) threshold is satisfied. The points in the rightmost column are cumulative (i.e., if a user scores <65 points for a cohort, then the system 10 will tally 6 points: 3 for <75 points +3 for <65 points). Up to 2, 3, 4, 5 or more Ah Has with the greatest number of points can be shown (e.g., displayed on the data display device 20). The system 10 can recommend and/or activate the "triggered recommendations" based on the various threshold values listed in the table 59.

Method of Use

Figure 6:
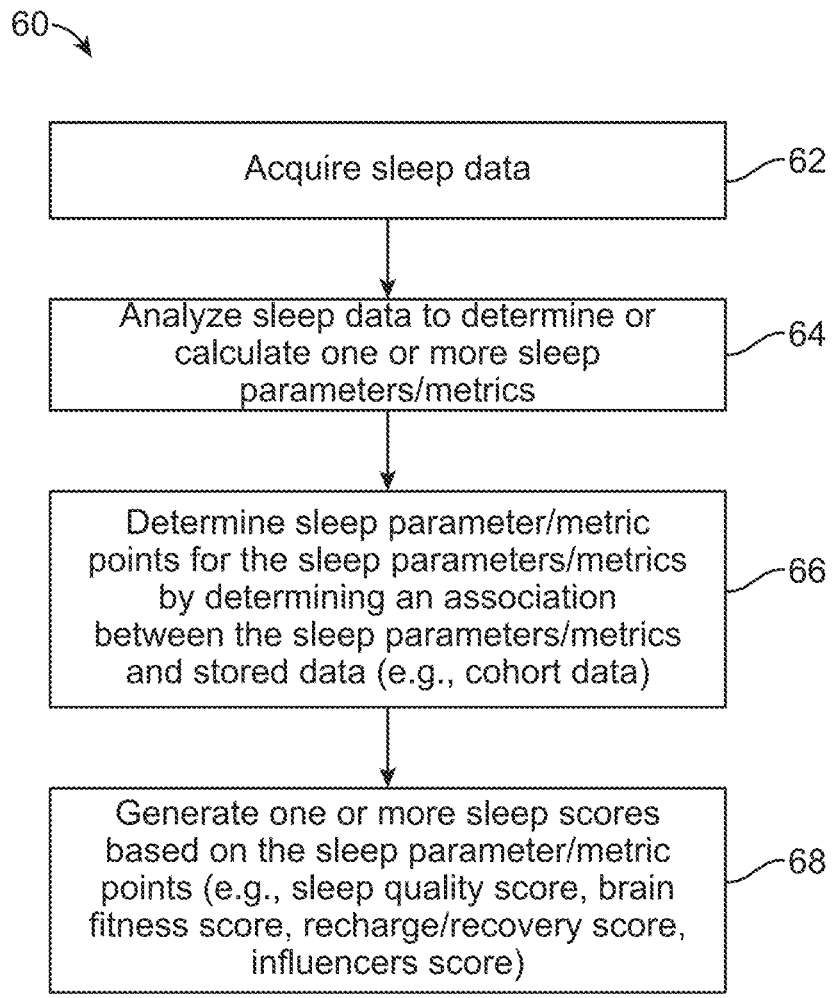
FIG. 6 illustrates a variation of a process undertaken by the system.

FIG. 6 illustrates a variation of a process 60 that is implementable using and/or performable by the system 10. The method 60 can involve acquiring sleep data in operation 62. The acquiring operation 62 can include, for example, measuring, detecting, monitoring, and/or observing one or more parameters using EEG, EOG, EMG, ECG, HRV, RIP, pulse oximetry, pressure sensors, temperature sensors, or any combination thereof.

The method 60 can further involve analyzing sleep data to determine or calculate one or more sleep parameters/metrics in operation 64.

The method 60 can further involve determining sleep parameter/metric points for the sleep parameters/metrics by determining an association between the sleep parameters/metrics and stored data (e.g., cohort data) in operation 66.

The method 60 can further involve generating one or more sleep scores based on the sleep parameter/metric points (e.g., sleep quality score, brain fitness score, recharge/recovery score, influencers score) in operation 68.

The method 60 can be an executable algorithm stored in memory that the system 10 (e.g., the device 12, the device 20, a remote server) can execute.

The system 10 can perform the method 60 every time a user uses the system 10 (e.g., at night or whenever they sleep).

Figure 7A:
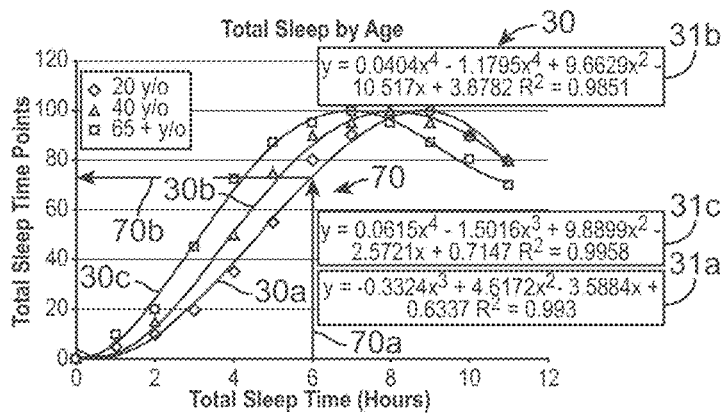
FIG. 7A illustrates a variation of a method for determining total sleep points.

FIG. 7A illustrates a variation of a method 70 for determining total sleep time points using the total sleep graph 30. The system 10 can determine the total sleep time points (y-axis) by referencing the total sleep time that the user had (x-axis), referencing the appropriate cohort curve (e.g., age cohort curve), and then determining the total sleep points associated with the total sleep time that the user had. The method 70 can involve, for example, referencing the appropriate cohort curve (e.g., age cohort curve) in operation 70a and then determining the total sleep points associated with the referenced curve in operation 70b. For example, for a 20 year old user having a total sleep time of 6 hours, the system 10 can reference the 20 years old age cohort curve 30a and determine that the total sleep points associated with 6 hours of total sleep is 74 points.

Figure 7B:
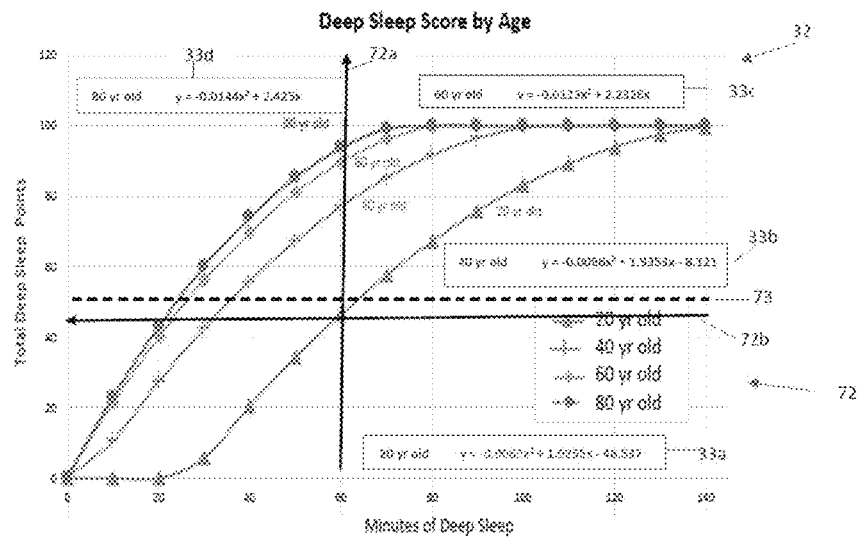
FIG. 7B illustrates a variation of a method for determining total deep sleep points.

FIG. 7B illustrates a variation of a method 72 for determining total deep sleep time points using the total deep sleep graph 32. The system 10 can determine the total deep sleep time points (y-axis) by referencing the total deep sleep time that the user had (x-axis), referencing the appropriate cohort curve (e.g., age cohort curve), and then determining the total deep sleep points associated with the total deep sleep time that the user had. The method 72 can involve, for example, referencing the appropriate cohort curve (e.g., age cohort curve) in operation 72a and then determining the total deep sleep points associated with the referenced curve in operation 72b. For example, for a 20 year old user having a total deep sleep time of 60 minutes, the system 10 can reference the 20 years old age cohort curve 32a and determine that the total deep sleep points associated with 60 minutes of total deep sleep is 46 points. FIG. 7B further illustrates that the system 10 can have an audio entrainment threshold 73 associated with the total deep sleep time points. The audio entrainment threshold 73 can be from about 0 total deep sleep time points to about 90 total deep sleep time points, including every 1 point increment within this range (e.g., 70 points, 75 points, 80 points, 85 points). When the total deep sleep points fall under the audio entrainment threshold, the system 10 can be configured to recommend audio entrainment. For example, FIG. 7B illustrates that the audio entrainment threshold 73 can be about 80 points, where any score under 80 points will trigger a recommendation by the system 10 for the user to use audio entrainment.

Figure 7C:
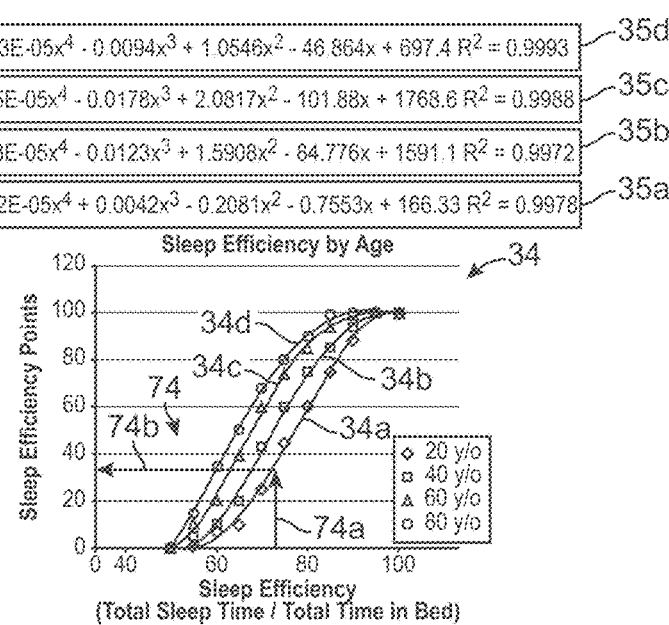
FIG. 7C illustrates a variation of a method for determining sleep efficiency points.

FIG. 7C illustrates a variation of a method 74 for determining Sleep Efficiency using the sleep efficiency graph 34. The system 10 can determine the sleep efficiency points (y-axis) by referencing the sleep efficiency that the user had (x-axis), referencing the appropriate cohort curve (e.g., age cohort curve), and then determining the sleep efficiency points associated with the sleep efficiency that the user had. The method 74 can involve, for example, referencing the appropriate cohort curve (e.g., age cohort curve) in operation 74a and then determining the total deep sleep points associated with the referenced curve in operation 74b. For example, for a 20 year old user having a sleep efficiency of 72 (e.g., 72%), the system 10 can reference the 20 years old age cohort curve 34a and determine that the sleep efficiency points associated with a sleep efficiency of 72% is 33 points.

Figure 7D:
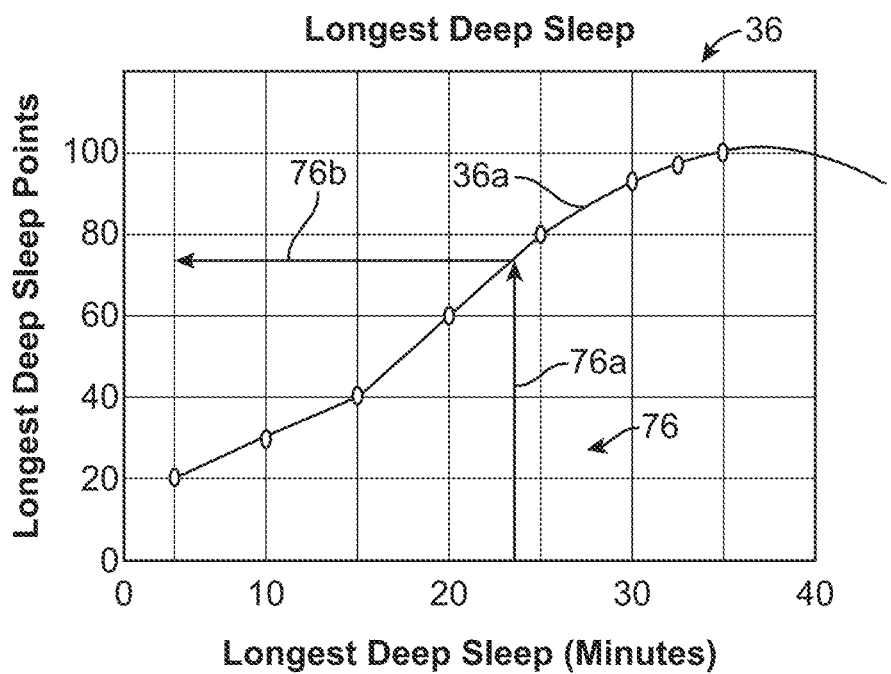
FIG. 7D illustrates a variation of a method for determining longest deep sleep points.

FIG. 7D illustrates a variation of a method 76 for determining longest deep sleep points using the longest deep sleep graph 36. The system 10 can determine the longest deep sleep points (y-axis) by referencing the longest deep sleep minutes that the user had (x-axis), referencing the appropriate curve (e.g., non-cohort or cohort-based curve), and then determining the longest deep sleep points associated with the longest deep sleep minutes that the user had. The method 76 can involve, for example, referencing the appropriate curve (e.g., non-cohort curve) in operation 76a and then determining the longest deep sleep points associated with the referenced curve in operation 76b. For example, for a 20 year old user having a longest deep sleep of 19 minutes, the system 10 can reference the curve 36a and determine that the longest deep sleep points associated with a longest deep sleep of 19 minutes is 72 points.

Figure 7E:
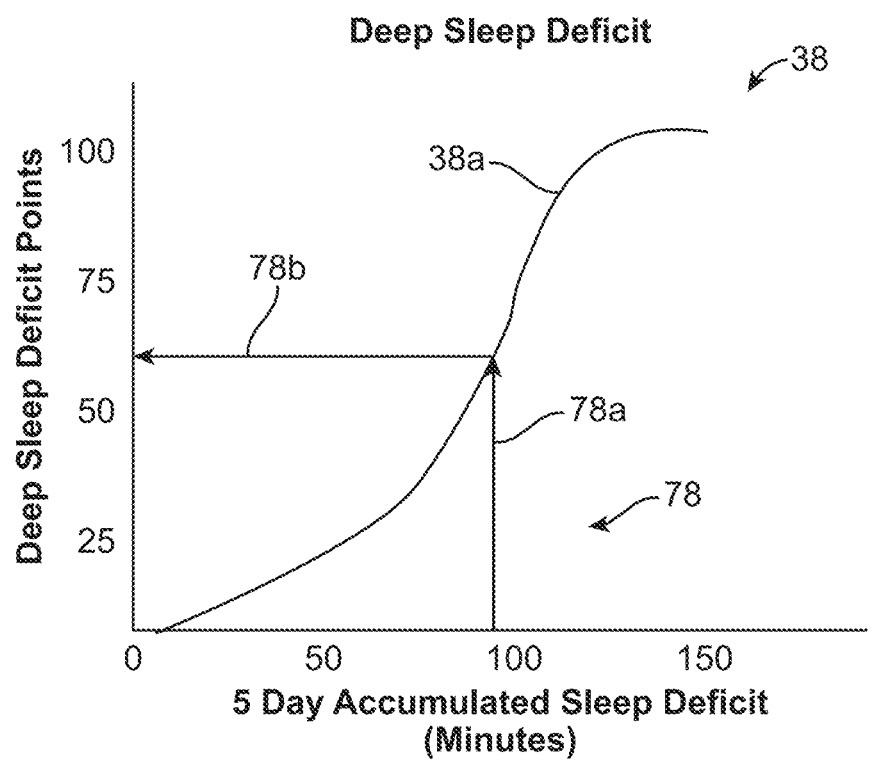
FIG. 7E illustrates a variation of a method for determining deep sleep deficit points.

FIG. 7E illustrates a variation of a method 78 for determining deep sleep deficit points using the deep sleep deficit graph 38. The system 10 can determine the deep sleep deficit points (y-axis) by referencing the 5-day accumulated sleep deficit minutes that the user has (x-axis), referencing the appropriate curve (e.g., non-cohort or cohort-based curve), and then determining the deep sleep deficit points associated with the 5-day accumulated sleep deficit minutes that the user has. The method 78 can involve, for example, referencing the appropriate curve (e.g., non-cohort curve) in operation 78a and then determining the deep sleep deficit points associated with the referenced curve in operation 78b. For example, for a 20 year old user having a deep sleep deficit of 100 minutes, the system 10 can reference the curve 38a and determine that the deep sleep deficit points associated with a 5-day accumulated sleep deficit of 100 minutes is 57 points.

FIGS. 8A-8D illustrate variations of methods 70, 72, 74, and 76 using graphs 40, 42, 44, and 46, respectively.

Figure 8A:
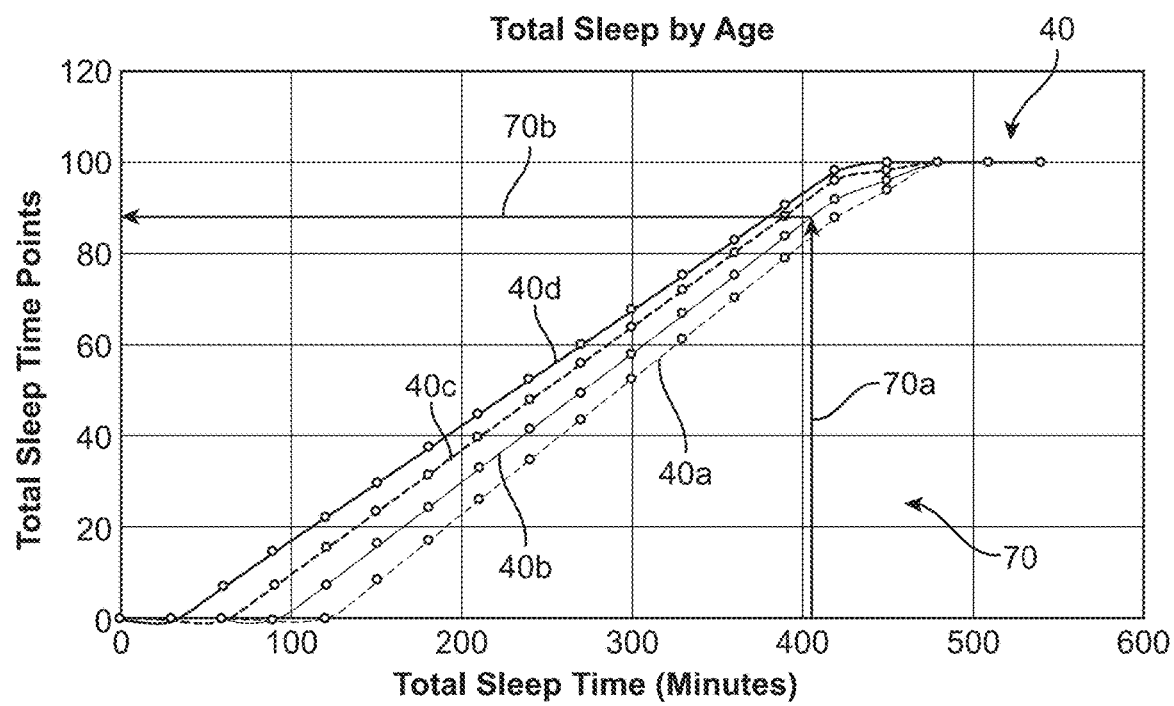
FIG. 8A illustrates a variation of a method for determining total sleep points.

For example, FIG. 8A illustrates that for a 40 year old user having a total sleep time of 405 minutes, the system 10 can reference the 40 years old age cohort curve 40a and determine that the total sleep points associated with 405 minutes of total sleep is 88 points.

Figure 8B:
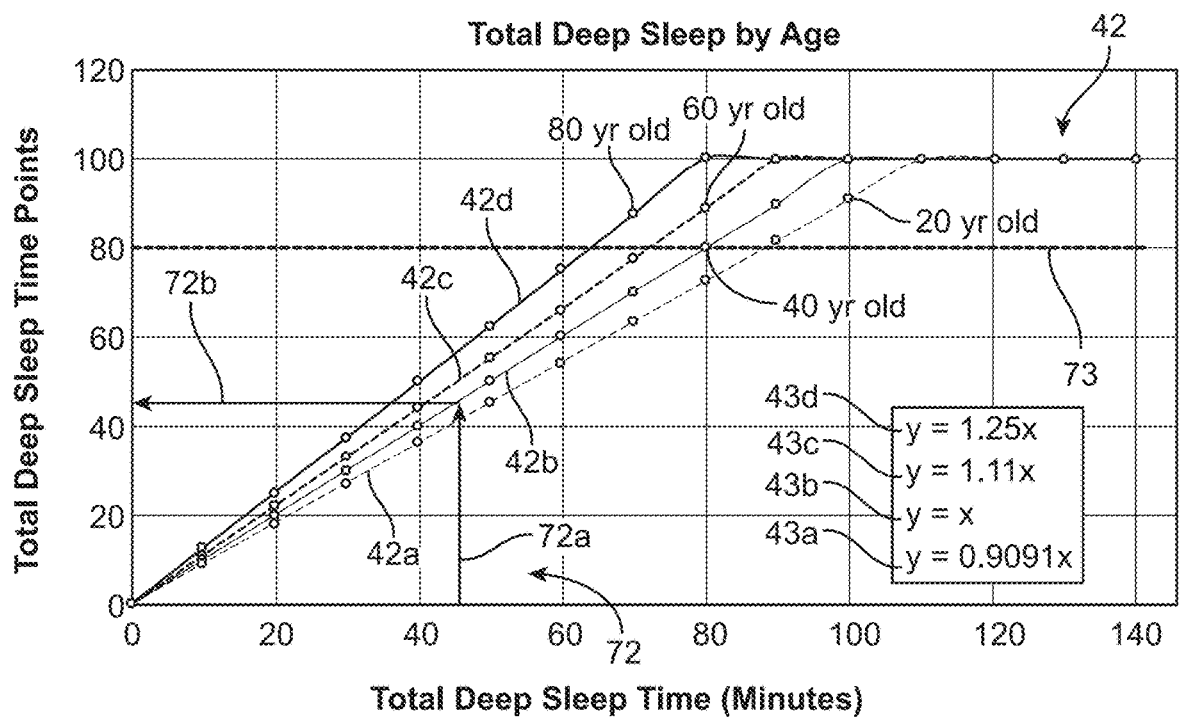
FIG. 8B illustrates a variation of a method for determining total deep sleep points.

For example, FIG. 8B illustrates that for a 40 year old user having a total deep sleep time of 45 minutes, the system 10 can reference the 40 years old age cohort curve 42a and determine that the total deep sleep points associated with 45 minutes of total deep sleep is 45 points.

Figure 8C:
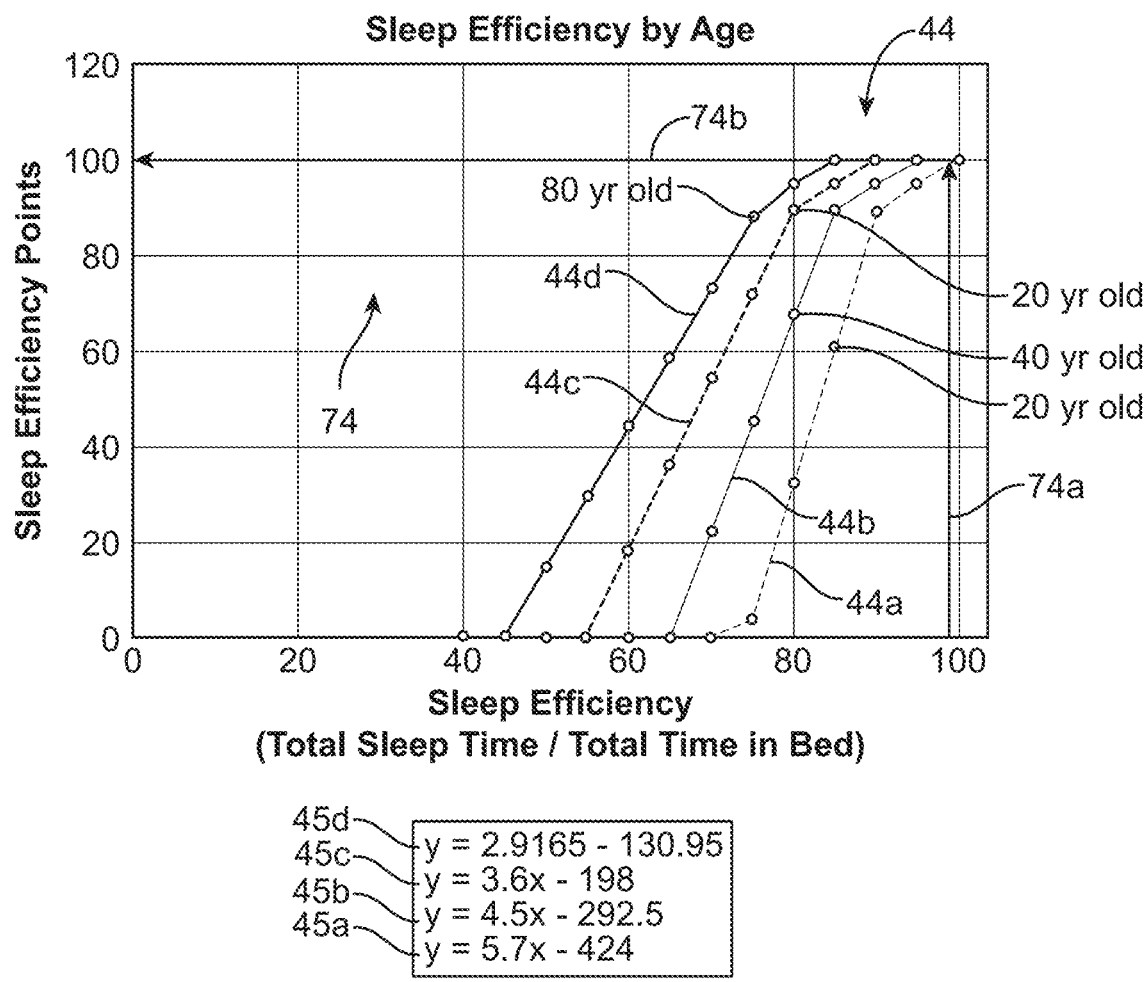
FIG. 8C illustrates a variation of a method for determining sleep efficiency points.

For example, FIG. 8C illustrates that for a 40 year old user having a sleep efficiency of 98 (e.g., 98%), the system 10 can reference the 40 years old age cohort curve 44a and determine that the sleep efficiency points associated with a sleep efficiency of 98% is 100 points.

Figure 8D:
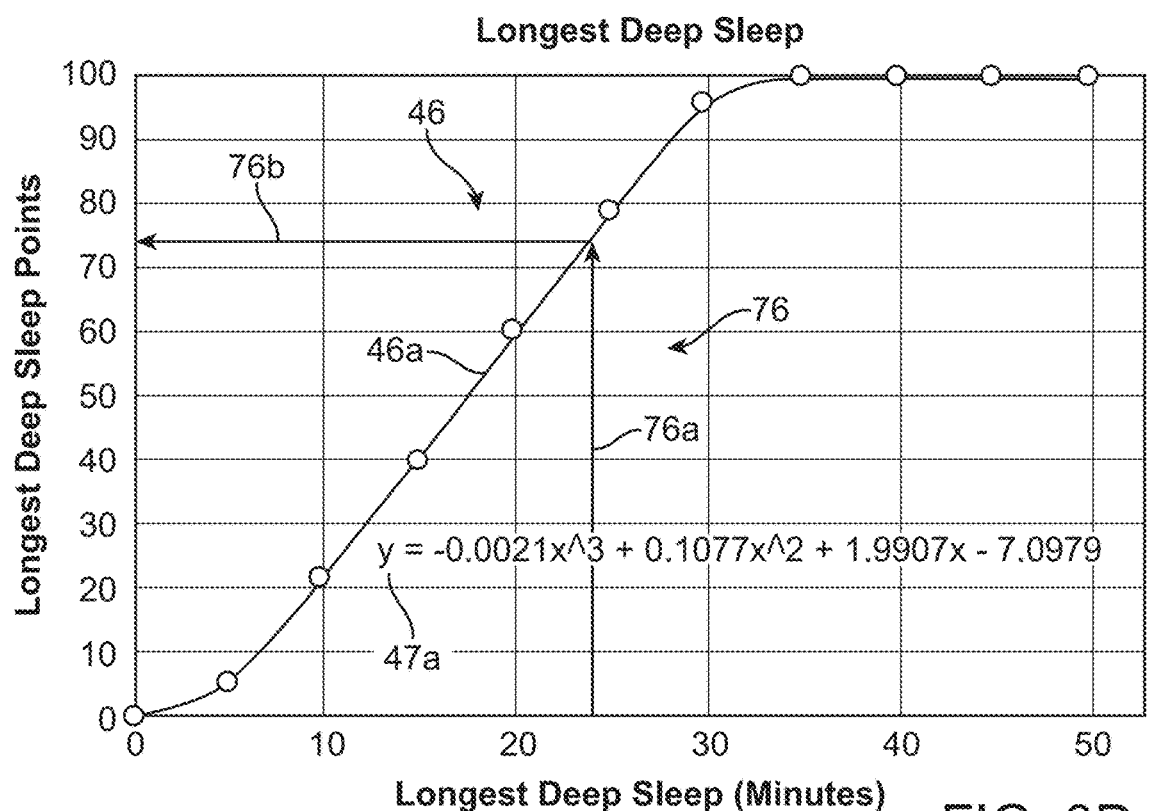
FIG. 8D illustrates a variation of a method for determining longest deep sleep points.

For example, FIG. 8D illustrates that for a 40 year old user having a longest deep sleep of 24 minutes, the system 10 can reference the curve 46a and determine that the longest deep sleep points associated with a longest deep sleep of 24 minutes is 74 points.

Figure 8E:
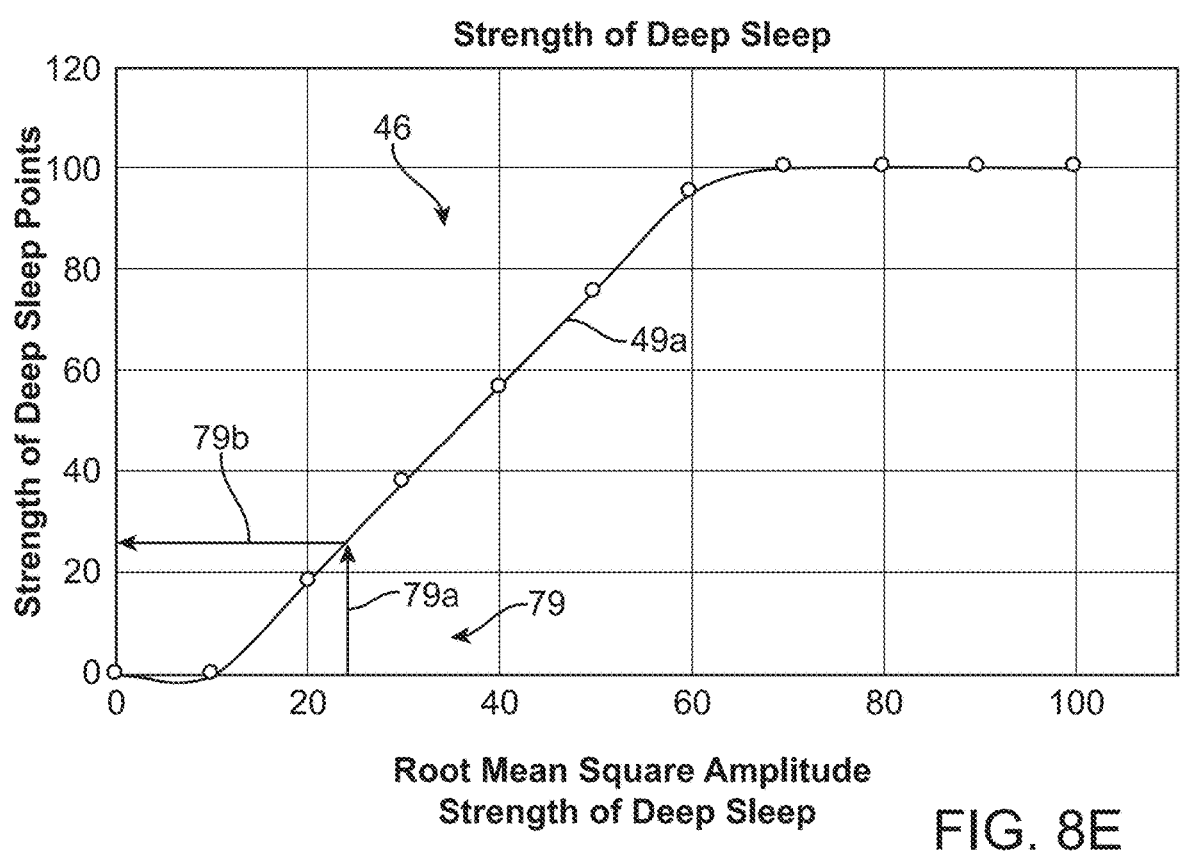
FIG. 8E illustrates a variation of a method for determining strength of deep sleep points.

FIG. 8E illustrates a variation of a method 79 for determining strength of deep sleep points using the strength of deep sleep graph 49. The system 10 can determine the strength of deep sleep points (y-axis) by referencing the RMS of SWS that the user had (x-axis), referencing the appropriate curve (e.g., non-cohort or cohort-based curve), and then determining the strength of deep sleep points associated with the RMS of SWS that the user had. The method 79 can involve, for example, referencing the appropriate curve (e.g., non-cohort curve) in operation 79a and then determining the longest deep sleep points associated with the referenced curve in operation 79b. For example, for a 40 year old user having a RMS of the amplitude of the strength of deep sleep of 22, the system 10 can reference the curve 49a and determine that the strength of deep sleep strength points associated an RMS of SWS of 22 is 26 points.

FIGS. 9A and 9B illustrate a variation of a process 80 that is implementable using and/or performable by the system 10 for determining the sleep quality score. The method 80 can involve determining the total and weighted sleep time points in operation 82, determining the total and weighted deep sleep points in operation 84, and/or determining the total and weighted sleep efficiency points in operation 86.

FIG. 9A illustrates that the operations 82, 84, and 86 can involve determining the total sleep points, total deep sleep points, and sleep efficiency points according to methods 70, 72, and 74, respectively. FIG. 9A further illustrates that the operations 82, 84, and 86 can involve weighting the total sleep points, total deep sleep points, and sleep efficiency points with weights of 40%, 40%, and 20%, respectively. FIG. 9A illustrates calculated weighted points for each of the operations 82, 84, and 86 using, for example, the points determined in the methods illustrated in FIGS. 7A-7C. FIG. 9A further illustrates that the method 80 can involve calculating the weighted points for each operation 82, 84, and 86 in operation 88. FIG. 9A further illustrates that the sleep quality score 89 can be determined by adding the weighted points determined from operations 82, 84, and 86 together. For example, FIG. 9A illustrates that the sleep quality score 89 can be 73 points using the methods and weights described.

FIG. 9B illustrates that the operations 82, 84, and 86 can involve determining the total sleep points, total deep sleep points, and sleep efficiency points according to methods 70, 72, and 74, respectively. FIG. 9B further illustrates that the operations 82, 84, and 86 can involve weighting the total sleep points, total deep sleep points, and sleep efficiency points with weights of 50%, 40%, and 10%, respectively. FIG. 9B illustrates calculated weighted points for each of the operations 82, 84, and 86 using, for example, the points determined in the methods illustrated in FIGS. 8A-8C. FIG. 9B illustrates that the sleep quality score 89 can be 72 points using the methods and weights described.

FIGS. 10A and 10B illustrate a variation of a process 90 that is implementable using and/or performable by the system 10 for determining the brain fitness score. The method 90 can involve determining the total and weighted deep sleep points in operation 92, determining the total and weighted longest deep sleep points in operation 94, and/or determining the total and weighted deep sleep deficit points and/or strength of deep sleep points in operation 86.

FIG. 10A illustrates that the operations 92, 94, and 96 can involve determining the total deep sleep points, total longest deep sleep points, and total deep sleep deficit points according to methods 72, 76, and 78, respectively. FIG. 10A further illustrates that the operations 92, 94, and 96 can involve weighting the total deep sleep points, total longest deep sleep points, and total deep sleep deficit points with weights of 80%, 10%, and 10%, respectively. FIG. 10A illustrates calculated weighted points for each of the operations 92, 94, and 96 using, for example, the points determined in the methods illustrated in FIGS. 7B, 7D, and 7E, respectively. FIG. 10A further illustrates that the method 90 can involve calculating the weighted points for each operation 92, 94, and 96 in operation 98. FIG. 10A further illustrates that brain fitness score 99 can be determined by adding the weighted points determined from operations 92, 94, and 96 together. For example, FIG. 10A illustrates that the brain fitness score 99 can be 86.5 points using the methods and weights described.

If the user does not wear the device 12 for two or more consecutive nights (e.g., 5 consecutive nights), then the deep sleep deficit metric can be excluded from the sleep performance score calculations (e.g., the brain fitness score calculation 90) and the other weightings (e.g., of the total sleep metric and the longest deep sleep metric) can be scaled up to 50% each.

FIG. 10B illustrates that the operations 92, 94, and 96 can involve determining the total deep sleep points, total longest deep sleep points, and total deep sleep strength points according to methods 72, 76, and 78, respectively. FIG. 10B further illustrates that the operations 92, 94, and 96 can involve weighting the total sleep points, total deep sleep points, and sleep efficiency points with weights of 80%, 10%, and 10%, respectively. FIG. 10B illustrates calculated weighted points for each of the operations 92, 94, and 96 using, for example, the points determined in the methods illustrated in FIGS. 8B, 8D, and 8E, respectively. FIG. 9B illustrates that the brain fitness score 99 can be 46 points using the methods and weights described.

If the user does not wear the device 12 for two or more consecutive nights (e.g., 5 consecutive nights), then the strength of deep sleep metric can be excluded from the sleep performance score calculations (e.g., the brain fitness score calculation 90) and the other weightings (e.g., of the total sleep metric and the total longest deep sleep metric) can be scaled up to 50% each.

User Interface

Figure 11A:
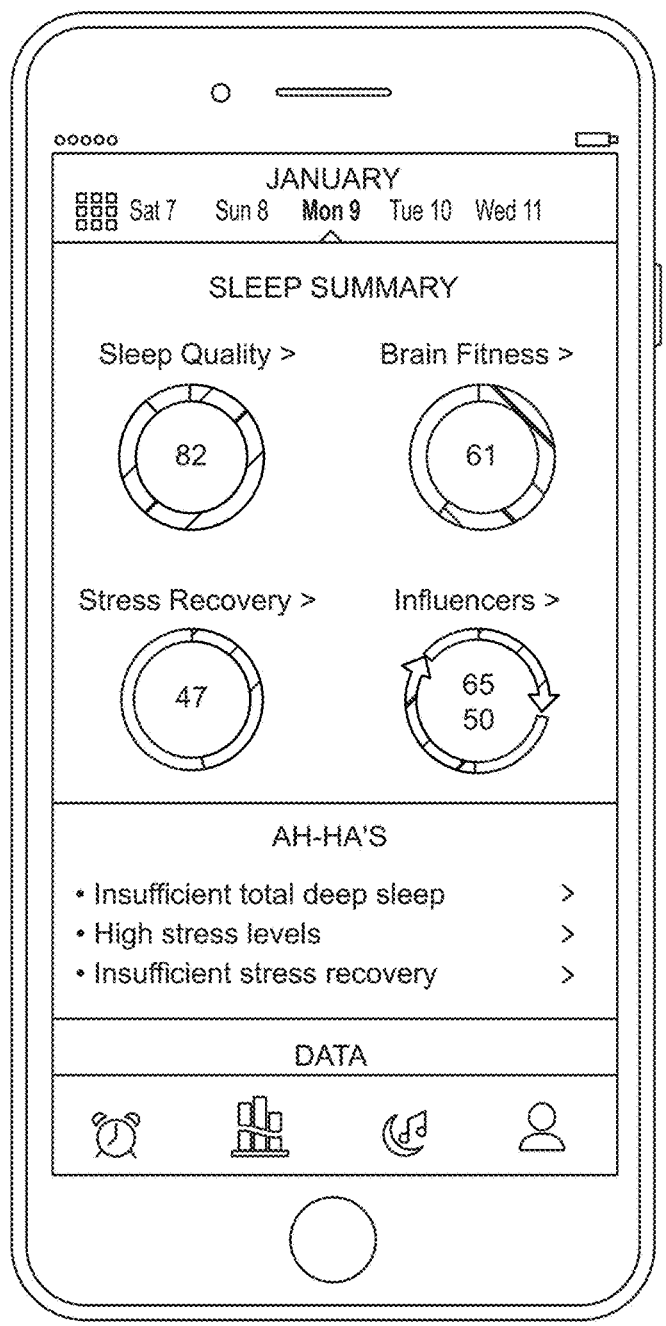
FIG. 11A illustrates a variation of a graphical user interface.

FIG. 11A illustrates that the data display device 20 can display a sleep summary graphical user interface (GUI) 11a having the illustrated display features.

Figure 11B:
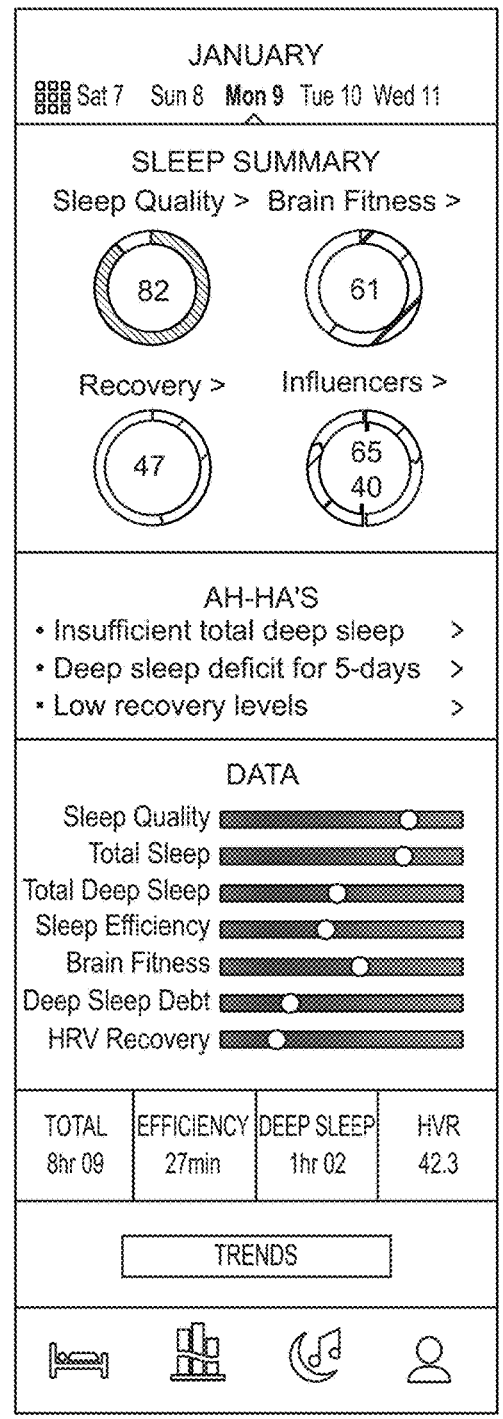
FIG. 11B illustrates a variation of a graphical user interface.

FIG. 11B illustrates that the data display device 20 can display a sleep summary GUI 11b having the illustrated display features.

FIGS. 11C and 11D illustrate that the data display device 20 can display a sleep quality GUI 11c and 11d having the illustrated display features.

FIG. 11E illustrates that the data display device 20 can display a brain fitness GUI 11e having the illustrated display features.

FIGS. 11F-11H illustrate that the data display device 20 can display a recovery/recharge GUI 11f, 11g, and 11h having the illustrated display features.

Figure 11I:
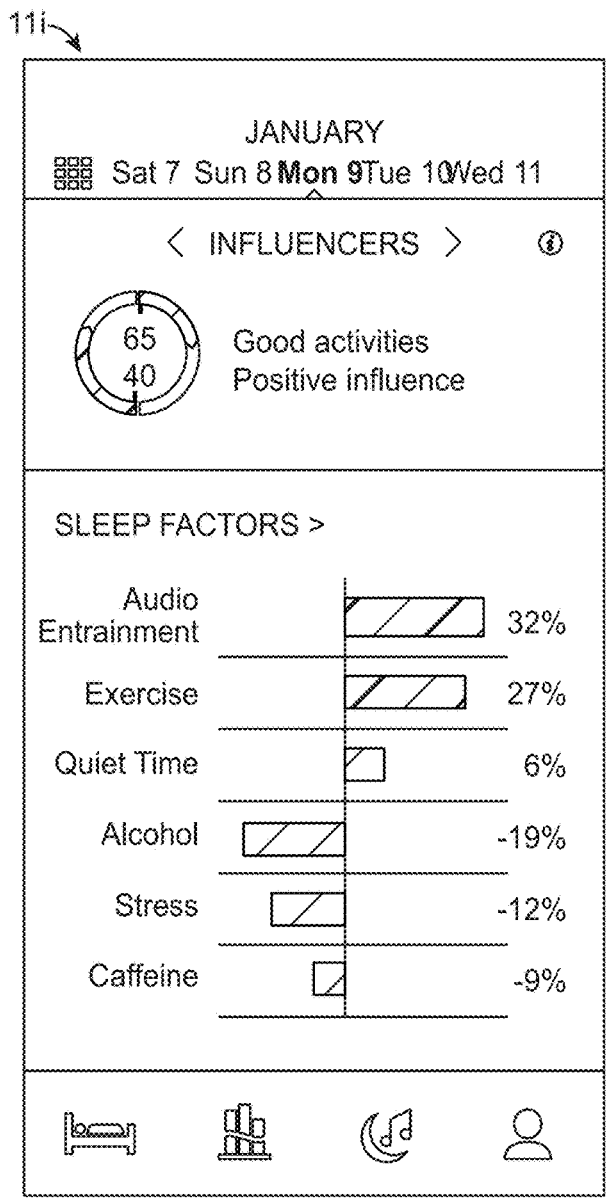
FIG. 11I illustrates a variation of a graphical user interface.
Figure 11J:
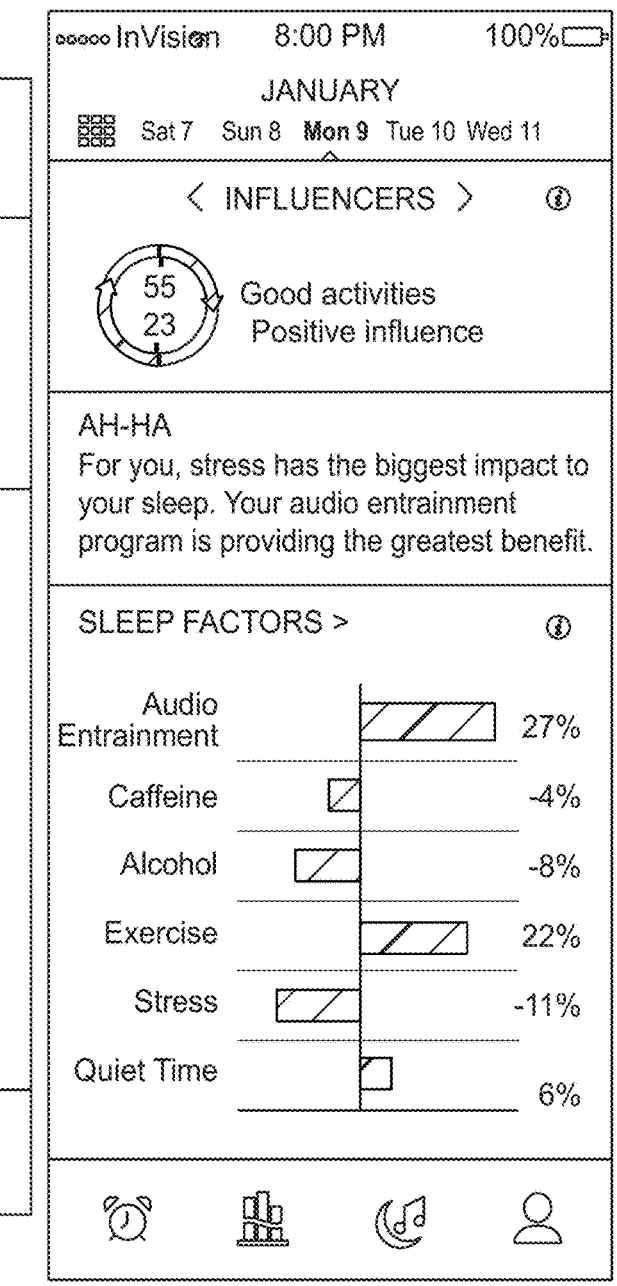
FIG. 11J illustrates a variation of a graphical user interface.

FIGS. 11I and 11J illustrate that the data display device 20 can display an influencers GUI 11i and 11j having the illustrated display features.

Derivation of Total Sleep Time Reference Curves

Total sleep time data can include research data, user data, or both. The total sleep time data can be separated into cohorts, for example, based on age, gender, ethnicity, health, fitness level, or any combination thereof. Total sleep time reference curves can be derived from total sleep time data. For example, cohort curves and/or non-cohort curves can be derived from total sleep time data.

Figure 12B:
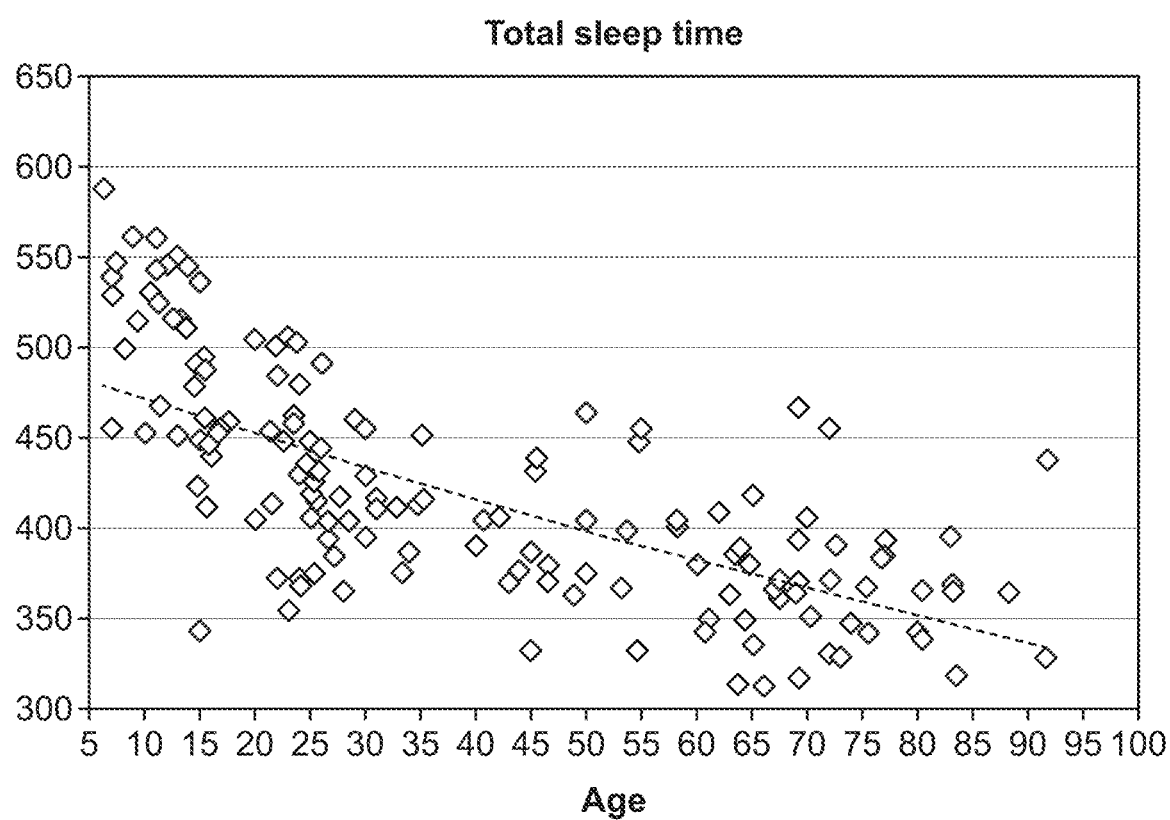

A method for determining total sleep time reference curves can include using data from published research. When determining age-based cohort curves for total sleep time, for example, such research can include Walter Moraes, Ronaldo Piovezan, Dalva Poyares, Lia Rita Bittencourt, Rogerio Santos-Silva, Sergio Tufik "Effects of aging on sleep structure throughout adulthood: a population based study". Sleep Medicine 15 (2014) 401-409; and Ohayon M M, Carskadon M A, Guilleminault C, Vitiello M V. "Meta-analysis of quantitative sleep parameters from childhood to old age in healthy individuals: developing normative sleep values across the human lifespan". *Sleep*. Nov. 1, 2004, which are each herein incorporated by reference in their entireties for all purposes. For example, FIG. 12A illustrates that data from Table 1 of the Moraes study can be used, and FIG. 12B illustrates that data from a figure of the Ohayon study can be used.

Figure 13B:
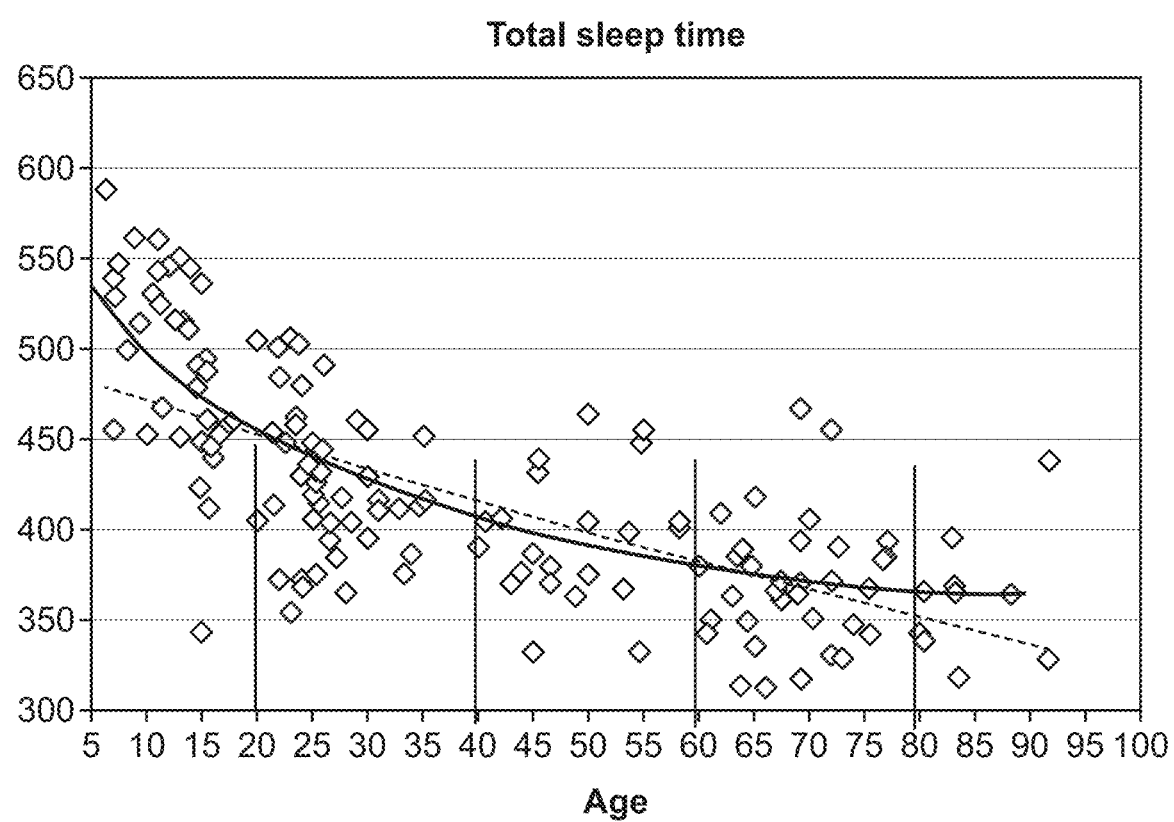

For any given data set (e.g., data sets having age cohorts), data of one or more cohort groupings (e.g., ages and/or age groups) can be used, for example, 1 to 10 or more groupings (e.g., three ages/age groups, four ages/age groups, five ages/age groups). For example, FIG. 13A illustrates that the data for age groups 20-24, 40-44, 60-64 and 75-80 can be selected from the Moraes study, and FIG. 13B illustrates that the data for ages 20, 40, 60 and 80 can be selected from the Ohayon study.

For any given data set (e.g., Moraes and Ohayon), one or multiple total sleep time statistics can be determined for each of the selected cohorts (e.g., ages/age groups) such as the average and standard deviation. For example, the average total sleep time for the selected cohorts (e.g., ages/age groups) can be determined, and from the calculated average, one or more standard deviations above and/or below the calculated average can be determined. For example, one, two, or three standard deviations above and/or below the average can be determined. The average and standard deviations can be plot points (also referred to as key points) to which a cohort curve can be fitted. A cohort curve can be generated using 1 to 7 or more plot points. The average can but need not be used as a plot point. A standard deviation can but need not be used as a plot point. When a cohort curve is generated, the plot points can include any combination of the average, one standard deviation above the average, two standard deviations above the average, three standard deviations above the average, one standard deviation below the average, two standard deviations below the average and three standard deviations below the average. For example, when a cohort curve is generated using 3 plot points, the 3 plot points can be the average, one standard deviation above the average and one standard deviation below the average. As another example, when a cohort curve is generated using 5 plot points, the 5 plot points can be the average, one standard deviation above the average, two standard deviations above the average, one standard deviation below the average and two standard deviations below the average. As yet another example, when a cohort curve is generated using 7 plot points, the 7 plot points can be the average, one standard deviation above the average, two standard deviations above the average, three standard deviations above the average, one standard deviation below the average, two standard deviations below the average and three standard deviations below the average.

Where multiple data sets are used (e.g., the Moraes and Ohayon data sets), the average total sleep time for the cohorts (e.g., ages/age groups) of each study can be determined, along with the standard deviations of the determined averages. A composite of the determined averages and standard deviations can then be used. The composite can include any combination of the determined plot points of each data set. For example, the composite can include an average of the determined plot points of each data set. The composite can include the plot points from each data set, an average of the corresponding plot points in each data set, or both. For example, the plot points of each data set can be plotted, an average of the like plot points in the data sets can be plotted, or both, where like plot points, using a two study example, can correspond to first study average-second study average and first study 1/2/3 standard deviation above/below-second study 1/2/3 standard deviation above/below, respectively. For example, the average and standard deviations for the 20-24 age group of the Moraes study and the average and standard deviations for the 20 year old age category of the Ohayon study can both be plotted, or the averages and corresponding standard deviations of both studies can be averaged and then plotted, or both. For example, the Moraes-average and the Ohayon average can be averaged, and each Moraes-standard deviation can be averaged with the corresponding Ohayon-standard deviation (e.g., the Moraes 1 above-Ohayon 1 above standard deviations can be averaged together, the Moraes 1 below-Ohayon 1 below standard deviations can be averaged together, the Moraes 2 above-Ohayon 2 above standard deviations can be averaged together, the Moraes 2 below-Ohayon 2 below standard deviations can be averaged together, the Moraes 3 above-Ohayon 3 above standard deviations can be averaged together, the Moraes 3 below-Ohayon 3 below standard deviations can be averaged together, or any combination thereof).

The determined averages and standard deviations can be assigned a total sleep time point value, where the total sleep time points can be on a total sleep time point scale having a minimum and maximum number of points, for example, a 0-100 point scale. The point scale can be linear or non-linear (e.g., logarithmic). A point value can be assigned to each average and standard deviation. For example, for a 100 point scale, the average for a given total sleep time cohort (e.g., age/age group) can be assigned 85 points, one standard deviation above the average can be assigned 95 points, two standard deviations above the average can be assigned 100 points, one standard deviation below the average can be assigned 70 points and two standard deviations below the average can be assigned 35 points. The maximum point value can be 100 points and the minimum point value can be 0 points. The points assigned to the total sleep time statistics can be the same or different from the points assigned to statistics of other sleep variables (e.g., total deep sleep, sleep efficiency, longest deep sleep duration, strength of deep sleep, recovery). The minimum y-intercept for the total sleep time can be zero, less than zero, or greater than zero for a total sleep time of 0 minutes.

The total sleep time averages and corresponding standard deviations for each cohort (e.g., age/age group)—also collectively referred to as data points—can be plotted, with each data point being plotted according to its age/age group (e.g., on the x-axis) and the point value assigned (e.g., on the y-axis). To determine the cohort curves (e.g., age-based cohort curves), a polynomial curve can be fitted to the plotted points. The plotted points can be composite points from multiple studies. Scores for in-between cohorts (e.g., ages/age groups) can be determined proportionately. For example, for age 25, which is one-fourth between ages 20 and 40, the resulting score can be one-fourth between the age 20 and 40 scores.

Figures 14C, 14D:
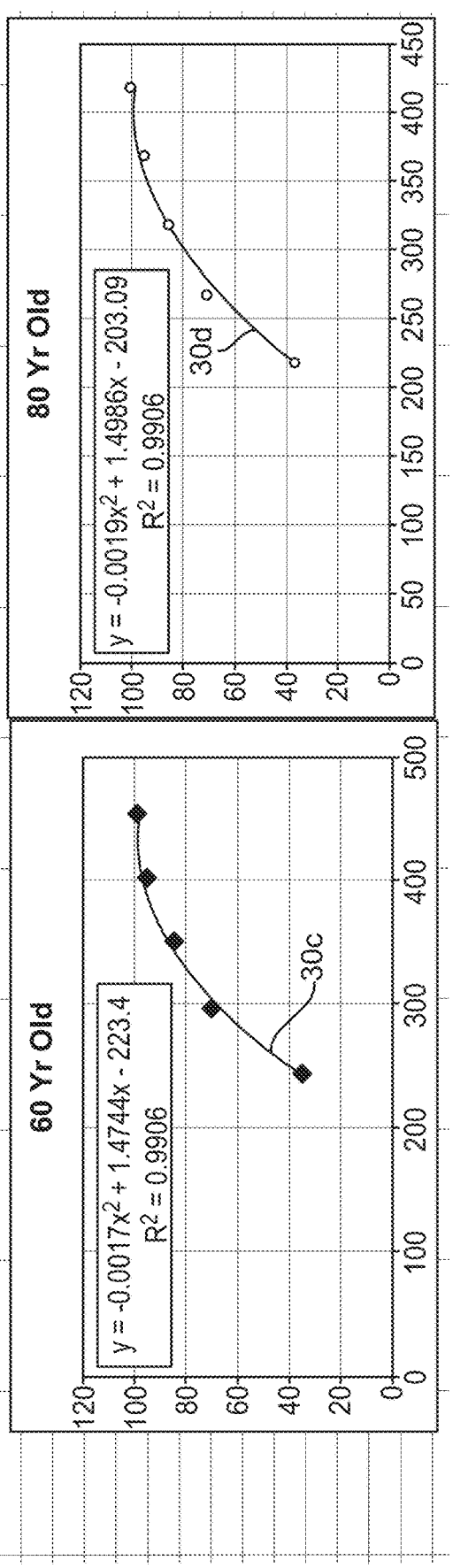

FIGS. 14A-14D illustrate how 5 key points can be determined for four different age groups: 20 year old (FIG. 14A), 40 year old (FIG. 14B), 60 year old (FIG. 14C) and 80 year old (FIG. 14D). The top halves of FIGS. 14A-14D illustrate tables for the statistics (e.g., averages and standard deviations) calculated from total sleep time data. For example, row 1 of the tables lists the average total sleep time for Moraes (20 yr: 376 minutes) and Ohayon (20 yr: 450 minutes), as well as a composite (e.g., average) of the two studies in the NG column (20 yr: (376+450)/2=413 minutes)). Row 2 lists the standard deviation of the average and row 3 lists the standard deviation percentage relative to the average (e.g., 20 yr Moraes: (75/376)×100=20%). The NG column lists the statistics derived from Moraes and Ohayon. For example, row 4 of the NG column relists the calculated total sleep time average (20 yr: 413 minutes) and rows 5-8 list the standard deviations shown, with the assigned total sleep time scores listed in the SCORES column. The statistics in rows 4-8 are an exemplary 5 key point set. Once the 5 key points are determined for an age group (e.g., the values shown in rows 4-8), the points can be plotted. A trend line can be determined which best fits the 5 points (e.g., see the bottom halves of FIGS. 14A-14D), where the trend line can be a polynomial or non-polynomial trend line. The five key points calculated in the top halves of FIGS. 14A-14D are denoted as the five plotted points along each of the best fit curves in the bottom halves of FIGS. 14A-14D. The trend line can be plotted and smoothed. These generated trend lines can be the derived total sleep time cohort curves. For example, FIGS. 14A-14D illustrate polynomial age-cohort curves 30a, 30b, 30c and 30d for ages 20, 40, 60 and 80, respectively. The polynomial equation for the 20 yr old curve 30a can be $y=-0.0012x^2+1.2298x-218.87$ with $R^2=0.9906$. The polynomial equation for the 40 yr old curve 30b can be $y=-0.0018x^2+1.5929x-263.13$ with $R^2=0.9906$. The polynomial equation for the 60 yr old curve 30c can be $y=-0.0017x^2+1.4744x-223.4$ with $R^2=0.9906$. The polynomial equation for the 80 yr old curve 30d can be $y=-0.0019x^2+1.4986x-203.09$ with $R^2=0.9906$. The curves 30a, 30b, 30c and 30d can alternatively be the age-cohort curves 40a, 40b, 40c and 40d for which the trend lines are non-polynomial curves.

Figures 15A, 15B:
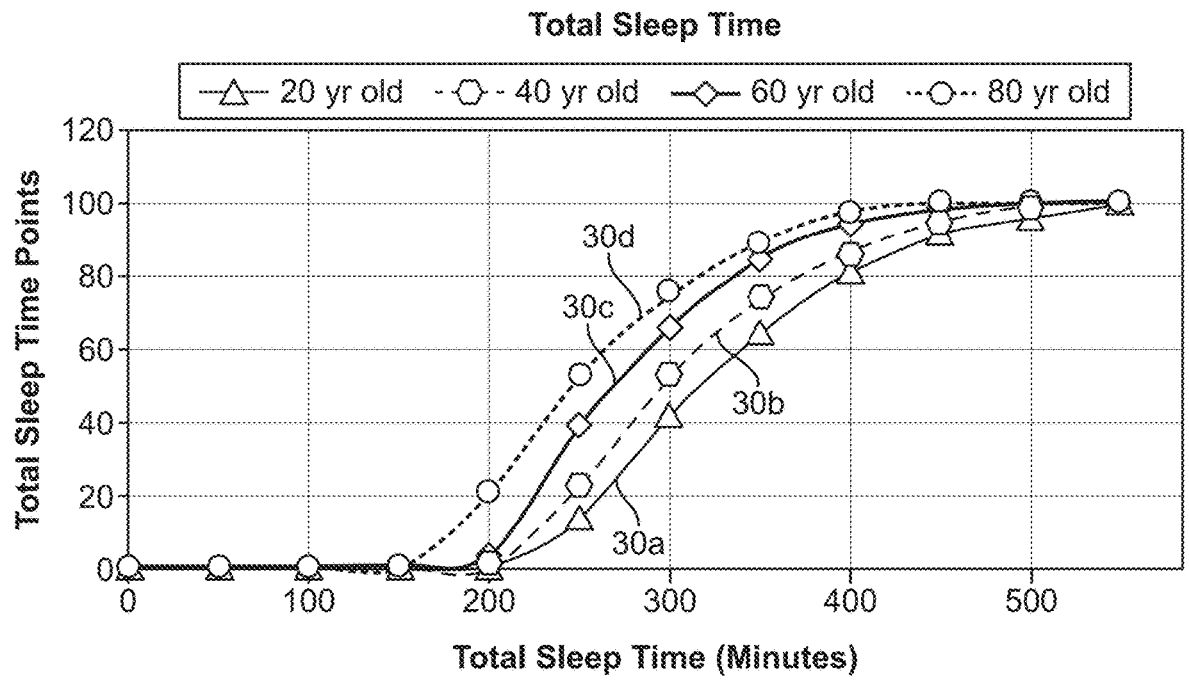
FIG. 15A illustrates a variation of total sleep time cohort curves derived from the method illustrated in FIGS. 14A-14D.
FIG. 15B illustrates a variation of a table of exemplary total sleep time scores using the cohort curves of FIG. 15A.

FIG. 15A illustrates curves 30a-30d plotted together and smoothed. For example, upon reaching max/min scores of 100/0, it can be assumed the curves will remain at 100/0 points for scores. This can correspond to the flat regions of the generated curves. However, scores outside 3 standard deviations are considered extreme and the user can get a corresponding notifying alert. The alert can include a request to the user that they recalibrate the device, can include an alert related the user's well-being, or both.

In this way, total sleep time points by age can be determined, for example, by reference to the total sleep time reference curves. For example, FIG. 15B illustrates a variation of a table of exemplary total sleep time scores using the cohort curves 30a-30d of FIG. 15A. The table of FIG. 15B is also referred to as a total sleep time scoring table.

Derivation of Total Deep Sleep Reference Curves

Total deep sleep data (also referred to as deep sleep duration data) can include research data, user data, or both. The total deep sleep data can be separated into cohorts, for example, based on age, gender, ethnicity, health, fitness level, or any combination thereof. Total deep sleep reference curves can be derived from total deep sleep data. For example, cohort curves and/or non-cohort curves can be derived from total deep sleep data.

Figure 16:
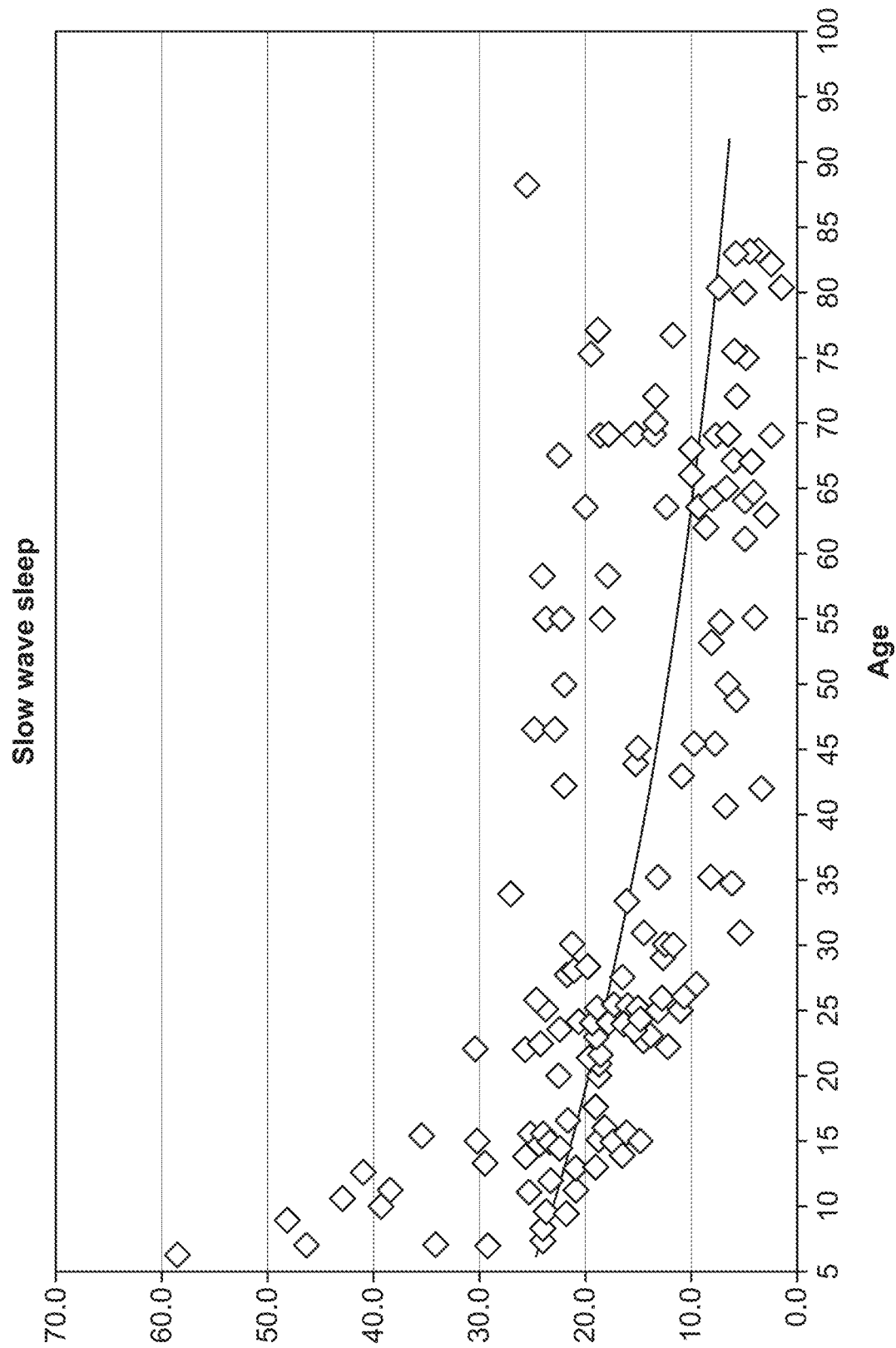
FIG. 16 illustrates a variation of exemplary research data.

A method for determining total deep sleep reference curves can include using data from published research. When determining age-based cohort curves for total deep sleep, for example, such research can include the Moraes and Ohayon studies incorporated above. For example, FIG. 12A illustrates that data from Table 1 of the Moraes study can be used, and FIG. 16 illustrates that data from a figure of the Ohayon study can be used.

Figure 17B:
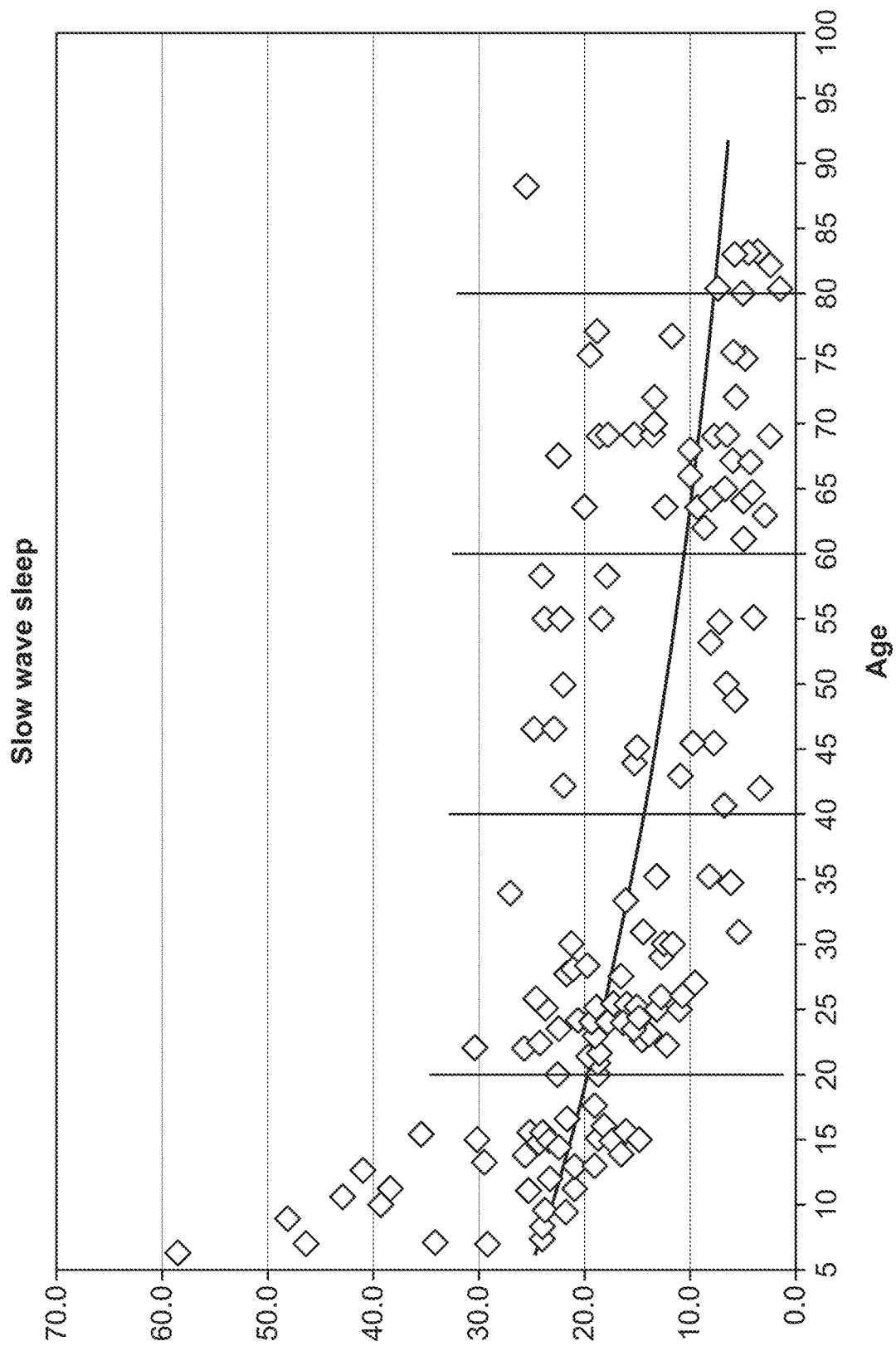

For any given data set (e.g., data sets having age cohorts), data of one or more cohort groupings (e.g., ages and/or age groups) can be used, for example, 1 to 10 or more groupings (e.g., three ages/age groups, four ages/age groups, five ages/age groups). For example, FIG. 17A illustrates that the data for age groups 20-24, 40-44, 60-64 and 75-80 can be selected from the Moraes study, and FIG. 17B illustrates that the data for ages 20, 40, 60 and 80 can be selected from the Ohayon study.

For any given data set (e.g., Moraes and Ohayon), one or multiple total deep sleep statistics can be determined for each of the selected cohorts (e.g., ages/age groups) such as the average and standard deviation. From the calculated average, one or more standard deviations above and/or below the calculated average can be determined as described above with reference to deriving the total sleep time cohort curves.

Where multiple data sets are used (e.g., the Moraes and Ohayon data sets), the average total deep sleep for the cohorts (e.g., ages/age groups) of each study can be determined, along with the standard deviations of the determined averages. A composite of the determined averages and standard deviations can then be used or derived as described above with reference to deriving the total sleep time cohort curves.

The determined averages and standard deviations can be assigned a total deep sleep point value, where the total deep sleep points can be on a total deep sleep point scale having a minimum and maximum number of points, for example, a 0-100 point scale. The point scale can be linear or non-linear (e.g., logarithmic). A point value can be assigned to each average and standard deviation. The points assigned to the total deep sleep statistics can be the same or different from the points assigned to statistics of other sleep variables (e.g., total sleep time, sleep efficiency, longest deep sleep duration, strength of deep sleep, recovery). The total deep sleep assigned points can be modified from the total sleep time assigned points when, for example, the distribution band for total deep sleep duration is tighter than the total sleep time distribution band. For example, for a 100 point scale, the average for a given total deep sleep cohort (e.g., age/age group) can be assigned 85 points, one standard deviation above the average can be assigned 95 points, two standard deviations above the average can be assigned 100 points, one standard deviation below the average can be assigned 50 points and two standard deviations below the average can be assigned 15 points. The maximum point value can be 100 points and the minimum point value can be 0 points. The minimum y-intercept for the total deep sleep can be zero, less than zero, or greater than zero for a total deep sleep of 0 minutes.

The total deep sleep averages and corresponding standard deviations for each cohort (e.g., age/age group)—also collectively referred to as data points—can be plotted and a curve can be fitted to the plotted points as described above with reference to deriving the total sleep time reference curves.

Figures 18A, 18B:
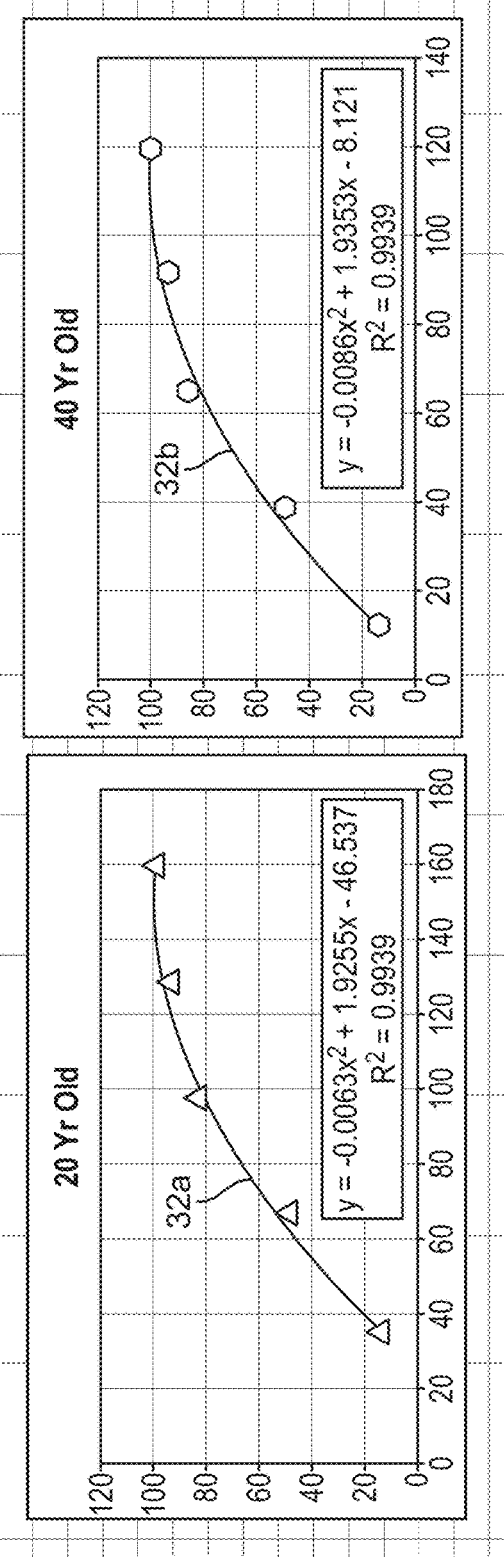
FIGS. 18A-18D illustrate a variation of a method for deriving total deep sleep cohort curves.
Figures 18C, 18D:
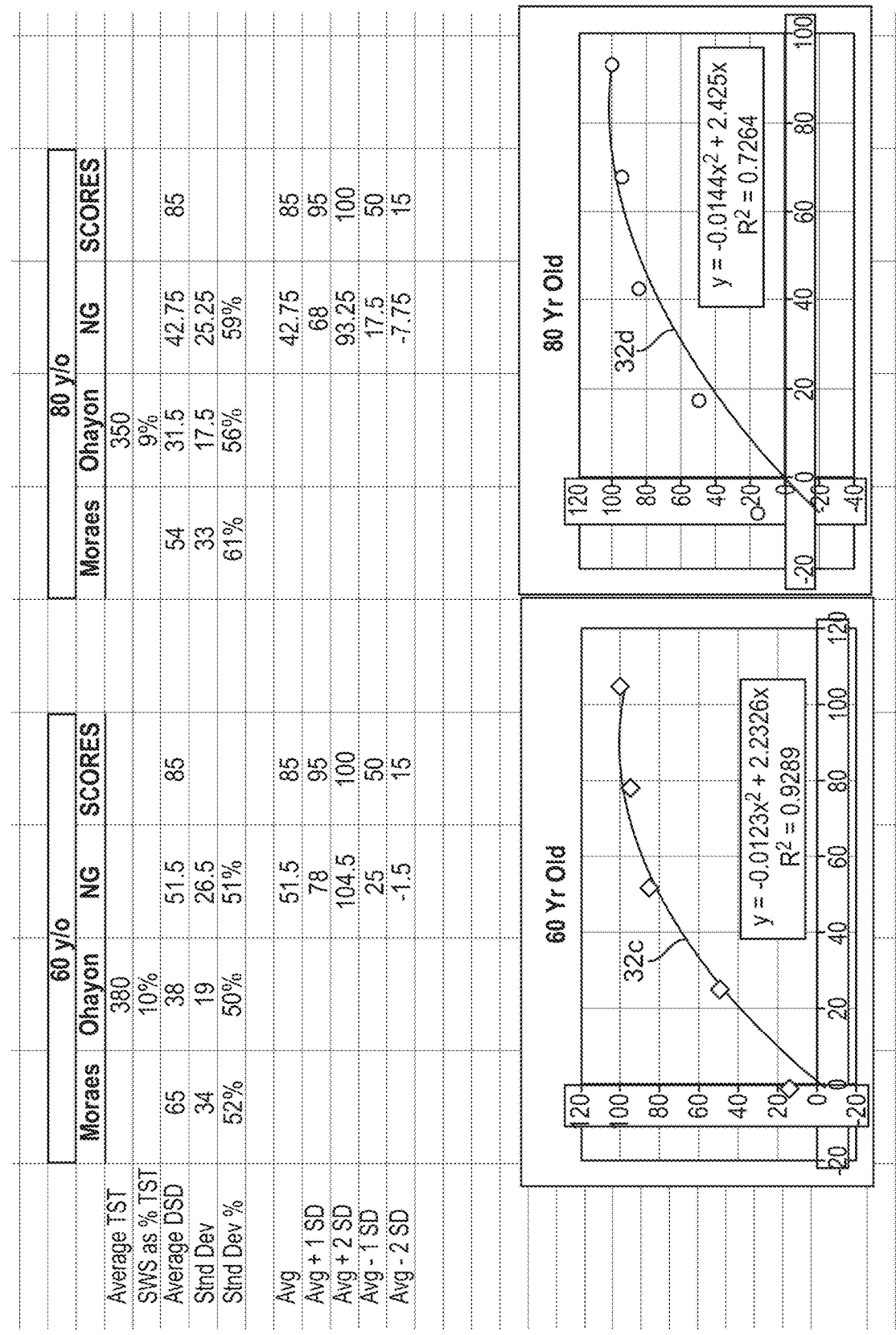

FIGS. 18A-18D illustrate how 5 key points can be determined for four different age groups: 20 year old (FIG. 18A), 40 year old (FIG. 18B), 60 year old (FIG. 18C) and 80 year old (FIG. 18D). The top halves of FIGS. 18A-18D illustrate tables for the statistics (e.g., averages and standard deviations) calculated from total deep sleep data. For example, for the values shown in the tables, row 1 lists the average total sleep time (TST), row 2 lists slow wave sleep (SWS) as a percentage of TST, row 3 lists the average deep sleep duration (DSD), row 4 lists the standard deviation of the average DSD and row 5 lists the standard deviation percentage relative to the average DSD (e.g., 20 yr Moraes: $(26/87) \times 100 = 30\%$). The NG column lists the statistics derived from Moraes and Ohayon. For example, row 3 lists the average DSD for Moraes (20 yr: 87 minutes) and Ohayon (20 yr: 108 minutes), as well as a composite (e.g., average) of the two studies in the NG column (20 yr: $(87+108)/2=97.5$ minutes)). Row 6 of the NG column relists the calculated DSD average (20 yr: 97.5 minutes) and rows 6-10 list the standard deviations shown, with the assigned deep sleep duration scores listed in the SCORES column. The statistics in rows 6-10 are an exemplary 5 key point set. Once the 5 key points are determined for an age group (e.g., the values shown in rows 6-10), the points can be plotted. A trend line can be determined which best fits the 5 points (e.g., see the bottom halves of FIGS. 18A-18D), where the trend line can be a polynomial or non-polynomial trend line. The five key points calculated in the top halves of FIGS. 18A-18D are denoted as the five plotted points along each of the best fit curves in the bottom halves of FIGS. 18A-18D. The trend line can be plotted and smoothed. These generated trend lines can be the derived total deep sleep cohort curves. For example, FIGS. 18A-18D illustrate polynomial age-cohort curves 32a, 32b, 32c and 32d for ages 20, 40, 60 and 80, respectively. The polynomial equation for the 20 yr old curve 32a can be $y=-0.0063x^2+1.9255x-46.537$ with $R^2=0.9939$. The polynomial equation for the 40 yr old curve 32b can be $y=-0.0086x^2+1.9353x-8.121$ with $R^2=0.9939$. The polynomial equation for the 60 yr old curve 32c can be $y=-0.0123x^2+2.2326x$ with $R^2=0.9289$. The polynomial equation for the 80 yr old curve 32d can be $y=-0.0144x^2+2.425x$ with $R^2=0.7264$. The curves 32a, 32b, 32c and 32d can alternatively be the age-cohort curves 42a, 42b, 42c and 42d for which the trend lines are non-polynomial curves.

Figures 19A, 19B:
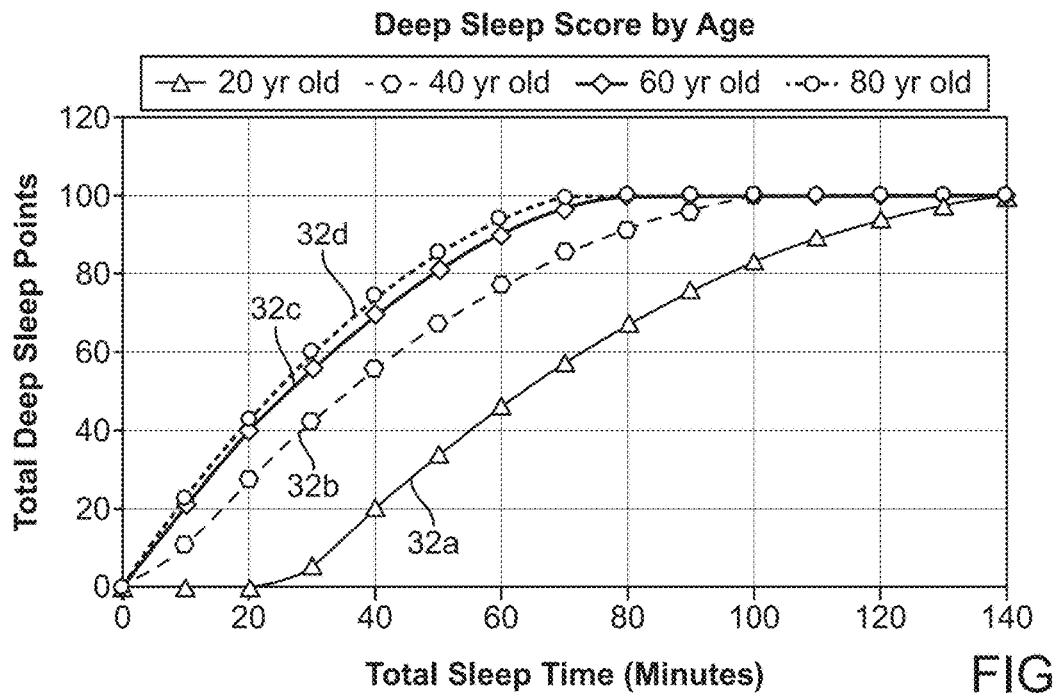
FIG. 19A illustrates a variation of total deep sleep cohort curves derived from the method illustrated in FIGS. 18A-18D.
FIG. 19B illustrates a variation of a table of exemplary total deep sleep scores using the cohort curves of FIG. 19A.

FIG. 19A illustrates curves 32a-32d plotted together and smoothed. For example, upon reaching max/min scores of 100/0, it can be assumed the curves will remain at 100/0 points for scores. This can correspond to the flat regions of the generated curves. However, scores outside 3 standard deviations are considered extreme and the user can get a corresponding notifying alert. The alert can include a request to the user that they recalibrate the device, can include an alert related the user's well-being, or both.

In this way, total deep sleep points by age can be determined, for example, by reference to the total deep sleep reference curves. For example, FIG. 19B illustrates a variation of a table of exemplary total deep sleep scores using the cohort curves 32a-32d of FIG. 19A. The table of FIG. 19B is also referred to as a total deep sleep scoring table.

Derivation of Sleep Efficiency Reference Curves

Sleep efficiency data can include research data, user data, or both. Sleep efficiency data can be separated into cohorts, for example, based on age, gender, ethnicity, health, fitness level, or any combination thereof. Sleep efficiency reference curves can be derived from total sleep time data and/or from sleep efficiency data. For example, cohort curves and/or non-cohort curves can be derived from total sleep time data and/or sleep efficiency data.

Figure 20:
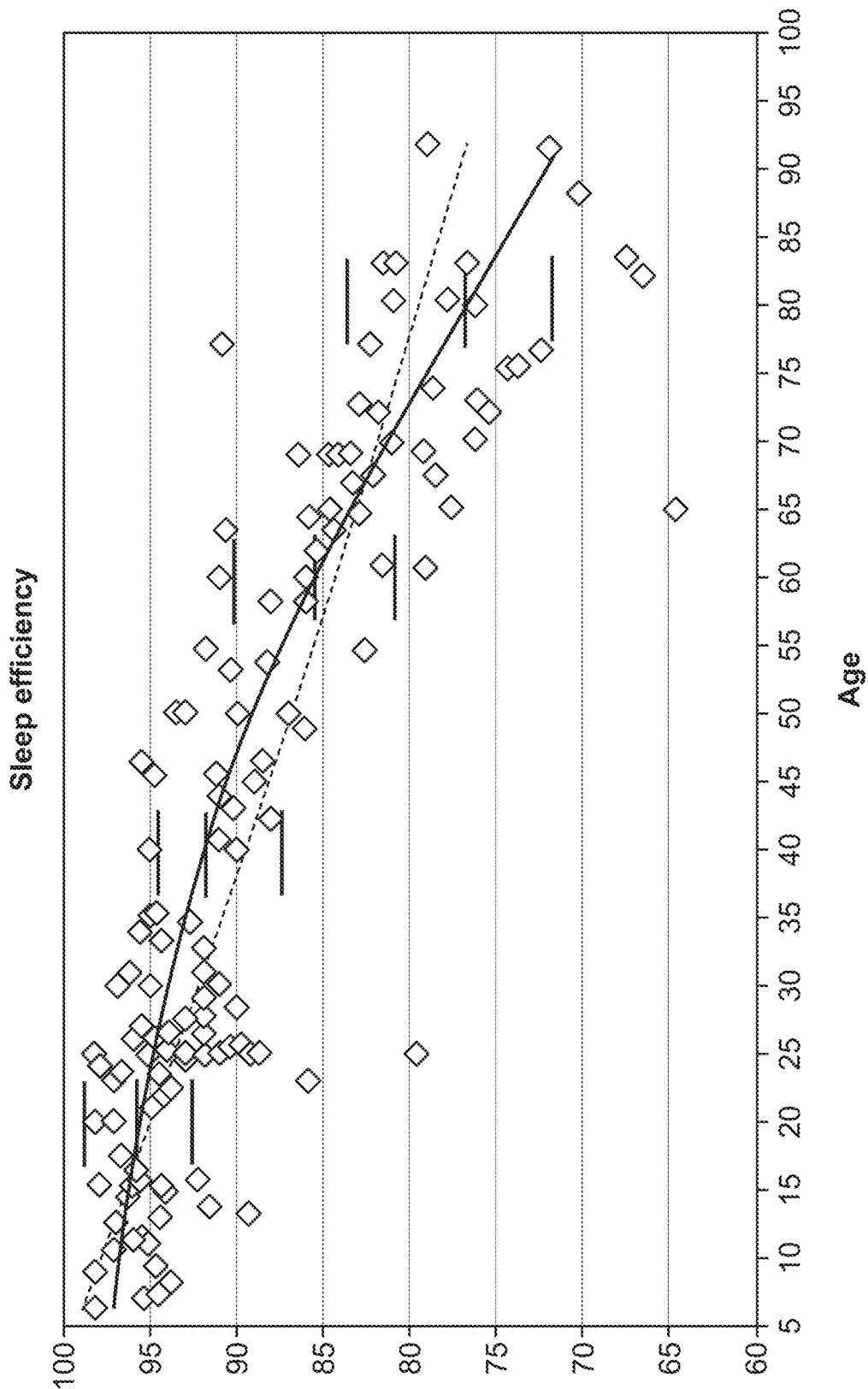
FIG. 20 illustrates a variation of exemplary research data and a variation of exemplary cohorts selected from the illustrated research data.

A method for determining sleep efficiency reference curves can include using data from published research. When determining age-based cohort curves for sleep efficiency, for example, such research can include the Moraes and Ohayon studies incorporated above. For example, FIG. 12A illustrates that data from Table 1 of the Moraes study can be used, and FIG. 20 illustrates that data from a figure of the Ohayon study can be used.

For any given data set (e.g., data sets having age cohorts), data of one or more cohort groupings (e.g., ages and/or age groups) can be used, for example, 1 to 10 or more groupings (e.g., three ages/age groups, four ages/age groups, five ages/age groups). For example, FIG. 21 illustrates that the data for age groups 20-24, 40-44, 60-64 and 75-80 can be selected from the Moraes study, and FIG. 20 further illustrates that the data for ages 20, 40, 60 and 80 can be selected from the Ohayon study.

For any given data set (e.g., Moraes and Ohayon), one or multiple sleep efficiency statistics can be determined for each of the selected cohorts (e.g., ages/age groups) such as the average and standard deviation. From the calculated average, one or more standard deviations above and/or below the calculated average can be determined as described above with reference to deriving the total sleep time and total deep sleep cohort curves.

Where multiple data sets are used (e.g., the Moraes and Ohayon data sets), the average sleep efficiency for the cohorts (e.g., ages/age groups) of each study can be determined, along with the standard deviations of the determined averages. A composite of the determined averages and standard deviations can then be used or derived as described above with reference to deriving the total sleep time and total deep sleep cohort curves.

The determined averages and standard deviations can be assigned a sleep efficiency point value, where the sleep efficiency points can be on a sleep efficiency point scale having a minimum and maximum number of points, for example, a 0-100 point scale. The point scale can be linear or non-linear (e.g., logarithmic). A point value can be assigned to each average and standard deviation. The points assigned to the sleep efficiency statistics can be the same or different from the points assigned to statistics of other sleep variables (e.g., total sleep time, total deep sleep, longest deep sleep duration, strength of deep sleep, recovery). For example, for a 100 point scale, the average for a given sleep efficiency cohort (e.g., age/age group) can be assigned 85 points, one standard deviation above the average can be assigned 95 points, two standard deviations above the average can be assigned 100 points, one standard deviation below the average can be assigned 70 points and two standard deviations below the average can be assigned 35 points. The maximum point value can be 100 points and the minimum point value can be 0 points. The minimum y-intercept for the sleep efficiency can be zero, less than zero, or greater than zero for a sleep efficiency of zero.

The sleep efficiency averages and corresponding standard deviations for each cohort (e.g., age/age group)—also collectively referred to as data points—can be plotted and a curve can be fitted to the plotted points as described above with reference to deriving the total sleep time reference curves.

Figures 22C, 22D:
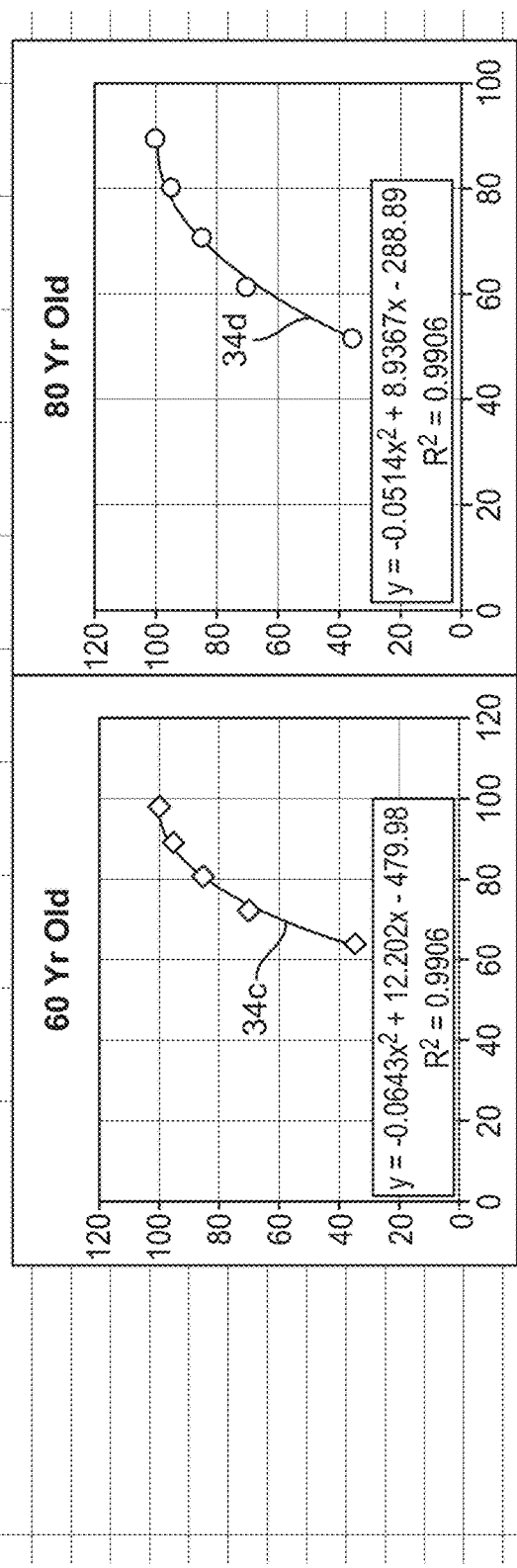

FIGS. 22A-22D illustrate how 5 key points can be determined for four different age groups: 20 year old (FIG. 22A), 40 year old (FIG. 22B), 60 year old (FIG. 22C) and 80 year old (FIG. 22D). The top halves of FIGS. 22A-22D illustrate tables for the statistics (e.g., averages and standard deviations) calculated from sleep efficiency data. For example, row 1 of the tables lists the average sleep efficiency for Moraes (20 yr: 88) and Ohayon (20 yr: 96), as well as a composite (e.g., average) of the two studies in the NG column (20 yr: (88+96)/2=92)). Row 2 lists the standard deviation of the average and row 3 lists the standard deviation percentage relative to the average (e.g., 20 yr Moraes: (9.5/88)×100=11%). The NG column lists the statistics derived from Moraes and Ohayon. For example, row 4 of the NG column relists the calculated sleep efficiency average (20 yr: 92) and rows 5-8 list the standard deviations shown, with the assigned sleep efficiency scores listed in the SCORES column. The statistics in rows 4-8 are an exemplary 5 key point set. Once the 5 key points are determined for an age group (e.g., the values shown in rows 4-8), the points can be plotted. A trend line can be determined which best fits the 5 points (e.g., see the bottom halves of FIGS. 22A-22D), where the trend line can be a polynomial or non-polynomial trend line. The five key points calculated in the top halves of FIGS. 22A-22D are denoted as the five plotted points along each of the best fit curves in the bottom halves of FIGS. 22A-22D. The trend line can be plotted and smoothed. These generated trend lines can be the derived sleep efficiency cohort curves. For example, FIGS. 22A-22D illustrate polynomial age-cohort curves 34a, 34b, 34c and 34d for ages 20, 40, 60 and 80, respectively. The polynomial equation for the 20 yr old curve 34a can be $y=-0.1019x^2+21.046x-987.46$. The polynomial equation for the 40 yr old curve 34b can be $y=-0.0725x^2+14.575x-632.82$. The polynomial equation for the 60 yr old curve 34c can be $y=-0.0643x^2+12.202x-479.98$. The polynomial equation for the 80 yr old curve 34d can be $y=-0.0514x^2+8.9367x-288.89$. The curves 34a, 34b, 34c and 34d can alternatively be the age-cohort curves 44a, 44b, 44c and 44d for which the trend lines are non-polynomial curves.

Figures 23A, 23B:
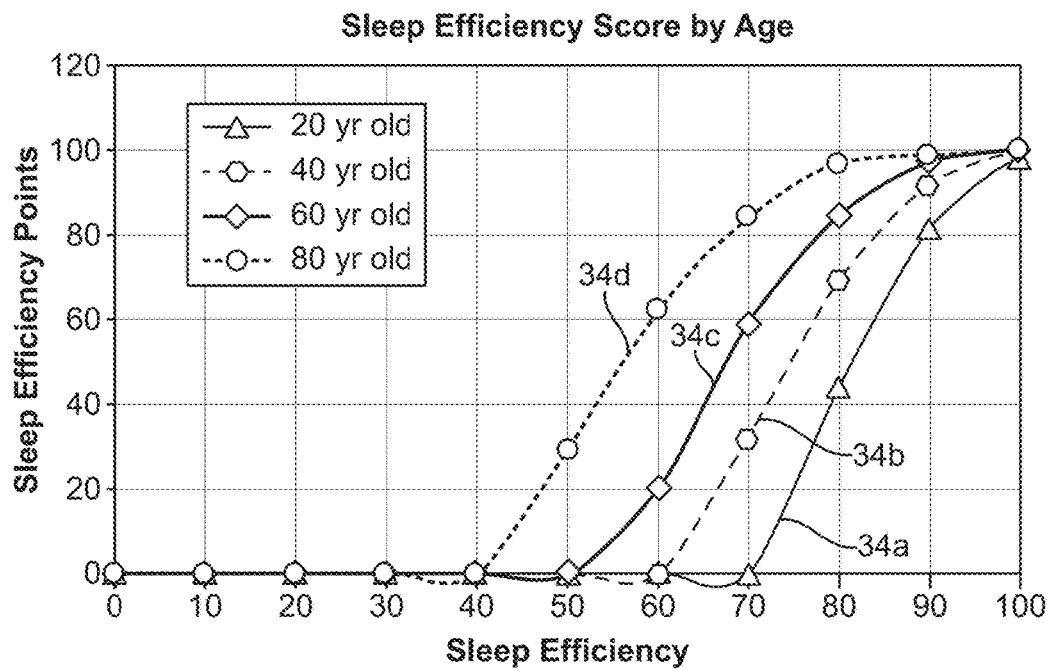
FIG. 23A illustrates a variation of sleep efficiency cohort curves derived from the method illustrated in FIGS. 22A-22D.
FIG. 23B illustrates a variation of a table of exemplary sleep efficiency scores using the cohort curves of FIG. 23A.

FIG. 23A illustrates curves 34a-34d plotted together and smoothed. For example, upon reaching max/min scores of 100/0, it can be assumed the curves will remain at 100/0 points for scores. This can correspond to the flat regions of the generated curves. However, scores outside 3 standard deviations are considered extreme and the user can get a corresponding notifying alert. The alert can include a request to the user that they recalibrate the device, can include an alert related the user's well-being, or both.

In this way, sleep efficiency points by age can be determined, for example, by reference to the sleep efficiency reference curves. For example, FIG. 23B illustrates a variation of a table of exemplary sleep efficiency scores using the cohort curves 34a-34d of FIG. 23A. The table of FIG. 23B is also referred to as a sleep efficiency scoring table.

Derivation of Longest Deep Sleep Strength Reference Curves

Longest deep sleep (also referred to as longest duration of deep sleep) can include research data, user data, or both. The longest deep sleep data can be separated into cohorts, for example, based on age, gender, ethnicity, health, fitness level, or any combination thereof. Longest deep sleep reference curves can be derived from longest deep sleep data. For example, cohort curves and/or non-cohort curves can be derived from longest deep sleep data.

A method for determining longest deep sleep reference curves can include using data from research or acquired from users during use (e.g., user data). When determining reference curves for longest deep sleep, such data can include user data (e.g., acquired via device 12) and an analysis of a polysomnogram dataset (e.g., from The Montreal Archive of Sleep Studies (MASS)) to profile overall averages and standard deviations for longest deep sleep. The averages and standard deviations can be separated in cohorts, for example, by age, gender, ethnicity, health, fitness level, or any combination thereof. The user data can be used to derive the averages and standard deviations based on age/age group and other defined cohorts for longest deep sleep. The weighting of the longest deep sleep variable can be increased to more than 10%, for example, a percentage of 11% to 80% or more, as more user data is collected.

The longest deep sleep cohort curves can be derived as described above with reference to deriving the total sleep time cohort curves, the total deep sleep cohort curves, the sleep efficiency cohort curves, or any combination thereof.

For example, for a 100 point scale, the average for a given longest deep sleep data set (e.g., cohort) can be assigned 85 points, one standard deviation above the average can be assigned 95 points, two standard deviations above the average can be assigned 100 points, one standard deviation below the average can be assigned 70 points and two standard deviations below the average can be assigned 35 points. The maximum point value can be 100 points and the minimum point value can be 0 points. The minimum y-intercept for the longest deep sleep can be zero, less than zero or greater than zero for a total deep sleep time of 0 minutes.

The longest deep sleep averages and corresponding standard deviations for the longest deep sleep data set—also collectively referred to as data points—can be plotted and a curve can be fitted to the plotted points as described above with reference to deriving any of the other reference curves.

For example, FIG. 24A illustrates how 5 key points can be determined for the longest deep sleep variable. Row 1 of the table lists the average longest deep sleep (e.g., acquired from one or multiple users using the device 12 or other sleep monitoring device), row 2 lists the standard deviation of the average and row 3 lists the standard deviation percentage relative to the average (e.g., 32/40)×100=80%). The NG column lists the statistics derived from the analyzed data. For example, row 4 of the NG column relists the calculated longest deep sleep average (40 minutes) and rows 5-8 list the standard deviations shown, with the assigned longest deep sleep scores listed in the SCORES column. The statistics in rows 4-8 are an exemplary 5 key point set. Once the 5 key points are determined (e.g., the values shown in rows 4-8), the points can be plotted. A trend line can be determined which best fits the 5 points (e.g., see FIG. 24B), where the trend line can be a polynomial or non-polynomial trend line. The five key points calculated in FIG. 24A are denoted as the five plotted points along the best fit curve in FIG. 24B. The trend line can be plotted and smoothed. These generated trend line(s) can be the longest deep sleep reference curve(s).

For any of the sleep variables, the data can be used to derive cohort curves, non-cohort curves, or both. For example, FIG. 24B illustrates that the longest deep sleep data can be used to generate a polynomial non-cohort longest deep sleep reference curve 36a. The curve 36a in FIG. 24 can have the illustrated equation: $y=-0.017x^2+2.7673x-7.3885$, where $R^2=0.9651$. The curve 36a can alternatively be curve 46a for which the trend line is a non-polynomial curve. The curve 36a can alternatively be a non-polynomial curve, or both polynomial and non-polynomial curves can be fitted to the data.

In this way, longest deep sleep points can be determined, for example, by reference to the longest deep sleep reference curve(s). For example, FIG. 24C illustrates a variation of a table of exemplary longest deep sleep scores using the curve 36a of FIG. 24B. The left column is the longest deep sleep in minutes and the right column is the corresponding longest deep sleep score for each of the longest deep sleep values listed. The table of FIG. 24B is also referred to as a longest deep sleep scoring table.

FIG. 24D illustrates another example of a longest deep sleep curve 36a defined by the illustrated polynomial equation: $y=-0.0156x^2+2.5625x-2.4287$, where $R^2=0.9968$.

Derivation of Deep Sleep Strength Reference Curves

Strength of deep sleep (also referred to as deep sleep strength) can include research data, user data, or both. The deep sleep strength data can be separated into cohorts, for example, based on age, gender, ethnicity, health, fitness level, or any combination thereof. Deep sleep strength reference curves can be derived from deep sleep strength data. For example, cohort curves and/or non-cohort curves can be derived from deep sleep strength data.

A method for determining deep sleep strength reference curves can include using data from research or acquired from users during use (e.g., user data). When determining reference curves for deep sleep strength, such data can include user data (e.g., acquired via device 12) and an analysis of a polysomnogram dataset. The user data can be used to derive the averages and standard deviations based on age/age group and other defined cohorts for deep sleep strength. The weighting of the deep sleep strength variable can be increased to more than 10%, for example, a percentage of 11% to 80% or more, as more user data is collected.

The deep sleep strength curves can be derived as described above with reference to deriving the total sleep time cohort curves, the total deep sleep cohort curves, the sleep efficiency cohort curves, the longest deep sleep reference curves, or any combination thereof.

For example, for a 100 point scale, the average for a given deep sleep strength data set (e.g., cohort) can be assigned 85 points, one standard deviation above the average can be assigned 95 points, two standard deviations above the average can be assigned 100 points, one standard deviation below the average can be assigned 70 points and two standard deviations below the average can be assigned 35 points. The maximum point value can be 100 points and the minimum point value can be 0 points. The minimum y-intercept for the longest deep sleep can be zero, less than zero or greater than zero for a total deep sleep time of 0 minutes.

The deep sleep strength averages and corresponding standard deviations for the deep sleep strength data set—also collectively referred to as data points—can be plotted and a curve can be fitted to the plotted points as described above with reference to deriving any of the other reference curves.

For example, FIG. 25A illustrates how 5 key points can be determined for the deep sleep strength variable. Row 1 of the table lists the average deep sleep strength (e.g., acquired from one or multiple users using the device 12 or other sleep monitoring device), row 2 lists the standard deviation of the average and row 3 lists the standard deviation percentage relative to the average (e.g., 0.32/1.23)×100=26%). The NG column lists the statistics derived from the analyzed data. For example, row 4 of the NG column relists the calculated deep sleep strength (1.23)—also referred to as the average power spectral density (PSD)—and rows 5-8 list the standard deviations shown, with the assigned PSD scores listed in the SCORES column. The statistics in rows 4-8 are an exemplary 5 key point set. Once the 5 key points are determined (e.g., the values shown in rows 4-8), the points can be plotted. A trend line can be determined which best fits the 5 points (e.g., see FIG. 25B), where the trend line can be a polynomial or non-polynomial trend line. The five key points calculated in FIG. 25A are denoted as the five plotted points along the best fit curve in FIG. 25B. The trend line can be plotted (e.g., see FIG. 25B) and smoothed (e.g., see FIG. 25C). These generated trend line(s) can be the derived deep sleep curve(s).

For any of the sleep variables, the data can be used to derive cohort curves, non-cohort curves, or both. For example, FIGS. 24B and 25C illustrate that the deep sleep strength data can be used to generate a polynomial non-cohort deep sleep strength reference curve 49a. The curve 49a in FIG. 24 can have the illustrated equation: $y=-113.59x^2+376.02x-208.39$, where $R^2=0.9576$. The curve 49a can alternatively be a non-polynomial curve, or both polynomial and non-polynomial curves can be fitted to the data.

In this way, deep sleep strength points can be determined, for example, by reference to the deep sleep strength reference curve(s). For example, FIG. 25D illustrates a variation of a table of exemplary PSD scores using the curve 49a of FIGS. 25B and 25C. The left column is the deep sleep strength and the right column is the PSD score associated with each of the PSD values listed in the left column. The table of FIG. 25D is also referred to as a deep sleep strength (or PSD) scoring table.

Calculating HRV Reference Curves

The recovery score can be derived from heart rate variability (HRV) data. The HRV data can include research data, user data, or both. The HRV data can be separated into cohorts, for example, based on age, gender, ethnicity, health, fitness level, or any combination thereof. Recovery score reference curves can be derived from HRV data. For example, cohort curves and/or non-cohort curves can be derived from HRV data.

The recovery score can be calculated, for example, using a two-step process: (1) determine the heart rate variability (HRV) during the last 5 minutes of light sleep, and (2) index this score on a scale (e.g., a 0-100 scale) using one or more reference curves (e.g., non-cohort or cohort). The HRV is the variation in intervals between heartbeats. It is measured by the intervals between successive R waves, where R is a point corresponding to the peak of the QRS complex of an ECG wave. The HRV can be determined by calculating the root mean square of successive differences (RMSSD), shown below (next page):

$$RMSSD = \sqrt{\frac{1}{N-1}\left(\sum_{i=1}^{N-1}((R-R)_{i+1}-(R-R)_i)^2\right)},$$

where N=number of RR interval terms.

The HRV is an accurate predictor of overall cardiovascular health and is a physiological measure of stress. HRV measurements are highly influenced by many factors, for example, by how calm/agitated a person is, the person's position (e.g., sitting, standing, laying down), breathing patterns, and their state of rest/activeness. Therefore, determining the HRV immediately upon falling asleep (e.g., during the first 5 minutes of the first light sleep cycle) is an accurate metric of the person's ability to adapt to stressors throughout the day. The degree of recovery during the night can be determined by comparing the starting HRV to the HRV during the last 5 minutes of light sleep prior to waking up. As another example, the degree of recovery during the night can be determined by comparing the starting HRV to the HRV during the last 10 minutes of light sleep prior to waking up. The HRV can but need not be measured during similar stages of sleep (e.g., the beginning and ending HRV can both be measured during light sleep, the starting HRV can be measured during light sleep and the ending HRV can be measured during the last stage of sleep the person is in prior to waking up, for example, deep sleep or light sleep). The person's recovery score can be determined by the ending HRV values and the absolute and relative increase in HRV during the night.

In addition to the situational influencers that can affect HRV (e.g., position, breathing patterns, state of calm/agitation), age, gender, and fitness level can impact overall HRV levels as well.

A user's HRV can be tracked over time so that trends and changes can be determined. Additionally or alternatively, the user's HRV data can be compared other people's HRV data. This can desirably allow the user to know how their key marker of systemic health and resilience, HRV, is changing over time and how it compares to others. Because there are many factors that the HRV is sensitive to such as age, health, gender, and fitness level to account for, in addition to small changes in physical and mental health, when seeing how a person's HRV values compare to others, it can be advantageous to compare the user's HRV against people within a similar demographic, for example, using one or more cohort curves.

The ending HRV score can be translated to a 0-100 point scale to create the recovery score, for example, by referencing one or multiple HRV curves.

A method for determining HRV reference curves (e.g., cohort curves) can include using data from published research. For example, such research can include Nunan D, Sandercock G R, Brodie D A. "A quantitative systematic review of normal values for short-term heart rate variability in healthy adults." Pacing Clin Electrophysiol. 2010 November; 33(11):1407-17; Umetani K, Singer D H, McCraty R, Atkinson M. "Twenty-four hour time domain heart rate variability and heart rate: relations to age and gender over nine decades." J Am Coll Cardiol. 1998 Mar. 1; 31(3):593-601; and Elite HRV data, which are each herein incorporated by reference in their entireties for all purposes. For example, FIG. 26A illustrates that data from Table 4 of the Umetani and FIG. 26B illustrates that data from Elite HRV can be used. FIG. 26C illustrates an exemplary table showing the Umetani non-athlete data (FIG. 26A) and the Elite HRV athlete data (FIG. 26B) data by age, male athlete (M-A), female athlete (F-A), male non-athlete (M-NA) and female non-athlete (F-NA).

The average HRV for each cohort (e.g., age/age group, gender, fitness level) can be determined, along with the standard deviations of the determined averages.

For example, based on published studies of average HRV scores for men and women, athletes and non-athletes (e.g., Nunan, Umetani, Elite HRV), the HRV scores can be indexed to a 100 point scale by assigning a point value to the averages and standard deviations. The points assigned to the HRV statistics can be the same or different from the points assigned to statistics of other sleep variables (e.g., total sleep time, total deep sleep, longest deep sleep duration, strength of deep sleep). For example, for a 100 point scale, the average for a given HRV cohort (e.g., age/age group, fitness level and/or gender) can be assigned 85 points, one standard deviation above the average can be assigned 95 points, two standard deviations above the average can be assigned 100 points, one standard deviation below the average can be assigned 70 points and two standard deviations below the average can be assigned 35 points. This can be done for 4 cohorts within each age group: male athletes, female athletes, male non-athletes and female non-athletes. These four cohorts can be referred to as sub-cohorts such that age is the primary cohort and the categories male athlete, female athlete, male non-athlete and female non-athlete are sub-cohorts within each age category. The determined HRV statistics can be plotted and a curve can be fitted to the plotted points for each cohort/sub-cohort combination as described above with the reference curves for the other sleep variables. The curves can be polynomial or non-polynomial curves. For example, polynomial curves can be generated that best fit the HRV points, with caps at 0 and 100.

For example, FIGS. 27A-27D illustrate how 5 key points can be determined for four sub-cohorts (e.g., male athlete, female athlete, male non-athlete, female non-athlete) in four different age groups: 20 year old (FIG. 27A), 40 year old (FIG. 27B), 60 year old (FIG. 27C) and 80 year old (FIG. 27D). The top halves of FIGS. 27A-27D illustrate tables for the statistics (e.g., averages and standard deviations) calculated from HRV data. For example, row 1 of the tables lists the average HRV for the listed cohort (e.g., age) and sub-cohorts (e.g., male athlete, female athlete, male non-athlete, female non-athlete). Row 2 lists the standard deviation of the average and row 3 lists the standard deviation percentage relative to the average (e.g., 20 yr old male athlete: (5/86.5)×100=6%). Row 4 relists the HRV average for each category and rows 5-8 list the standard deviations shown, with the assigned HRV scores listed in the SCORE column of each figure. The statistics in rows 4-8 are an exemplary 5 key point set. Once the 5 key points are determined for each category (e.g., the values shown in rows 4-8), the points can be plotted. A trend line can be determined for each cohort/sub-cohort combination which best fits each 5 point data set (e.g., see the bottom halves of FIGS. 27A-27D), where the trend line can be a polynomial or non-polynomial trend line. The five key points calculated in the top halves of FIGS. 27A-27D are denoted as the five plotted points along each of the best fit curves in the bottom halves of FIGS. 27A-27D. The trend line can be plotted and smoothed. These generated trend lines can be the HRV reference curves.

For example, the bottom half of FIG. 27A illustrates 20 year old cohort curves for male athlete $54a_{MA}$, female athlete $54a_{FA}$, male non-athlete $54a_{MNA}$ and female non-athlete $54a_{FNA}$, FIG. 27B illustrates 40 year old cohort curves for male athlete $54b_{MA}$, female athlete $54b_{FA}$, male non-athlete $54b_{MNA}$ and female non-athlete $54b_{FNA}$, FIG. 27C illustrates 60 year old cohort curves for male athlete $54c_{MA}$, female athlete $54c_{FA}$, male non-athlete $54c_{MNA}$ and female non-athlete $54c_{FNA}$, and FIG. 27D illustrates 80 year old cohort curves for male athlete $54d_{MA}$, female athlete $54d_{FA}$, male non-athlete $54d_{MNA}$ and female non-athlete $54d_{FNA}$. The illustrated cohort curves can be defined by the polynomial equations illustrated in FIGS. 27A-27D. The key points (e.g., 5 points) are denoted as the five plotted points along each of the derived cohort curves in FIGS. 27A-27D. The illustrated curves can alternatively be non-polynomial curves, or both polynomial and non-polynomial curves can be fitted to the data.

Figure 28:
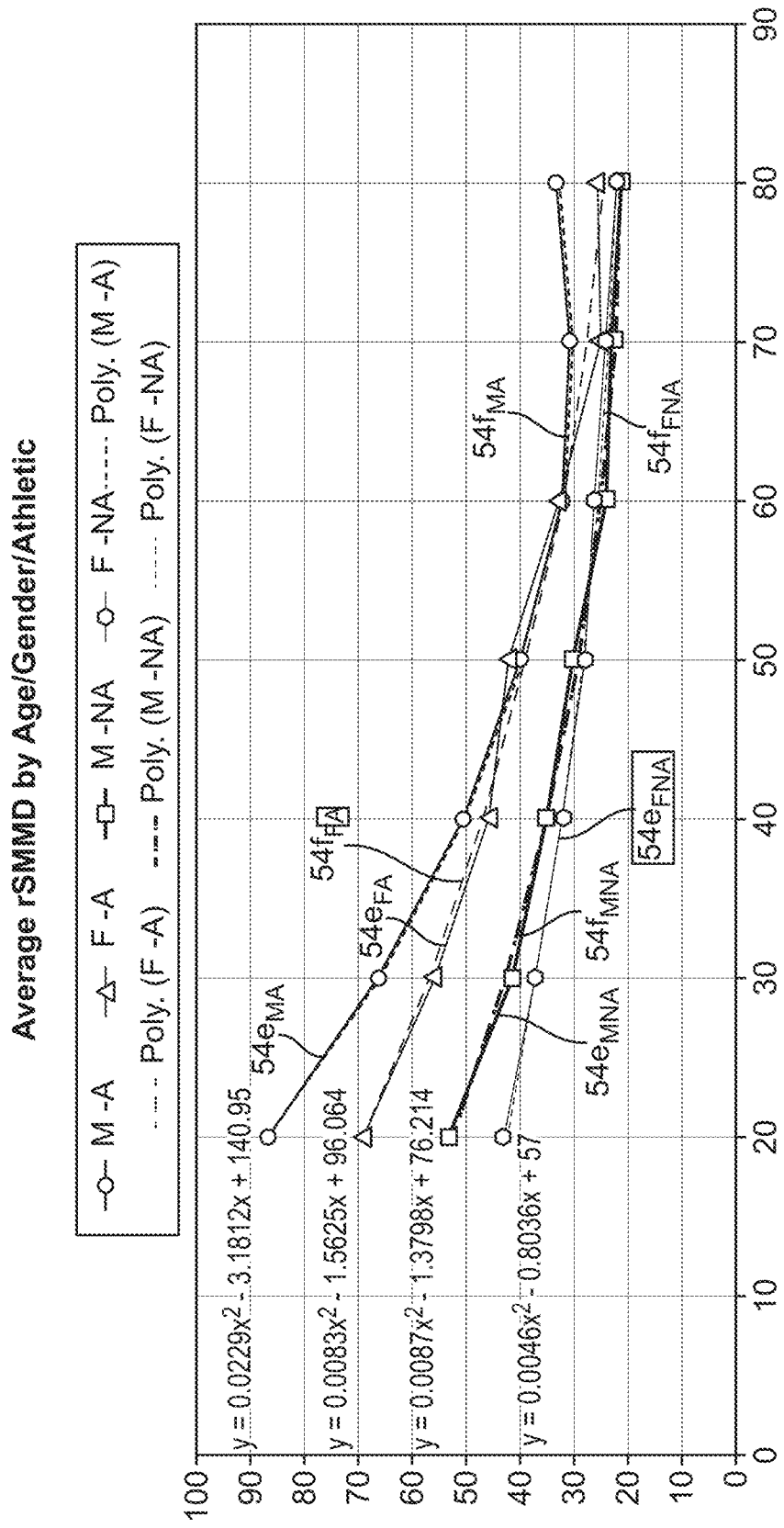
FIG. 28 illustrates a variation of HRV cohort curves.

FIG. 28 illustrates curves illustrated in FIGS. 27A-27D plotted together, with the data from each age group being averaged together (e.g., the female non-athlete curve data points are an average of the 20 yr, 40 yr, 60 yr and 80 yr curves $54a_{FNA}$, $54b_{FNA}$, $54c_{FNA}$ and $54d_{FNA}$, respectively) to generate a linear male athlete curve $54e_{MA}$, a polynomial male athlete curve $54f_{MA}$, a linear female athlete curve $54e_{FA}$, a polynomial female athlete curve $54f_{FA}$, a linear male non-athlete curve $54e_{MNA}$, a polynomial male non-athlete curve $54f_{MNA}$, a linear female non-athlete curve $54e_{FNA}$ and a polynomial female non-athlete curve $54f_{FNA}$, where "linear" can indicate that a straight line is connecting adjacent data points. The polynomial equation for the male athlete curve $54f_{MA}$ can be $y=0.0229x^2-3.1812x+140.95$. The polynomial equation for the female athlete curve $54f_{FA}$ can be $y=0.0083x^2-1.5625x+96.064$. The polynomial equation for the male non-athlete curve $54f_{MNA}$ can be $y=0.0087x^2-1.3798x+76.214$. The polynomial equation for the female non-athlete curve $54f_{FNA}$ can be $y=0.0046x^2-0.8036x+57$.

In this way, recovery points can be determined, for example, by reference to the HRV reference curves.

For any of the sleep variables, the data can be used to derive cohort curves, non-cohort curves, or both. Polynomial curves, non-polynomial curves, or both can be fitted to the data.

Although described above under separate headings, the methods described in each section can be used to derive the reference curve or curves for any other sleep variable.

The points assigned to the sleep variable statistics can be the same or different from the points assigned to other sleep variable statistics. The assigned point value for each statistic can be a negative value, zero, or a positive value. For example, the assigned point value for each statistic can assigned a point value of −100 points to 100 points, including every 1 point increment within this range.

Figure 29A:
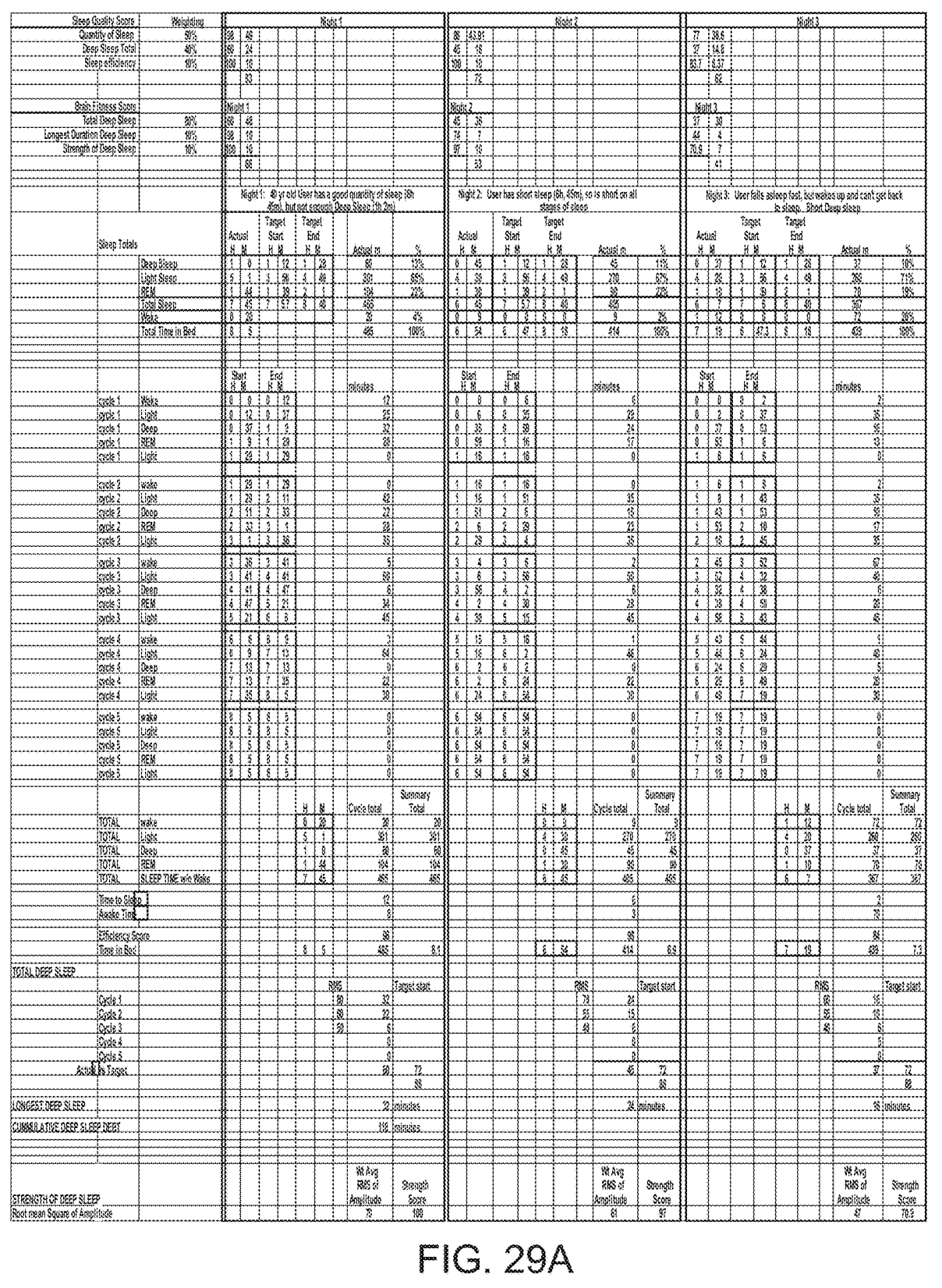
Figure 29B:
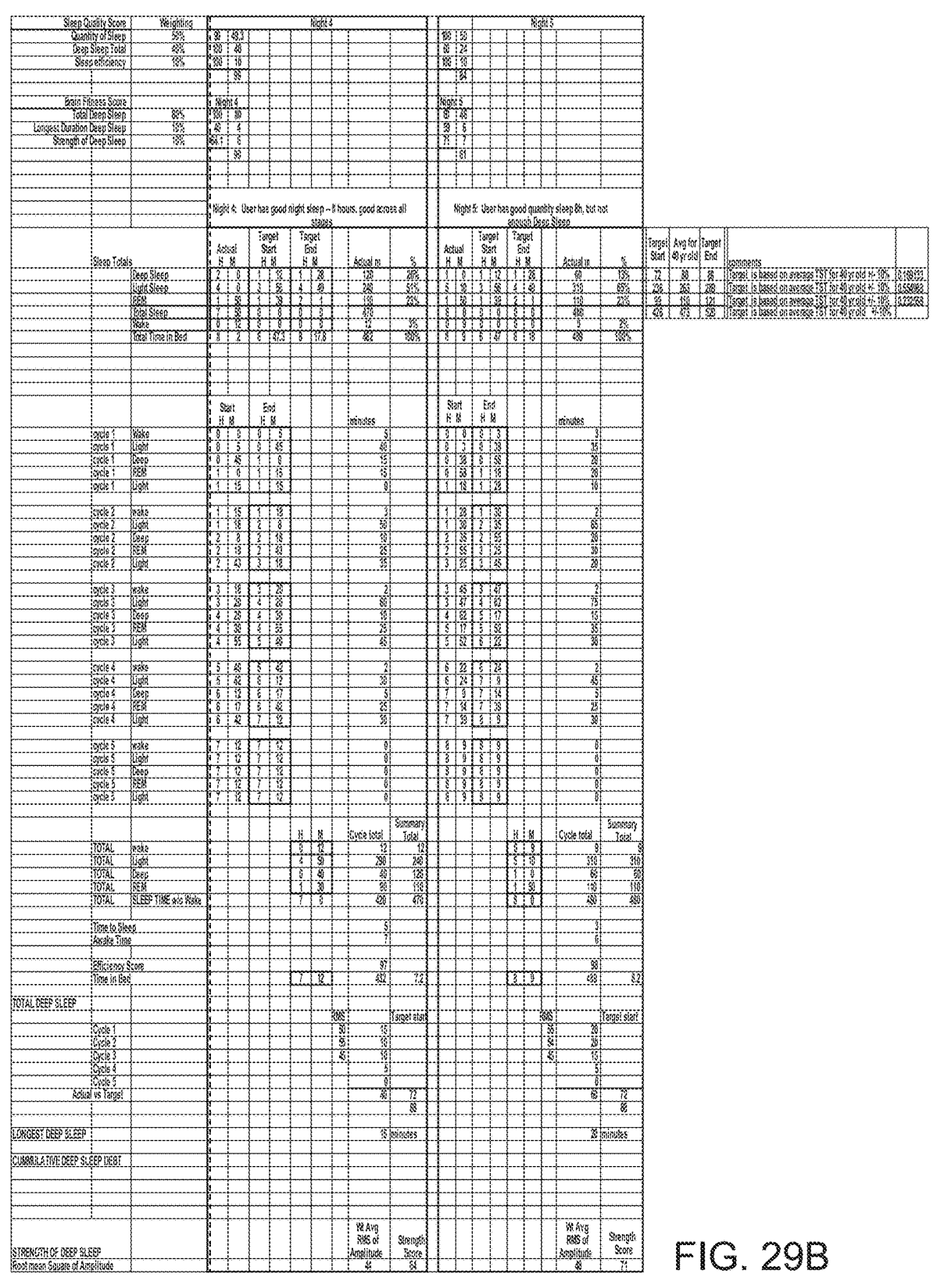

FIGS. 29A and 29B illustrate data acquired and analyzed on 5 nights: Night 1, Night 2, Night 3, Night 4 and Night 5.

FIG. 30A illustrates a variation of a graphical display 105a having the illustrated display features for a sleep quality score of 82.

FIG. 30B illustrates a variation of a graphical display 105b having the illustrated display features for a brain fitness score of 61.

FIG. 30C illustrates a variation of a graphical display 105c having the illustrated display features for the sleep cycle durations illustrated in FIGS. 29A and 29B.

FIG. 30D illustrates a variation of a graphical display 105d having the illustrated display features for sleep totals for a night for total sleep time ("Total"), total deep sleep ("Deep"), REM sleep ("REM") and light sleep ("Light").

FIG. 30E illustrates a variation of a graphical display 105e having the illustrated display features for sleep efficiency.

FIG. 30F illustrates a variation of a graphical display 105f having the illustrated display features for longest deep sleep and 5-night cumulative deficit.

A number of variations have been described. Nevertheless, it will be understood by one of ordinary skill in the art that various modifications may be made without departing from the spirit and scope of the variations. In addition, the flowcharts, logic flows, and algorithms depicted in the figures do not require the particular order shown, or sequential order, to achieve desirable results, and are exemplary only. In addition, other steps or operations may be provided, or steps or operations may be eliminated, from the described flows and algorithms, and other components and/or features may be added to, or removed from, the described and contemplated systems. Accordingly, other variations are within the scope of the following claims.

It will be understood by one of ordinary skill in the art that the various methods and processes disclosed herein may be embodied in a non-transitory readable medium, machine-readable medium, and/or a machine accessible medium comprising instructions compatible, readable, and/or executable by a processor or processing unit of a machine, device, or computing device. The structures and modules in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

The specific embodiments described herein are offered by way of example only. Moreover, such devices and methods may be applied to other sites within the body. Modification of the above-described assemblies and methods for carrying out the invention, combinations between different variations as practicable, and variations of aspects of the invention that are obvious to those of skill in the art are intended to be within the scope of the claims.

The claims are not limited to the exemplary variations shown in the figures, but instead may claim any feature disclosed or contemplated in the disclosure as a whole. Any elements described herein as singular can be pluralized (i.e., anything described as "one" can be more than one). Any species element of a genus element can have the characteristics or elements of any other species element of that genus. Some elements may be absent from individual figures for reasons of illustrative clarity. The above-described configurations, elements or complete assemblies and methods and their elements for carrying out the disclosure, and variations of aspects of the disclosure can be combined and modified with each other in any combination. All devices, apparatuses, systems, methods, and algorithms described herein can be used for medical (e.g., diagnostic, therapeutic or rehabilitative) or non-medical purposes.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

If there is any ambiguity above, every possible interpretation of that ambiguity is hereby disclosed for all purposes, thereby removing such ambiguity from the application.

We claim:

1. A sleep monitoring system, comprising:
   one or more electroencephalography (EEG) electrodes configured to measure a user's brain activity during sleep;
   a processor configured to quantify a quality of a slow-wave sleep of the user by determining one or more sleep performance scores associated with a measured brain activity; and
   wherein the one or more sleep performance scores comprises a sleep quality score that is calculated from a total sleep time parameter, total deep sleep time parameter, and sleep efficiency parameter during a selected time period and a brain fitness score that is calculated from a total deep sleep parameter, longest deep sleep parameter, and deep sleep strength parameter wherein the deep sleep strength parameter is calculated from a root mean square of an amplitude of the slow-wave sleep during the selected time period, and wherein the system is configured to provide at least one of audio stimulation, visual stimulation, and cranial electrical stimulation to the user during a selected portion of a sleep cycle of the user depending upon the one or more sleep performance scores associated with the measured brain activity.

2. The system of claim 1, wherein the sleep quality score is based at least partly on user's fitness level, health habits, and/or genetic characteristics.

3. The system of claim 2, wherein the user's fitness level, health habits, and genetic characteristics comprise at least one of age and gender.

4. The system of claim 1, wherein the brain fitness score is based at least partly on the user's fitness level, health habits, and/or genetic characteristics.

5. The system of claim 4, wherein the user's fitness level, health habits, and genetic characteristics comprise at least one of age and gender.

6. The system of claim 1, wherein the processor is further configured to calculate a recovery score that is a function of the user's heart rate variability during sleep.

7. The system of claim 1, wherein the processor is further configured to determine a value of one or more sleep parameters based at least partly on the measured brain activity, wherein the processor is further configured to compare a determined value of the one or more sleep parameters to one or more threshold criteria, and wherein the processor is further configured to provide one or more sleep-related observations and/or recommendations upon determining that the value of the one or more sleep parameter fall below the one or more threshold criteria.

8. A method of quantifying a quality of a user's sleep, the method comprising:
   measuring, via one or more electroencephalography (EEG) biosensors, a user's brain activity during sleep;
   quantifying, via a computer system, a quality of a slow-wave sleep of the user by
   determining sleep performance scores associated with a measured brain activity; and
   providing at least one of audio stimulation, visual stimulation, and cranial electrical stimulation during the slow-wave sleep based upon the sleep performance scores associated with the measured brain activity,
   wherein the sleep performance scores comprises a sleep quality score and a brain fitness score and wherein the sleep quality score is a function of total sleep time parameter, deep sleep parameter, and sleep efficiency parameter and wherein the brain fitness score is a function of total deep sleep time parameter, longest deep sleep parameter, and deep sleep strength parameter wherein the deep sleep strength parameter is calculated from a root mean square of an amplitude of the slow-wave sleep.

9. The method of claim 8, wherein the sleep quality score is based at least partly on the user's fitness level, health habits, and/or genetic characteristics.

10. The system of claim 8, wherein the user's fitness level, health habits, and genetic characteristics comprise at least one of age and gender.

11. The method of claim 8, wherein the brain fitness score is based at least partly on the user's fitness level, health habits, and/or genetic characteristics.

12. The method of claim 8, further comprising calculating a recovery score that is a function of the user's heart rate variability during sleep.

13. The method of claim 8, further comprising:
   determining, via the computer system, a value of one or more sleep parameters based at least partly on the measured brain activity;
   comparing, via the computer system, the determined value of the one or more sleep parameters to one or more threshold criteria; and
   providing, via the computer system, one or more sleep-related observations and/or recommendations upon determining that one or more of the determined values of the one or more sleep parameters fall below one or more threshold criteria.

14. A method of quantifying a brain fitness score of a subject, comprising:
   measuring one or more parameters relating to a brain activity of the subject;
   determining a total deep sleep time parameter based upon a function of a total amount of deep sleep time measured from the subject;
   determining a longest deep sleep parameter based upon a function of a total amount of longest deep sleep time measured from the subject;
   determining a deep sleep strength parameter wherein the deep sleep strength parameter is calculated from a root mean square of an amplitude of a slow-wave sleep based upon a function of a deep sleep strength measured from the subject;
   calculating the brain fitness score based upon a weighting of the total deep sleep time parameter, longest deep sleep parameter, and deep sleep strength parameter; and
   providing an audio stimulation during a selected portion of a slow-wave sleep cycle of the subject depending upon a value of the brain fitness score.

15. The method of claim 14, wherein calculating the brain fitness score comprises adding the total deep sleep time parameter, longest deep sleep parameter, and deep sleep strength parameter.

16. The method of claim 15, wherein calculating further comprises weighting each of the total deep sleep parameter, longest deep sleep parameter, and deep sleep strength parameter.

17. The method of claim 14, further comprising providing one or more recommendations to the subject for increasing the brain fitness score.

* * * * *